US011230556B2

(12) United States Patent
Gao et al.

(10) Patent No.: US 11,230,556 B2
(45) Date of Patent: Jan. 25, 2022

(54) 6,5-FUSED HETEROARYL PIPERIDINE ETHER ALLOSTERIC MODULATORS OF THE M4 MUSCARINIC ACETYLCHOLINE RECEPTOR

(71) Applicant: Merck Sharp & Dohme Corp., Rahway, NJ (US)

(72) Inventors: Xiaolei Gao, Bridgewater, NJ (US); Sandra L. Knowles, Princeton, NJ (US); Chunsing Li, Shanghai (CN); Michael Man-Chu Lo, Bedminster, NJ (US); Robert D. Mazzola, Jr., Stewartsville, NJ (US); Debra L. Ondeyka, Fanwood, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 62 days.

(21) Appl. No.: 16/471,672

(22) PCT Filed: Dec. 18, 2017

(86) PCT No.: PCT/US2017/066921
§ 371 (c)(1),
(2) Date: Jun. 20, 2019

(87) PCT Pub. No.: WO2018/118736
PCT Pub. Date: Jun. 28, 2018

(65) Prior Publication Data
US 2020/0095261 A1 Mar. 26, 2020

(30) Foreign Application Priority Data

Dec. 22, 2016 (WO) ................ PCT/CN2016/111527

(51) Int. Cl.
| | | |
|---|---|---|
| *C07D 498/04* | (2006.01) | |
| *C07D 471/04* | (2006.01) | |
| *C07D 487/04* | (2006.01) | |
| *C07D 491/048* | (2006.01) | |
| *C07D 513/04* | (2006.01) | |
| *C07D 471/14* | (2006.01) | |
| *C07D 498/14* | (2006.01) | |
| *C07D 401/14* | (2006.01) | |

(52) U.S. Cl.
CPC ......... *C07D 498/14* (2013.01); *C07D 401/14* (2013.01); *C07D 471/04* (2013.01); *C07D 471/14* (2013.01); *C07D 487/04* (2013.01); *C07D 491/048* (2013.01); *C07D 513/04* (2013.01)

(58) Field of Classification Search
CPC .............. C07D 498/14; C07D 401/14; C07D 471/04; C07D 471/14; C07D 487/04; C07D 491/048; C07D 513/04
See application file for complete search history.

(56) References Cited

U.S. PATENT DOCUMENTS

| | | |
|---|---|---|
| 5,574,044 A | 11/1996 | Thompson et al. |
| 5,691,323 A | 11/1997 | Thompson et al. |
| 6,699,880 B1 | 3/2004 | Yamakawa et al. |
| 6,900,224 B2 | 5/2005 | Ledoussal et al. |
| 7,074,801 B1 | 7/2006 | Yoshida et al. |
| 7,858,635 B2 | 12/2010 | Makings et al. |
| 7,964,602 B2 | 6/2011 | MacDonald et al. |
| 8,071,776 B2 | 12/2011 | Esteban et al. |
| 8,168,639 B2 | 5/2012 | Kogan |
| 8,349,850 B2 | 1/2013 | Tworowski et al. |
| 8,614,319 B2 | 12/2013 | Tworowski et al. |
| 9,034,872 B2 | 5/2015 | Tworowski et al. |
| 9,056,875 B2 | 6/2015 | Lindsley et al. |
| 9,056,876 B2 | 6/2015 | Conn et al. |
| 9,493,481 B2 | 11/2016 | Lindsley et al. |
| 9,593,106 B2 | 3/2017 | Livermore et al. |
| 9,637,498 B2 | 5/2017 | Lindsley et al. |
| 10,329,289 B2 | 6/2019 | Bao |
| 10,351,564 B2 | 7/2019 | Gao |
| 10,512,638 B2 | 12/2019 | Rudd |
| 2007/0004763 A1 | 1/2007 | Baindur et al. |
| 2008/0306107 A1 | 12/2008 | Griffin et al. |
| 2009/0247584 A1 | 10/2009 | Holzemann et al. |

(Continued)

FOREIGN PATENT DOCUMENTS

| | | |
|---|---|---|
| EP | WO2011/034741 | 2/2011 |
| JP | 2013237634 | 11/2013 |

(Continued)

OTHER PUBLICATIONS

European Search Report dated Apr. 28, 2020, PCTUS2017066921, 5 pages.
ACS-RN1564913-75-2 STN Registry Mar. 9, 2014.
ACS-RN1774819-47-4 STN Registry Jun. 7, 2015.
ACS-RN1912672-03-3 STN Registry May 18, 2016.
Bewley, Blake R., et al., Discovery of a novel, CNS penetrant M4PAM chemotype based on a 6-fluoro-4(piperiden-1-yl)quinoline-3-carbonitrile core, Bioorganic and Med Chem Letters, 2017, 4274-4279, 27.
Byun, Nellie B, et al., Antipsychotic Drug-like Effects of the Selective M4 Muscarinic Acetylcholine Receptor Positive Allosteric Modulator VU02552100, Neuropsychopharmacology, 2014, 1578-1593, 39.

(Continued)

*Primary Examiner* — Patricia L Morris

(74) *Attorney, Agent, or Firm* — Eric A. Meade; John C. Todaro

(57) ABSTRACT

The present invention is directed to 6,5-fused heteroarylpiperidine ether compounds which are allosteric modulators of the M4 muscarinic acetylcholine receptor. The present invention is also directed to uses of the compounds described herein in the potential treatment or prevention of neurological and psychiatric disorders and diseases in which M4 muscarinic acetylcholine receptors are involved. The present invention is also directed to compositions comprising these compounds. The present invention is also directed to uses of these compositions in the potential prevention or treatment of such diseases in which M4 muscarinic acetylcholine receptors are involved.

11 Claims, No Drawings

(56) References Cited

U.S. PATENT DOCUMENTS

| | | | |
|---|---|---|---|
| 2012/0058984 A1 | 3/2012 | Alder et al. | |
| 2016/0200733 A1 | 7/2016 | Lindsley et al. | |
| 2017/0096437 A1 | 4/2017 | Congreve et al. | |
| 2017/0369505 A1 | 12/2017 | Lindsley et al. | |

FOREIGN PATENT DOCUMENTS

| | | |
|---|---|---|
| JP | 2014047192 | 3/2014 |
| JP | 2014062063 | 4/2014 |
| WO | 1998006697 A1 | 2/1998 |
| WO | WO2006/125180 | 11/2006 |
| WO | WO2015/293281 A1 | 12/2015 |
| WO | 2017112719 A1 | 6/2017 |

OTHER PUBLICATIONS

Eglen, Richard M., Muscarinic receptor ligands and their therapeutic potential, Current Opinion in Chemical Biology, 1999, 426-432, 3.

Kargbo, Robert B., Allosteric Modulators of the M4 Muuscarinic Acetylcholine Receptor, ACS Medicinal Chemistry Letters, 2017, 903-904, 8.

Lindsley, Craig W., et al., Discovery of the mAChR subtype selective M4 positive allosteric moduclators, Current Topics in Medicinal Chemistry, 2008, 531, 8-6.

Long, Madeline F., Discovery of a nove 2,4-dimethylquinoline-6-carboxamide M4 positive allosteric modulator (PAM) Chemotype via scaffold hopping, Bioorganic and Med Chem Letters, 2017, 4999-5001, 27.

Melancon, Bruce J., et al., Optimization of M4 Positive Allosteric Modulators (PAMs): The discovery of VU0476406, a non-human primate in vivo tool compound for translational pharmacology, Bioorganic and Med Chem Letters, 2017, 2296-2301, 27.

PCT Search Report and Written Opinion for PCT/CN2016/111527 dated Sep. 21, 2017.

PCT Search Report and Written Opinion for PCT/US2017/066921 dated Apr. 23, 2018.

Pubchem, Substance Record for SID 237207476, Available Date: Feb. 13, 2015 [retrieved on Jan. 23, 2018], Retrieved from the Internet: URL:https://pubchem.ncbi.nlm.nih.gov/substance/237207476.

PUBCHEM-SID-215465399, Oct. 20, 2014, retrieved from internet.

RN: 1394484-56-0 Registry STN American Chemical Society; Feb. 23, 2014.

RN: 1546829-79-1 Registry STN American Chemical Society; Feb. 23, 2014.

RN: 1552923-38-2 Registry STN American Chemical Society; Feb. 23, 2014.

RN:1424588-49-7 Registry STN American Chemical Society; Feb. 23, 2014.

Salovich, James M., et al., Discovery of N-(4-methoxy-7-methylbenzo[d]thiazol-2-yl)..., Bioorganic and Med Chem Letters, 2012, 5084-5088, 22.

Tarr, James C., Challenges in the development of an M4PAM preclinical candidate: The discovery, SAR and in vivo characterization of a ...., Bioorganic and Med Chem Letters, 2017, 2990-2995, 27.

Tarr, James C., et al., Challenges in the development of an M4PAM Preclinical candidate:..., Bioorganic and Med Chem Letters, 2017, 5179-5184, 27.

Utley, Thomas, Synthesis and SAR of a novel metabotropic glutamate receptor 4...., Bioorganic and Med Chem Letters, 2011, 6955-6959, 21.

Vardigan, J.D., Psychopharmacology, Improved Cognition without adverse effects ...., 2015, 1859-1866, 232:11, US.

Wood, Michael R., et al., Discovery and Optimization of a novel series of highly CNS penetrant M4PAMS based on a 5,6-dimethul-4-(piperidin-1-yl)thieno[2,3-d]pyrimidine core, Bioorganic and Med Chem Letters, 2016, 3029-3033, 26.

Wood, Michael R., et al., Discovery of VU0467485/AZ13713945: An M4PAM evaluated as a Preclinical candidate for the Treatment of Schizophrenia, ACS Medicinal Chemistry Letters, 2017, 233-238, 8.

6,5-FUSED HETEROARYL PIPERIDINE ETHER ALLOSTERIC MODULATORS OF THE M4 MUSCARINIC ACETYLCHOLINE RECEPTOR

CROSS REFERENCE TO RELATED APPLICATIONS

This application is a U.S. National Phase application under 35 U.S.C. § 371 of PCT Application No. PCT/US2017/066921, filed Dec. 18, 2017, which claims priority under 35 U.S.C. § 119(e) from PCT/CN2016/111527, filed Dec. 22, 2016.

BACKGROUND OF THE INVENTION

Acetylcholine (ACh) is a key neurotransmitter that modulates neuronal function in the peripheral nervous system (PNS) and central nervous system (CNS). ACh mediates its actions via two families of receptors, termed the muscarinic ACh receptors (mAChRs) and the nicotinic ACh receptors (nAChRs). A large body of evidence suggests that basal forebrain cholinergic neurons and basalo-cortical cholinergic pathways are selectively vulnerable to degeneration in Alzheimer's disease. It has therefore been hypothesized that cholinergic hypofunction contributes to the cognitive deficits of patients suffering from Alzheimer's disease. Consequently, acetylcholinesterase inhibitors, which inhibit ACh hydrolysis and potentiate cholinergic signaling have been demonstrated to not only provide improvements in cognitive symptoms associated with Alzheimer's disease, but also show efficacy in treating the psychiatric symptoms. Acetylcholinesterase inhibitors, however, have not been shown to change the underlying disease pathology.

Another potential pharmacotherapeutic target to counteract cholinergic hypofunction is the activation of muscarinic acetylcholine receptors (mAChRs). Muscarinic acetylcholine receptors are members of the G protein-coupled receptor superfamily which mediate the actions of the neurotransmitter acetylcholine in both the central and peripheral nervous system.

Muscarinic acetylcholine receptors are prevalent throughout the body and five distinct muscarinic receptors (M1-M5) have been identified in mammals. The muscarinic receptors are known to contain one or more allosteric sites which may alter the affinity with which muscarinic ligands bind to the primary binding or orthosteric sites. In the central nervous system, muscarinic receptors are involved in cognitive, behavior, sensory, motor and autonomic functions. The M4 muscarinic acetylcholine receptor is predominantly expressed in the striatum, but also in the hippocampus and cortex.

Muscarinic receptors in the central nervous system play a critical role in mediating higher cognitive processing and control of dopamine release. Administration of nonselective muscarinic antagonists can induce cognitive deficits and psychosis in humans suggesting that mAChR activation may provide pro-cognitive and antipsychotic efficacy. Accordingly, several mAChR agonists have been developed and entered clinical studies for the treatment of cognitive and psychiatric symptoms associated with Alzheimer's and neuropsychiatric diseases such as schizophrenia. (Carruthers, Neuroscience & Biobehavioral Rev., 2015, 55: 393-402; Jones, et al. Neuropsychopharmacology, 2012, 37: 16-42). One of these, the M1/M4 preferring mAChR agonist xanomeline was assessed in patients with Alzheimer's disease, and while showing a trend for improving cognitive deficits, did produce robust and dose-dependent reductions in hallucinations, delusions, vocal outbursts, and other behavioral disturbances in these patients. A subsequent study in patients with schizophrenia demonstrated that xanomeline produced robust improvements in positive, negative and cognitive symptoms. (Bodick, et al., Arch Neurol. 1997; 54: 465-73). Xanomeline, in addition to other mAChR agonists have been demonstrated to produce robust antipsychotic-like effects in a number of preclinical paradigms. For instance, xanomeline, reverses a number of dopamine driven behaviors, including amphetamine induced locomotion in rats, apomorphine induced climbing in mice, dopamine agonist driven turning in unilateral 6-OH-DA lesioned rats and amphetamine induced motor unrest in monkeys (without EPS liability). It also has been shown to inhibit A10, but not A9, dopamine cell firing and conditioned avoidance and induces c-fos expression in prefrontal cortex and nucleus accumbens, but not in striatum in rats. These data are all suggestive of an atypical antipsychotic-like profile. Subsequent studies with M4 knockout mice have demonstrated that the antipsychotic-like effects of xanomeline are mediated by the M4 receptor. Despite these promising clinical and preclinical effects, xanomeline, like other muscarinic agonists, ultimately failed in clinical development due to lack of adequate receptor subtype selectivity resulting in dose-limiting side effects including disturbed gastrointestinal motility, bradycardia, nausea and vomiting.

The development of selective M4 positive allosteric modulators (PAMs) is a strategy to overcome the challenges of developing selective orthosteric muscarinic agonists. Indeed, studies with M4 PAMs have shown that selective activation of M4 mAChRs can reverse both hyperdopaminergic and hypoglutamatergic behaviors in preclinical models. Accordingly, the compounds of the present invention, which are allosteric modulators of the M4 muscarinic acetylcholine receptor, are believed to be useful in the treatment of Alzheimer's disease and other diseases mediated by the muscarinic M4 muscarinic acetylcholine receptor.

SUMMARY OF THE INVENTION

The present invention is directed to 6,5-fused heteroarylpiperidine ether compounds which are allosteric modulators of the M4 muscarinic acetylcholine receptor. The present invention is also directed to uses of the compounds described herein in the potential treatment or prevention of neurological and psychiatric disorders and diseases in which M4 muscarinic acetylcholine receptors are involved. The present invention is also directed to compositions comprising these compounds. The present invention is also directed to uses of these compositions in the potential prevention or treatment of such diseases in which M4 muscarinic acetylcholine receptors are involved.

DETAILED DESCRIPTION OF THE INVENTION

The present invention is directed to compounds of the formula I:

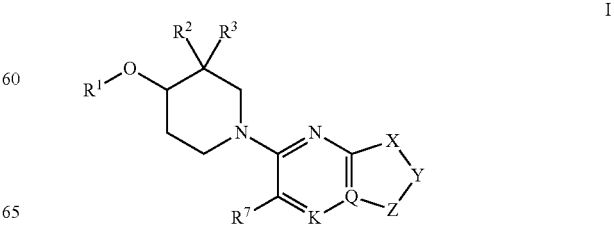

wherein:
K is N or C—R[8];
Q is N or C;
X is selected from the group consisting of:
  (1) =N—,
  (2) —(NR[9])—,
  (3) —(C=O)—,
  (4) =(CR[10])—, and
  (5) —(CHR[10])—;
Y is selected from the group consisting of:
  (1) —O—,
  (2) =N—,
  (3) —(NR[9])—,
  (4) —(C=O)—, and
  (5) —(CR[11]R[12])—;
Z is selected from the group consisting of:
  (1) —(NR[9])—,
  (2) —(C=O)—,
  (3) =(CR[12])—,
  (4) —(CHR[12])—, and
  (5) —(SO$_2$)—;
with the proviso that if X is —(CHR[10])—, Y is —(NR[9])—, and Z is —(C=O)—, then Q is —N—;
R[1] is selected from the group consisting of:
  (1) hydrogen;
  (2) —C$_{1-6}$alkyl, which is unsubstituted or substituted with substituents selected from the group consisting of: hydroxy, fluoro, —CN, —O—C$_{1-6}$alkyl, and C$_{3-6}$cycloalkyl;
  (3) a phenyl, heteroaryl or heterocyclyl ring, wherein the phenyl, heteroaryl or heterocyclyl ring is substituted with one or more R[1a], R[1b] and R[1c], wherein R[1a], R[1b] and R[1c] are independently selected from the group consisting of:
    (a) hydrogen,
    (b) hydroxy,
    (c) halogen,
    (d) C$_{1-6}$alkyl, which is unsubstituted or substituted with substituents selected from the group consisting of: hydroxy, cyclopropyl, cyclobutyl, cyclopentyl, fluoro, and —OCH$_3$,
    (e) —O—C$_{1-6}$alkyl, which is unsubstituted or substituted with substituents selected from the group consisting of: hydroxy, cyclopropyl, cyclobutyl, cyclopentyl, fluoro, and —OCH$_3$,
    (f) C$_{3-6}$cycloalkyl, which is unsubstituted or substituted with substituents selected from the group consisting of: hydroxy, cyclopropyl, cyclobutyl, cyclopentyl, fluoro, and —OCH$_3$, and
    (p) —CN;
R[2] and R[3] are independently selected from the group consisting of:
  (1) hydrogen,
  (2) fluoro,
  (3) hydroxy, and
  (4) —CH$_3$;
R[7] and R[8] are independently selected from the group consisting of:
  (1) hydrogen,
  (2) C$_{1-6}$alkyl,
  (5) -fluoro, and
  (6) -chloro;
R[9] is selected from the group consisting of:
  (1) hydrogen,
  (2) —C$_{1-6}$alkyl, which is unsubstituted or substituted with substituents selected from the group consisting of: hydroxy, methoxy, fluoro, —C(C=O)O—C$_{1-6}$alkyl, —NH$_2$, —NH(C$_{1-6}$alkyl), —N(C$_{1-6}$alkyl)$_2$, —C(C=O)NH$_2$, —C(C=O)OH, oxetanyl, or pyridyl,
  (3) —C$_{3-6}$cycloalkyl, which is unsubstituted or substituted with fluoro,
  (4) —(C=O)—C$_{1-6}$alkyl, which is unsubstituted or substituted with substituents selected from the group consisting of: hydroxy, methoxy, ethoxy, fluoro, azetidinyl, oxetanyl, or —C$_{3-6}$cycloalkyl which is unsubstituted or substituted with fluoro, pyrrolyl, imidazolyl, —NH$_2$, —NH(C$_{1-6}$alkyl), or —N(C$_{1-6}$alkyl)$_2$,
  (4) —(C=O)O—C$_{1-6}$alkyl,
  (5) —(SO$_2$)—C$_{1-6}$alkyl, and
  (6) —(SO$_2$)—C$_{3-6}$cycloalkyl,
and when Y is —(NR[9])— and X is —(CHR[10])—, X and Y may be joined together with
  —CH$_2$OCH$_2$CH$_2$— to form a morpholinyl ring, or with
  —CH$_2$NHCH$_2$CH$_2$— to form a piperazinyl ring;
each of R[10], R[11] and R[12] is independently selected from the group consisting of:
  (1) hydrogen,
  (2) fluoro,
  (3) —OH,
  (3) —CH$_3$,
  (4) —CF$_3$,
  (5) —CH$_2$OH,
  (6) —CH$_2$CH$_2$OH, and
  (7) —C(CH$_3$)$_2$OH;
or a pharmaceutically acceptable salt thereof.

An embodiment of the present invention includes compounds of the formula Ia:

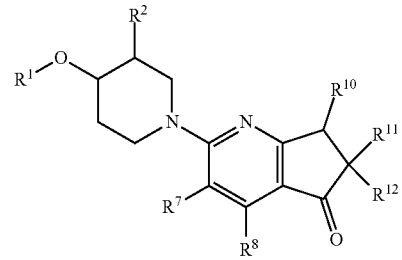

Ia wherein R[1], R[2], R[7], R[8], R[10], R[11] and R[12] are defined herein; or a pharmaceutically acceptable salt thereof.

An embodiment of the present invention includes compounds of the formula Ib:

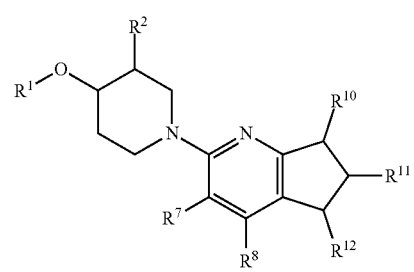

Ib wherein R[1], R[2], R[7], R[8], R[10], R[11] and R[12] are defined herein; or a pharmaceutically acceptable salt thereof.

An embodiment of the present invention includes compounds of the formula Ic:

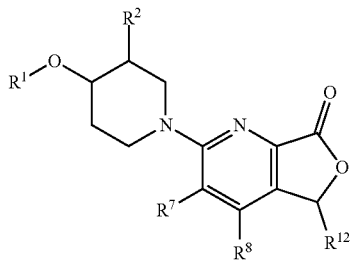

Ic wherein $R^1$, $R^2$, $R^7$, $R^8$ and $R^{12}$ are defined herein; or a pharmaceutically acceptable salt thereof.

An embodiment of the present invention includes compounds of the formula Id:

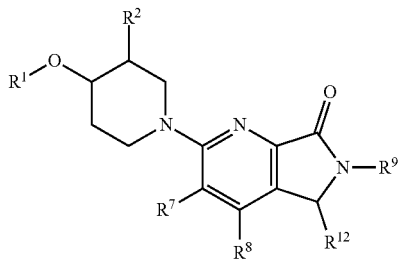

Id wherein $R^1$, $R^2$, $R^7$, $R^8$, $R^9$ and $R^{12}$ are defined herein; or a pharmaceutically acceptable salt thereof.

An embodiment of the present invention includes compounds of the formula Ie:

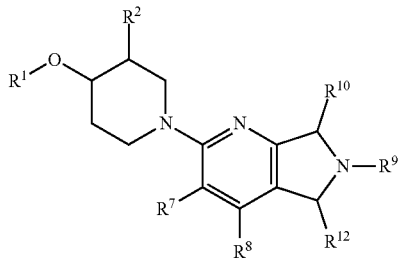

Ie wherein $R^1$, $R^2$, $R^7$, $R^8$, $R^9$, $R^{10}$ and $R^{12}$ are defined herein; or a pharmaceutically acceptable salt thereof.

An embodiment of the present invention includes compounds of the formula If:

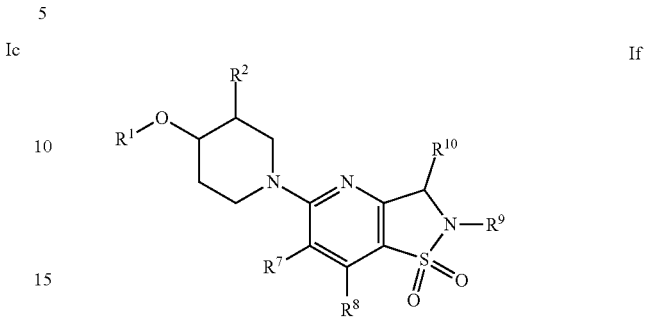

If wherein $R^1$, $R^2$, $R^7$, $R^8$, $R^9$ and $R^{10}$ are defined herein; or a pharmaceutically acceptable salt thereof.

An embodiment of the present invention includes compounds of the formula Ig:

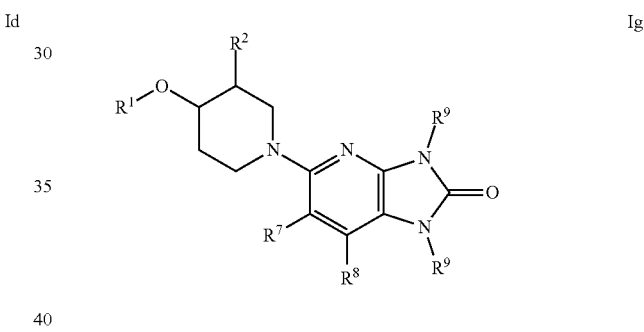

Ig wherein $R^1$, $R^2$, $R^7$, $R^8$, and $R^9$ are defined herein; or a pharmaceutically acceptable salt thereof.

An embodiment of the present invention includes compounds of the formula Ih:

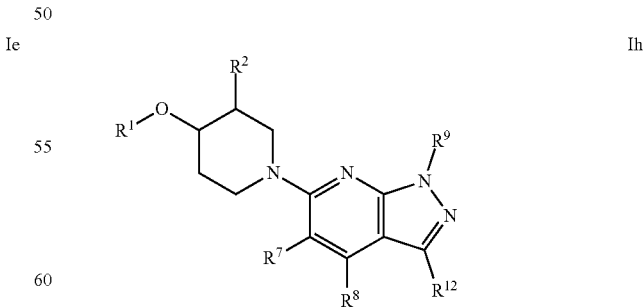

Ih wherein $R^1$, $R^2$, $R^7$, $R^8$, $R^9$ and $R^{12}$ are defined herein; or a pharmaceutically acceptable salt thereof.

An embodiment of the present invention includes compounds of the formula Ii:

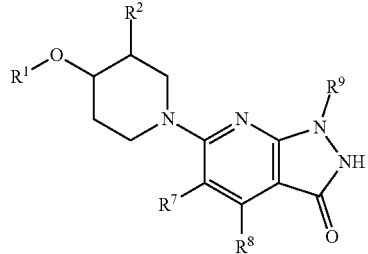

Ii wherein $R^1$, $R^2$, $R^7$, $R^8$ and $R^9$ are defined herein; or a pharmaceutically acceptable salt thereof.

An embodiment of the present invention includes compounds of the formula Ij:

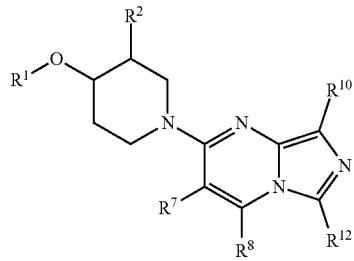

Ij wherein $R^1$, $R^2$, $R^7$, $R^8$, $R^{10}$ and $R^{12}$ are defined herein; or a pharmaceutically acceptable salt thereof.

An embodiment of the present invention includes compounds of the formula Ik:

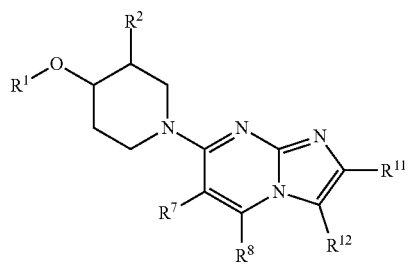

Ik wherein $R^1$, $R^2$, $R^7$, $R^8$, $R^{11}$ and $R^{12}$ are defined herein; or a pharmaceutically acceptable salt thereof.

An embodiment of the present invention includes compounds of the formula Im:

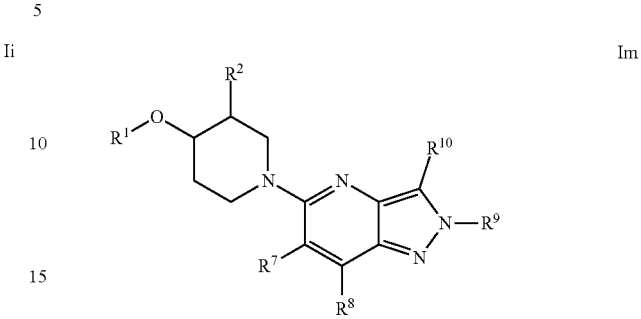

Im wherein $R^1$, $R^2$, $R^7$, $R^8$, $R^9$ and $R^{12}$ are defined herein; or a pharmaceutically acceptable salt thereof.

An embodiment of the present invention includes compounds of the formula In:

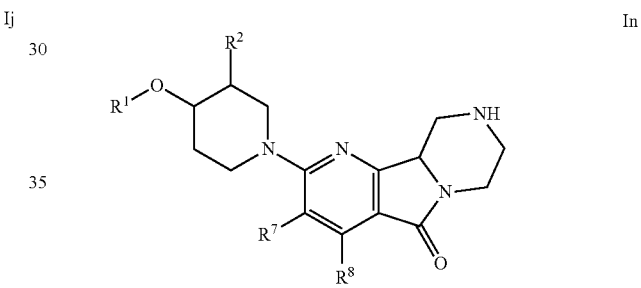

In wherein $R^1$, $R^2$, $R^7$ and $R^8$ are defined herein; or a pharmaceutically acceptable salt thereof.

An embodiment of the present invention includes compounds of the formula Io:

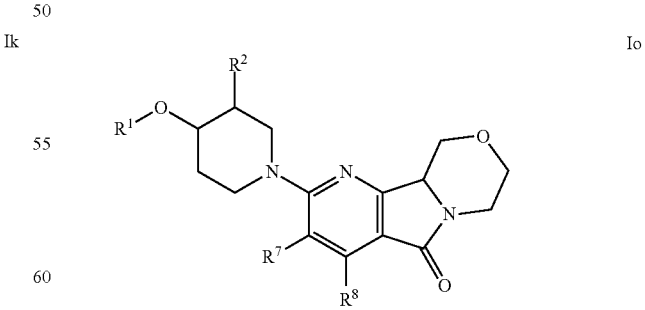

Io wherein $R^1$, $R^2$, $R^7$ and $R^8$ are defined herein; or a pharmaceutically acceptable salt thereof.

An embodiment of the present invention includes compounds of the formula Ip:

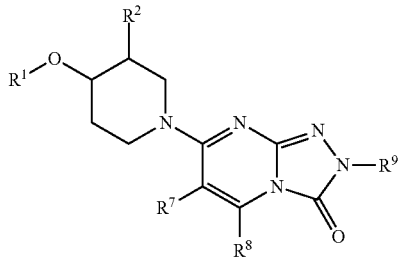

Ip wherein $R^1$, $R^2$, $R^7$, $R^8$ and $R^9$ are defined herein; or a pharmaceutically acceptable salt thereof.

An embodiment of the present invention includes compounds of the formula Iq:

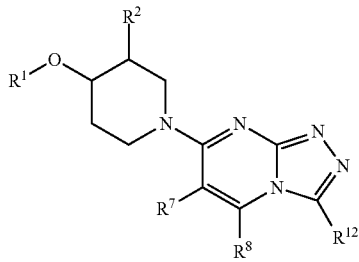

Iq wherein $R^1$, $R^2$, $R^7$, $R^8$ and $R^{12}$ are defined herein; or a pharmaceutically acceptable salt thereof.

An embodiment of the present invention includes compounds of the formula I, or a pharmaceutically acceptable salt thereof, wherein the variables —X—Y—Z— comprise a group that is selected from:

(1) —(CHR$^{10}$)(CR$^{11}$R$^{12}$)(C═O)—,
(2) —(CHR$^{10}$)(CHR$^{11}$)(CHR$^{12}$)—,
(3) —(C═O)—O—(CHR$^{12}$)—,
(4) —(C═O)(NR$^9$)(CHR$^{12}$)—,
(5) —(CHR$^{10}$)(NR$^9$)(CHR$^{12}$)—,
(6) —(CHR$^{10}$)(NR$^9$)(SO$_2$)—,
(7) —(NR$^9$)(C═O)(NR$^9$)—,
(8) —(NR$^9$)—N═(CHR$^{12}$)—,
(9) —(NR$^9$)(NH)(C═O)—, and
(10) —(CHR$^{10}$)(NR$^9$)(—N═).

An embodiment of the present invention includes compounds of the formula I, or a pharmaceutically acceptable salt thereof, wherein the group:

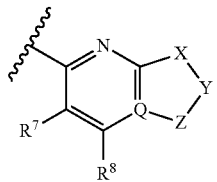

is selected from the group consisting of:

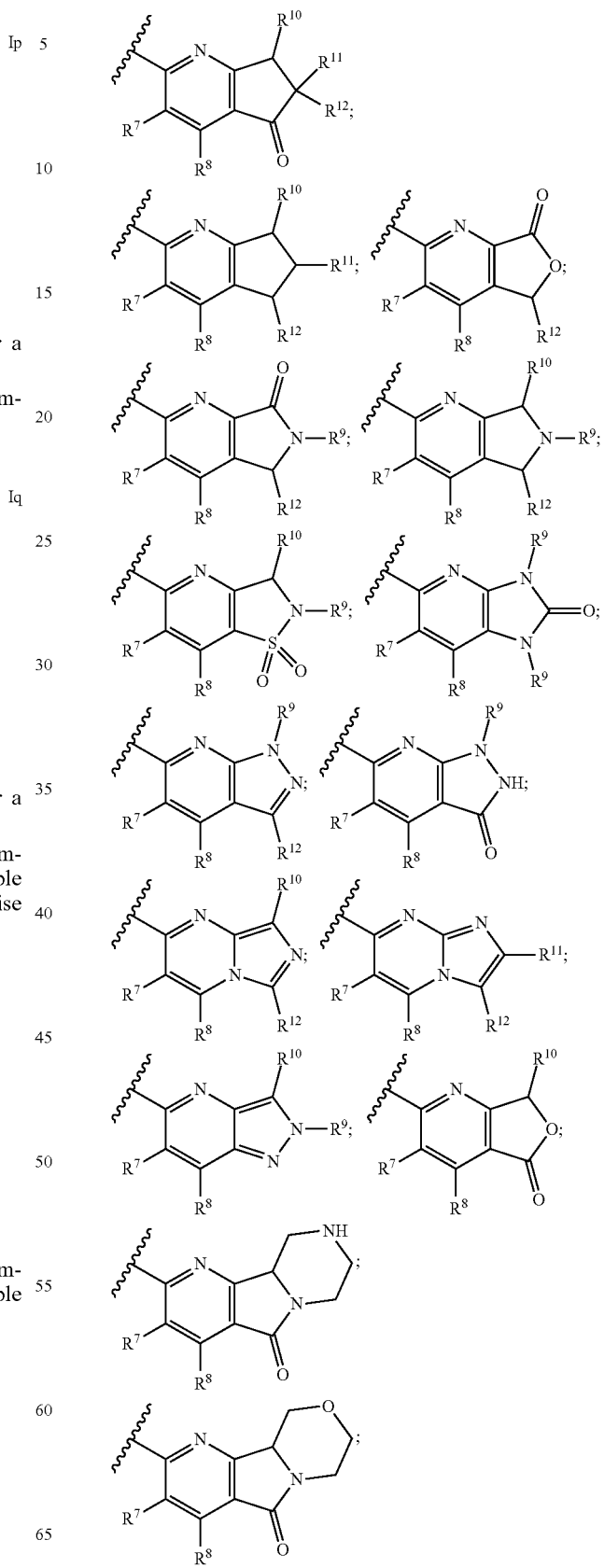

-continued

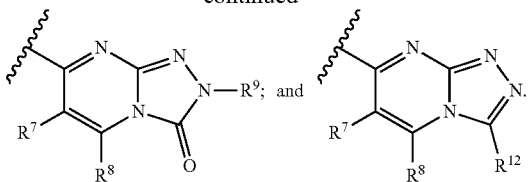

An embodiment of the present invention includes compounds wherein $R^1$ is selected from the group consisting of: benzodioxolyl, benzoimidazolyl, benzoxazolyl, benzooxazinone, benzooxazolone, benzothiazolyl, chromanyl, cyclopentapyridinyl, dihydrobenzo[1,4]dioxinyl, dihydrobenzofuranyl, dihydrobenzo[1,4]oxazinyl, dihydrofuropyridinyl, dihydroisobenzofuranyl, dihydroisoquinolinone, dihydropyranopyridinyl, dihydroimidazopyridine, dihydropyrido[1,4]oxazinyl, dihydroquinolinone, indazolyl, indanyl, indolyl, isochromanone, isobenzofuranone, isochromanyl, isoindolinyl, isoxazolyl, oxoisoindolinyl, phenyl, pyrazolopyridinyl, pyrazolyl, pyridyl, pyrrolopyridinyl, pyrimidinyl, quinolinone, quinolinyl, tetrahydrofuranyl, tetrahydroisoquinolinyl, tetrahydroquinolinyl, and tetrahydropyranyl, which is substituted with one or more of $R^{1a}$, $R^{1b}$ and $R^{1c}$.

An embodiment of the present invention includes compounds wherein $R^1$ is phenyl or pyridyl, which is substituted with $R^{1a}$, $R^{1b}$ and $R^{1c}$, wherein $R^{1a}$, $R^{1b}$ and $R^{1c}$ are independently selected from the group consisting of
(a) hydrogen,
(b) hydroxyl,
(c) halogen,
(d) $C_{1-6}$alkyl, which is unsubstituted or substituted with substituents selected from the group consisting of hydroxy, fluoro, and —$OCH_3$,
(e) —O—$C_{1-6}$alkyl, which is unsubstituted or substituted with substituents selected from the group consisting of hydroxy, fluoro, and —$OCH_3$,
(f) $C_{3-6}$cycloalkyl, which is unsubstituted or substituted with a substituent selected from the group consisting of $C_{1-6}$alkyl and hydroxy; and
(g) —CN.

An embodiment of the present invention includes compounds wherein $R^1$ is phenyl or pyridyl, which is substituted with $R^{1a}$, $R^{1b}$ and $R^{1c}$, wherein $R^{1a}$, $R^{1b}$ and $R^{1c}$ are independently selected from the group consisting of
(a) hydrogen,
(b) hydroxyl,
(c) halogen,
(d) $C_{1-3}$alkyl, which is unsubstituted or substituted with a substituent selected from the group consisting of hydroxy, 1-3 fluoro, and —$OCH_3$,
(e) —O—$C_{1-3}$alkyl, which is unsubstituted or substituted with a substituent selected from the group consisting of: 1-3 fluoro, and —$OCH_3$, and
(g) —CN.

An embodiment of the present invention includes compounds wherein $R^1$ is selected from the group consisting of:
(a) hydrogen,
(b) phenyl, which is unsubstituted or substituted with $C_{1-3}$alkyl or —CN, and
(c) pyridyl, which is unsubstituted or substituted with $C_{1-3}$alkyl or —O—$C_{1-3}$alkyl.

An embodiment of the present invention includes compounds wherein $R^1$ is phenyl, which is unsubstituted or substituted with —CN. An embodiment of the present invention includes compounds wherein $R^1$ is pyridyl, which is unsubstituted or substituted with —$OCH_3$.

An embodiment of the present invention includes compounds wherein $R^2$ and $R^3$ are each hydrogen. An embodiment of the present invention includes compounds wherein $R^2$ is fluoro and $R^3$ is hydrogen. An embodiment of the present invention includes compounds wherein $R^2$ is —$CH_3$ and $R^3$ is hydrogen. An embodiment of the present invention includes compounds wherein $R^2$ is fluoro and $R^3$ is fluoro.

An embodiment of the present invention includes compounds wherein $R^7$ is selected from the group consisting of:
(1) hydrogen,
(2) methyl,
(3) ethyl,
(4) -fluoro, and
(5) -chloro.

An embodiment of the present invention includes compounds wherein $R^7$ is —$CH_3$.

An embodiment of the present invention includes compounds wherein $R^8$ is selected from the group consisting of:
(1) hydrogen,
(2) methyl,
(3) ethyl,
(4) -fluoro, and
(5) -chloro.

An embodiment of the present invention includes compounds wherein $R^8$ is hydrogen. An embodiment of the present invention includes compounds wherein $R^8$ is —$CH_3$.

An embodiment of the present invention includes compounds wherein $R^9$ is selected from the group consisting of:
(1) hydrogen, and
(2) —$C_{1-6}$alkyl, which is unsubstituted or substituted with hydroxy, methoxy, 1-3 fluoro.

An embodiment of the present invention includes compounds wherein $R^9$ is hydrogen. An embodiment of the present invention includes compounds wherein $R^9$ is methyl. An embodiment of the present invention includes compounds wherein $R^9$ is —$CH_2CH_2OH$.

An embodiment of the present invention includes compounds wherein $R^{10}$ is hydrogen. An embodiment of the present invention includes compounds wherein $R^{10}$ is —$CH_3$. An embodiment of the present invention includes compounds wherein $R^{10}$ is —$CH_2OH$.

An embodiment of the present invention includes compounds wherein $R^{11}$ is hydrogen. An embodiment of the present invention includes compounds wherein $R^{11}$ is —$CH_3$. An embodiment of the present invention includes compounds wherein $R^{11}$ is —$CH_2OH$.

An embodiment of the present invention includes compounds wherein $R^{12}$ is hydrogen. An embodiment of the present invention includes compounds wherein $R^{12}$ is —$CH_3$. An embodiment of the present invention includes compounds wherein $R^{12}$ is —$CH_2OH$.

Certain embodiments of the present invention include a compound which is selected from the group consisting of the subject compounds of the Examples herein or a pharmaceutically acceptable salt thereof.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention.

The present invention is meant to comprehend all such isomeric forms of these compounds. Likewise, the present invention includes tautomeric forms of the compounds disclosed herein. Formula I shows the structure of the class of compounds without specific stereochemistry. At least some of the chemical names of compounds of the invention as set forth in this application may have been generated on an automated basis by use of commercially available chemical naming software programs, and have not been independently verified.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

As appreciated by those of skill in the art, halogen or halo as used herein are intended to include fluoro, chloro, bromo and iodo. Similarly, $C_{1-6}$, as in $C_{1-6}$alkyl is defined to identify the group as having 1, 2, 3, 4, 5 or 6 carbons in a linear or branched arrangement, such that $C_{1-6}$alkyl specifically includes methyl, ethyl, n-propyl, iso-propyl, n-butyl, iso-butyl, tert-butyl, pentyl, and hexyl. Likewise, —N($C_{3-6}$cycloalkyl) refers to the presence of a nitrogen-containing saturated such a pyrrolidine or piperidine. Substituents (such as $R^{1a}$, $R^{1b}$ and $R^{1c}$) may be absent if the valency of the group to which they are attached does not permit such substitution. A group which is designated as being independently substituted with substituents may be independently substituted with multiple numbers of such substituents.

The term "heteroaryl" as used herein represents a stable monocyclic, bicyclic or tricyclic ring of up to 7 atoms in each ring, wherein at least one ring is aromatic and contains carbon and from 1 to 4 heteroatoms selected from the group consisting of O, N and S. In another embodiment, the term heteroaryl refers to a monocyclic, bicyclic or tricyclic aromatic ring of 5- to 14-ring atoms of carbon and from one to four heteroatoms selected from O, N, or S. As with the definition of heterocyclyl below, "heteroaryl" is also understood to include the N-oxide derivative of any nitrogen-containing heteroaryl. In cases where the heteroaryl substituent is bicyclic and one ring is non-aromatic, in one embodiment, the attachment is via a carbon atom of the aromatic ring. Examples of heteroaryl include but are not limited to benzodioxolyl, benzofuranyl, benzofurazanyl, benzoimidazolyl, benzimidazolonyl, benzopyrazolyl, benzothiazolyl, benzotriazolyl, benzothiophenyl, benzoxazepinyl, benzooxazinonyl, benzooxazolonyl, benzoxazolyl, carbazolyl, carbolinyl, chromanyl, cinnolinyl, cyclopentapyridinyl, dihydrobenzo[1,4]dioxinyl, dihydrobenzofuranyl, dihydrobenzo[1,4]oxazinyl, dihydrofuropyridinyl, dihydroindolyl, dihydroisobenzofuranyl, dihydroisoquinolinonyl, dihydropyranopyridinyl, dihydroimidazopyridinyl, dihydropyrido[1,4]oxazinyl, dihydroquinolinone, furanyl, imidazolyl, indolinyl, indolyl, indanyl, indolazinyl, indazolyl, isobenzofuranyl, isobenzofuranonyl, isochromanonyl, isochromanyl, isoindolinyl, isoindolyl, isoxazolinyl, isoxazolyl, isoquinolyl, isothiazolyl, isoxazolyl, naphthpyridinyl, oxadiazolyl, oxazolyl, oxazolinyl, oxetanyl, oxoisoindolinyl, pyrazinyl, pyrazolopyridinyl, pyrazolyl, pyridazinyl, pyridopyridinyl, pyridazinyl, pyridyl, pyrimidinyl, pyrimidyl, pyrrolopyridinyl, pyrrolyl, quinazolinyl, quinolyl, quinoxalinyl, tetrahydrobenzooxepinyl, tetrahydroisoquinolinyl, tetrahydropyranyl, tetrahydroquinoxalinyl, tetrazolyl, tetrazolopyridyl, thiadiazolyl, thiazolyl, thienyl, triazolyl, and N-oxides thereof, and wherein the saturated heterocyclic moieties include azetidinyl, 1,4-dioxanyl, hexahydroazepinyl, piperazinyl, piperidinyl, pyridin-2-onyl, pyrrolidinyl, morpholinyl, tetrahydrofuranyl, thiomorpholinyl, and tetrahydrothienyl, and N-oxides thereof.

"Heterocyclyl" means a non-aromatic saturated monocyclic, bicyclic, tricyclic or spirocyclic ring system comprising up to 7 atoms in each ring, or contains 3 to 14, or 5 to 10 ring atoms, in which one or more of the atoms in the ring system is an element other than carbon, for example, nitrogen, oxygen, phosphor or sulfur, alone or in combination. There are no adjacent oxygen and/or sulfur atoms present in the ring system. In one embodiment, the heterocyclyls contain about 5 to about 6 ring atoms. The heterocyclyl may be fused with an aromatic aryl group such as phenyl or heterocyclenyl. The heterocyclyl is optionally bridged (i.e., forming a bicyclic moiety), for example with a methylene, ethylene or propylene bridge. The prefix aza, oxa or thia before the heterocyclyl root name means that at least a nitrogen, oxygen or sulfur atom, respectively, is present as a ring atom. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydropyran, tetrahydrothiophenyl, lactam, lactone, and the like. "Heterocyclyl" also includes heterocyclyl rings as described above wherein =O replaces two available hydrogens on the same ring carbon atom.

The present invention also includes all pharmaceutically acceptable isotopic variations of a compound of the Formula I in which one or more atoms is replaced by atoms having the same atomic number, but an atomic mass or mass number different from the atomic mass or mass number usually found in nature. Such compounds are identical to those disclosed herein, but for the fact that one or more atoms are replaced by an atom having an atomic mass or mass number different from the atomic mass or mass number usually found in nature. Examples of isotopes that can be incorporated into the compounds of the invention include isotopes of hydrogen such as $^2$H and $^3$H, carbon such as $^{11}$C, $^{13}$C and $^{14}$C, nitrogen such as $^{13}$N and $^{15}$N, oxygen such as $^{15}$O, $^{17}$O and $^{18}$O, phosphorus such as $^{32}$P, sulfur such as $^{35}$S, fluorine such as $^{18}$F, iodine such as $^{123}$I and $^{125}$I, and chlorine such as $^{36}$Cl. Certain isotopically-labelled compounds of Formula I, for example those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy. An embodiment of the present invention includes compounds that are substituted with a positron emitting isotope. An embodiment of the present invention includes compounds that are substituted with a $^{11}$C isotope. An embodiment of the present invention includes compounds that are substituted with an $^{18}$F isotope. In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of the invention can be prepared without undue experimentation by conventional techniques well known to those skilled in the art or by processes analogous to those described in the schemes and examples herein using appropriate isotopically-enriched reagents and/or intermediates.

Those skilled in the art will recognize those instances in which the compounds of the invention may form salts. In such instances, another embodiment provides pharmaceutically acceptable salts of the compounds of the invention. Thus, reference to a compound of the invention herein is understood to include reference to salts thereof, unless otherwise indicated. The term "pharmaceutically acceptable salts" refers to salts prepared from pharmaceutically acceptable non-toxic bases or acids including inorganic or organic bases and inorganic or organic acids. In addition, when a compound of the invention contains both a basic moiety, such as, but not limited to a pyridine or imidazole, and an acidic moiety, such as, but not limited to a carboxylic acid, zwitterions ("inner salts") may be formed and are included within the present invention. Salts derived from inorganic bases include aluminum, ammonium, calcium, copper, ferric, ferrous, lithium, magnesium, manganic salts, manganous, potassium, sodium, zinc, and the like. Particular embodiments include the ammonium, calcium, magnesium, potassium, and sodium salts. Salts in the solid form may exist in more than one crystal structure, and may also be in the form of hydrates or solvates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments include the citric, hydrobromic, hydrochloric, maleic, phosphoric, sulfuric, fumaric, and tartaric acids. It will be understood that, as used herein, references to the compounds of Formula I are meant to also include the pharmaceutically acceptable salts. Salts of the compounds of the invention may be formed by methods known to those of ordinary skill in the art, for example, by reacting a compound of the invention with an amount of acid or base, such as an equivalent amount, in a medium such as one in which the salt precipitates or in an aqueous medium followed by lyophilization.

Exemplifying the invention is the use of the compounds disclosed in the Examples and herein. Specific compounds within the present invention include a compound which is selected from the group consisting of the compounds disclosed in the following Examples and pharmaceutically acceptable salts thereof and individual enantiomers or diastereomers thereof.

As used herein, the term "M4 muscarinic acetylcholine receptor" refers to one of the five subtypes of the muscarinic acetylcholine receptor, which is from the superfamily of G-protein coupled receptors. The family of muscarinic receptors is described, for example, in *Pharmacol Ther,* 1993, 58:319-379; *Eur J Pharmacol,* 1996, 295:93-102, and *Mol Pharmacol,* 2002, 61:1297-1302. The muscarinic receptors are known to contain one or more allosteric sites, which may alter the affinity with which muscarinic ligands bind to the primary binding or orthosteric sites. See, e.g., S. Lazareno, et al., *Mol Pharmacol,* 2002, 62:6, 1491-1505.

As used herein, the terms "positive allosteric modulator" and "allosteric potentiator" are used interchangeably, and refer to a ligand which interacts with an allosteric site of a receptor to augment the response produced by the endogenous ligand at the orthosteric binding site. The compounds of the invention are allosteric modulators of the M4 muscarinic acetylcholine receptor, including as positive allosteric modulators of the M4 muscarinic acetylcholine receptor and silent allosteric modulators of the M4 muscarinic acetylcholine receptor. Some of the compounds of the invention are agonists of the M4 muscarinic acetylcholine receptor. Some of the compounds of the invention are allosteric modulators of the M1 muscarinic acetylcholine receptor, or may be agonists of the M1 muscarinic acetylcholine receptor. For example, a modulator or potentiator may directly or indirectly augment the response produced by the endogenous ligand (such as acetylcholine or xanomeline) at the orthosteric site of the M4 muscarinic acetylcholine receptor in an animal, in particular, a human.

The actions of ligands at allosteric receptor sites may also be understood according to the "allosteric ternary complex model," as known by those skilled in the art. The allosteric ternary complex model is described with respect to the family of muscarinic receptors in Birdsall et al, *Life Sciences,* 2001, 68:2517-2524. For a general description of the role of allosteric binding sites, see Christopoulos, *Nature Reviews: Drug Discovery,* 2002, 1:198-210.

It is believed that the compounds of the invention bind to an allosteric binding site that is distinct from the orthosteric acetylcholine site of the M4 muscarinic acetylcholine receptor, thereby augmenting the response produced by the endogenous ligand acetylcholine at the orthosteric site of the M4 muscarinic acetylcholine receptor. It is also believed that the compounds of the invention bind to an allosteric site which is distinct from the xanomeline site of the M4 muscarinic acetylcholine receptor, thereby augmenting the response produced by the endogenous ligand xanomeline at the orthosteric site of the M4 muscarinic acetylcholine receptor.

The present invention is also directed to the use of the compounds disclosed herein as modulators of M4 muscarinic acetylcholine receptor activity. The subject compounds and pharmaceutically acceptable salts thereof are useful in a method of M4 modulating muscarinic acetylcholine receptor activity in a subject such as a mammal comprising the administration of an amount of the compound. In addition to primates, especially humans, a variety of other mammals may be administered with a compound of the present invention. The present invention is directed to a compound of the present invention or a pharmaceutically acceptable salt thereof that could be useful in therapy. The present invention may further be directed to a use of a compound of the present invention or a pharmaceutically acceptable salt thereof for the manufacture of a medicament for modulating M4 muscarinic acetylcholine receptor activity or treating the disorders and diseases noted herein in humans and animals.

A subject administered with a compound of the present invention, or a pharmaceutically acceptable salt thereof, is generally a mammal, such as a human being, male or female. The amount of compound administered to the subject is an amount sufficient to modulate the M4 muscarinic acetylcholine receptor in the subject. In an embodiment, the amount of compound can be an "effective amount" or "therapeutically effective amount", wherein the subject compound or pharmaceutical composition is administered in an amount that will elicit the biological or medical response of a tissue, system, animal or human that is being sought by the researcher, veterinarian, medical doctor or other clinician, or otherwise inhibiting the noted disease and thus producing the desired therapeutic, ameliorative, inhibitory or preventative effect. An effective amount does not necessarily include considerations of toxicity and safety related to the administration of the compound. It is recognized that one skilled in the art may affect neurological and psychiatric disorders associated with M4 muscarinic acetylcholine receptor modulation by treating a subject presently afflicted with the disorders, or by prophylactically treating a subject likely to be afflicted with the disorders, with an effective amount of a compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a subject that is predisposed to such disease or disorder. The terms "administration of" and "administering" a compound should be understood to mean providing a compound of the invention or a prodrug of a compound of the invention to the subject. The term "dysfunction" refers to abnormality or impairment in the function of the noted system.

The term "composition" as used herein is intended to encompass a product comprising the specified ingredients in the specified amounts, as well as any product which results, directly or indirectly, from combination of the specified ingredients in the specified amounts. Such term is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The utility of the compounds in accordance with the present invention as modulators of M4 muscarinic acetylcholine receptors may be readily determined without undue experimentation by methodology well known in the art, including monitoring the mobilization of intracellular Ca++, determining the levels of intracellular cAMP, or quantiting the exchange of GDP for [35S]γGTP.

In a typical experiment the M4 muscarinic acetylcholine receptor modulating activity of the compounds of the present invention was determined in accordance with the following experimental method. CHO-K1 cells stably transfected with human M4 receptor and chimeric G-protein Gαqi5 (Coward P, et al., Analytical Biochemistry, 270:242-248 (1999)) are thawed from liquid $N_2$ storage, resuspended in growth medium, plated in black, clear bottom 384 well plates, and incubated 16-20 hours at 37° C., 5% $CO_2$. On the day of assay, growth medium is removed, the cells are washed 2 times with wash buffer, and cells are incubated in dye loading buffer at 37° C., 5% $CO_2$ for ~1 hour. Following dye loading the cell plates are placed in a FLIPR Tetra instrument and while monitoring dye fluorescence (excitation 470-495 nM/emission 515-575 nM), 10 uL of test substance at increasing concentrations is added, and fluorescence values are recorded for 4 min. Next, 10 uL of acetylcholine is added (final concentration calculated so as to achieve 20% of the maximum acetycholine response), and the fluorescence reading is continued for 3.5 min. In some cases, a third addition of acetylcholine (final concentration calculated to achieve 70% of the maximal acetylcholine response) is performed. The resulting dose response curves are fit to a 4 parameter logistic equation and the final result is determined as the inflection point (IP) of the curve The intrinsic M4 muscarinic acetylcholine receptor modulating activity of a compound which may be used in the present invention may be determined by these assays.

All of the final compounds of the following examples had activity in the human FLIPR-based M4 PAM assay with an IP of about 5 nM to 15000 nM against the human M4 muscarinic acetylcholine receptor. Additional data is provided in the following Examples. Such a result is indicative of the intrinsic activity of the compounds in use as a modulating the human M4 muscarinic acetylcholine receptor. In general, one of ordinary skill in the art would appreciate that a substance is considered to effectively modulate the human M4 muscarinic acetylcholine receptor if it has an IP of less than about 50 μM, or more specifically less than about 15000 nM.

The M4 muscarinic acetylcholine receptor has been implicated in a wide range of biological functions. This has suggested a potential role for these receptors in a variety of disease processes in humans or other species. The compounds of the present invention could therefore potentially have utility in treating, preventing, ameliorating, controlling or reducing the risk of a variety of neurological and psychiatric disorders associated with M4 muscarinic acetylcholine receptors, including one or more of the following conditions or diseases, and other diseases related to general M4 muscarinic acetylcholine receptor system dysfunction.

Potential conditions or disorders for which the compounds of the invention may be useful further include one or more of the following conditions or diseases: Alzheimer's disease (including mild Alzheimer's disease, moderate Alzheimer's disease and severe Alzheimer's disease), olfactory impairment associated with Alzheimer's disease, Down's syndrome, olfactory impairment associated with Down's syndrome, Parkinson's disease, olfactory impairment associated with Parkinson's disease, stroke, microgliosis brain inflammation, pre-senile dementia, senile dementia, progressive supranuclear palsy, cortical basal degeneration, β-amyloid angiopathy, cerebral amyloid angiopathy, hereditary cerebral hemorrhage, cognitive disorders (including mild cognitive impairment), glaucoma, amyloidosis, type II diabetes, diabetes-associated amyloidogenesis, scrapie, bovine spongiform encephalitis, traumatic brain injury, Creutzfeld-Jakob disease, schizophrenia, sleep disorders, pain disorders (including acute pain, inflammatory pain and neuropathic pain), pulmonary hypertension, chronic obstructive pulmonary disease (COPD), asthma, urinary incontinence, glaucoma, schizophrenia, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, pancreatitis, inclusion body myositis, other peripheral amyloidoses, diabetes, autism, atherosclerosis, tolerance and/or dependence to opioid treatment of pain, and for treatment of withdrawal syndrome of e.g., alcohol, opioids, and cocaine, Huntington's disease, drug-induced dyskinesias.

Potential conditions or disorders for which the compounds of the invention may be useful further include one or more of the following conditions or diseases: schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketamine and other dissociative anaesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Levodopa induced dyskinesia, other drug induced dyskinesia (e.g. tardive dyskinesias), Huntington's disease, Pick's disease, Creutzfeldt-Jacob disease, perinatal hypoxia, other general medical conditions or substance abuse); delirium, amnestic disorders or age related cognitive decline; delusional disorder, shared psychotic disorder, catastrophic schizophrenia, postpartum psychosis, psychotic depression, psychotic break, tardive psychosis, myxedematous psychosis, occupational psychosis, menstrual psychosis, secondary psychotic disorder, bipolar I disorder with psychotic features, and substance-induced psychotic disorder; major depressive disorder, affective disorder, bipolar disorder, electrolyte disorder, neurological disorder, hypoglycemia, AIDS, lupus, and post-traumatic stress disorder; brain tumor, dementia with Lewy bodies, multiple sclerosis, sarcoidosis, Lyme disease, syphilis, Alzheimer's disease, Parkinson's disease, and anti-NMDA receptor encephalitis. Thus, in another specific embodiment, the present invention provides a method for treating schizophrenia or psychosis comprising administering to a patient in need thereof an effective amount of a compound of the present invention. At present, the text revision of the fourth edition of the Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorder. As used herein, the term "schizophrenia or psychosis" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "schizophrenia or psychosis" is intended to include like disorders that are described in other diagnostic sources.

Potential conditions or disorders for which the compounds of the invention may be useful further include one or more of the following conditions or diseases: mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder, mood disorders due to a general medical condition, and substance-induced mood disorders; affective neurosis; depressive neurosis; anxiety neurosis; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; acute neurological and psychiatric disorders such as cerebral deficits subsequent to cardiac bypass surgery and grafting, stroke, ischemic stroke, cerebral ischemia, spinal cord trauma, head trauma, perinatal hypoxia, cardiac arrest, hypoglycemic neuronal damage; idiopathic and drug-induced Parkinson's disease; muscular spasms and disorders associated with muscular spasticity including tremors, epilepsy, convulsions, seizure disorders, absence seizures, complex partial and generalized seizures; Lennox-Gastaut syndrome; cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; dissociative disorders including multiple personality syndromes and psychogenic amnesias; substance-related disorders, substance use, substance abuse, substance seeking, substance reinstatement, all types of psychological and physical addictions and addictive behaviors, reward-related behaviors (including substance-induced delirium, persisting dementia, persisting amnestic disorder, psychotic disorder or anxiety disorder; tolerance, addictive feeding, addictive feeding behaviors, binge/purge feeding behaviors, dependence, withdrawal or relapse from substances including alcohol, amphetamines, cannabis, cocaine, hallucinogens, inhalants, morphine, nicotine, opioids, phencyclidine, sedatives, hypnotics or anxiolytics); appetite, taste, eating or drinking disorders; movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), chronic fatigue syndrome, fatigue, including Parkinson's fatigue, multiple sclerosis fatigue, fatigue caused by a sleep disorder or a circadian rhythm disorder, medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, and dyskinesias [including tremor (such as rest tremor, essential tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), restless leg syndrome and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); neurodegenerative disorders including nosological entities such as disinhibition-dementia-parkinsonism-amyotrophy complex; pallido-ponto-nigral degeneration; epilepsy; seizure disorders; attention deficit/hyperactivity disorder (ADHD); conduct disorder; migraine (including migraine headache); headache; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; emesis, nausea, vomiting; gastric dyskinesia; gastric ulcers; Kallman's syndrome (anosmia); asthma; cancer; conditions associated with visceral pain such as irritable bowel syndrome, and angina; eating disorders; urinary incontinence; substance tolerance, substance withdrawal (including, substances such as opiates, nicotine, tobacco products, alcohol, benzodiazepines, cocaine, sedatives, hypnotics, etc.); psychosis; schizophrenia; anxiety (including generalized anxiety disorder, panic disorder, and obsessive compulsive disorder); mood disorders (including depression, mania, bipolar disorders); trigeminal neuralgia; hearing loss; tinnitus; neuronal damage including ocular damage; retinopathy; macular degeneration of the eye; emesis; brain edema; pain, including acute and chronic pain states, severe pain, intractable pain, inflammatory pain, neuropathic pain, post-traumatic pain, bone and joint pain (osteoarthritis), repetitive motion pain, dental pain, cancer pain, myofascial pain (muscular injury, fibromyalgia), perioperative pain (general surgery, gynecological), chronic pain, neuropathic pain, post-traumatic pain, trigeminal neuralgia, migraine and migraine headache.

Potential sleep conditions or disorders for which the compounds of the invention may be useful include enhancing sleep quality; improving sleep quality; augmenting sleep maintenance; increasing the value which is calculated from the time that a subject sleeps divided by the time that a subject is attempting to sleep; decreasing sleep latency or onset (the time it takes to fall asleep); decreasing difficulties in falling asleep; increasing sleep continuity; decreasing the number of awakenings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; increasing daytime alertness; reducing daytime drowsiness; treating or reducing excessive daytime sleepiness; insomnia; hypersomnia; narcolepsy; interrupted sleep; sleep apnea; wakefulness; nocturnal myoclonus; REM sleep interruptions; jet-lag; shift workers' sleep disturbances; dyssomnias; night terror; insomnias associated with depression, emotional/mood disorders, as well as sleep walking and enuresis, and sleep disorders which accompany aging; Alzheimer's sundowning; conditions associated with circadian rhythmicity as well as mental and physical disorders associated with travel across time zones and with rotating shift-work schedules; conditions due to drugs which cause reductions in REM sleep as a side effect; syndromes which are manifested by non-restorative sleep and muscle pain or sleep apnea which is associated with respiratory disturbances during sleep; and conditions which result from a diminished quality of sleep.

Pain disorders for which the compounds of the invention may be useful include neuropathic pain (such as postherpetic neuralgia, nerve injury, the "dynias", e.g., vulvodynia, phantom limb pain, root avulsions, painful diabetic neuropathy, painful traumatic mononeuropathy, painful polyneuropathy); central pain syndromes (potentially caused by virtually any lesion at any level of the nervous system); postsurgical pain syndromes (e.g., postmastectomy syndrome, postthoracotomy syndrome, stump pain); bone and joint pain (osteoarthritis), repetitive motion pain, dental pain, cancer pain, myofascial pain (muscular injury, fibromyalgia); perioperative pain (general surgery, gynecological), chronic pain, dysmennorhea, as well as pain associated with angina, and inflammatory pain of varied origins (e.g. osteoarthritis, rheumatoid arthritis, rheumatic disease, teno-synovitis and gout), headache, migraine and cluster headache, headache, primary hyperalgesia, secondary hyperalgesia, primary allodynia, secondary allodynia, or other pain caused by central sensitization.

The subject compounds could further be of potential use in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to subjects (animals and human) in need of such treatment in dosages that will provide optimal pharmaceutical efficacy. The selected dosage depends upon the desired therapeutic effect, on the route of administration, and on the duration of the treatment. The dose will vary from subject to subject depending upon the nature and severity of disease, the subject's weight, special diets then being followed by a subject, concurrent medication, and other factors which those skilled in the art will recognize. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Generally, dosage levels of between 0.0001 to 10 mg/kg of body weight daily are administered to the subject, e.g., humans and elderly humans, to obtain effective modulation of M4 muscarinic acetylcholine receptors. The dosage range will generally be about 0.5 mg to 1.0 g per subject per day which may be administered in single or multiple doses. In one embodiment, the dosage range will be about 0.5 mg to 500 mg per subject per day; in another embodiment about 0.5 mg to 200 mg per subject per day; and in yet another embodiment about 5 mg to 50 mg per subject per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 30 mg, 50 mg, 80 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the subject to be treated. The compounds may be administered on a regimen of 1 to 4 times per day, such as once or twice per day. The compounds may be administered before bedtime. For example, the compounds may be administered about 1 hour prior to bedtime, about 30 minutes prior to bedtime or immediately before bedtime.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is contemplated. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is contemplated. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The compounds of the present invention may be used in combination with one or more other drugs in the treatment of diseases or conditions for which the compounds of the present invention have utility, where the combination of the drugs together are safer or more effective than either drug alone. In a embodiment, the subject compound may be employed in combination with other compounds which are known in the art, either administered separately or in the same pharmaceutical compositions, including, but are not limited to: anti-Alzheimer's agents; beta-secretase inhibitors, such as verubecestat; alpha 7 nicotinic agonists, such as ABT089, SSR180711 and MEM63908; HT2a modulators, such as pimavaserin; ADAM 10 ligands or activators; gamma-secretase inhibitors, such as LY450139 and TAK 070; gamma-secretase inhibitors; gamma secretase modulators; tau phosphorylation inhibitors; glycine transport inhibitors; LXR β agonists; ApoE4 conformational modulators; NR2B antagonists; androgen receptor modulators; blockers of Aβ oligomer formation; 5-HT4 agonists, such as PRX-03140; 5-HT6 antagonists, such as GSK 742467, SGS-518, FK-962, SL-65.0155, SRA-333 and xaliproden; 5-HT1a antagonists, such as lecozotan; p25/CDK5 inhibitors; NK1/NK3 receptor antagonists; COX-2 inhibitors; HMG-CoA reductase inhibitors; NSAID's including ibuprofen; vitamin E; anti-amyloid antibodies (including anti-amyloid humanized monoclonal antibodies), such as bapineuzumab, ACC001, CAD106, AZD3102, H12A11V1; anti-inflammatory compounds such as (R)-flurbiprofen, nitroflurbiprofen, ND-1251, VP-025, HT-0712 and EHT-202; PPAR gamma agonists, such as pioglitazone and rosiglitazone; CB-1 receptor antagonists or CB-1 receptor inverse agonists, such as AVE-1625; antibiotics such as doxycycline and rifampin; CB-1 receptor antagonists or CB-1 receptor inverse agonists; antibiotics such as doxycycline and rifampin; N-methyl-D-aspartate (NMDA) receptor antagonists, such as memantine, neramexane and EVT101; recombinant growth hormone; growth hormone secretagogues such as ibutamoren, ibutamoren mesylate, and capromorelin; histamine H3 receptor antagonists such as ABT-834, ABT 829, GSK 189254 and CEP16795; AMPA agonists or AMPA modulators, such as CX-717, LY 451395, LY404187 and S-18986; neuronal nicotinic agonists; muscarinic antagonists (e.g., M1 agonists (such as acetylcholine, oxotremorine, carbachol, or McNa343), or M$_2$ antagonists (such as atropine, dicycloverine, tolterodine, oxybutynin, ipratropium, methoctramine, tripitamine, or gallamine)); cholinesterase inhibitors (e.g., acetyl- and/or butyrylchlolinesterase inhibitors such as donepezil (Aricept®, (±)-2,3-dihydro-5,6-dimethoxy-2-[[1-(phenylmethyl)-4-piperidinyl]methyl]-1H-inden-1-one hydrochloride), tacrine, phenserine, ladostigil, ABT-089, galantamine (Razadyne®), and rivastigimine (Exelon®); N-methyl-D-aspartate receptor antagonists (e.g., Namenda® (memantine HCl, available from Forrest Pharmaceuticals, Inc.); combinations of cholinesterase inhibitors and N-methyl-D-aspartate receptor antagonists; anti-inflammatory agents that can reduce neuroinflammation; glycogen synthase kinase beta inhibitors; promoters of alpha secretase activity; PDE IV inhibitors, including MEM1414, HT0712 and AVE8112; PDE-10 inhibitors; Tau kinase inhibitors (e.g., GSK3beta inhibitors, cdk5 inhibitors, or ERK inhibitors); GSK3β inhibitors, including AZD1080, SAR502250 and CEP16805; neuronal nicotinic agonists; selective M1 agonists; HDAC inhibitors; and microtubule affinity regulating kinase (MARK) ligands; Tau aggregation inhibitors (e.g., Rember®); RAGE inhibitors (e.g., TTP 488 (PF-4494700)); anti-Abeta vaccine; APP ligands; agents that upregulate insulin, cholesterol lowering agents such as HMG-CoA reductase inhibitors (for example, statins such as Atorvastatin, Fluvastatin, Lovastatin, Mevastatin, Pitavastatin, Pravastatin, Rosuvastatin, Simvastatin) and/or cholesterol absorption inhibitors (such as Ezetimibe), or combinations of HMG-CoA reductase inhibitors and cholesterol absorption inhibitors (such as, for example, Vytorin®); fibrates (such as, for example, clofibrate, Clofibride, Etofibrate, and Aluminium Clofibrate); combinations of fibrates and cholesterol lowering agents and/or cholesterol absorption inhibitors; nicotinic receptor agonists; niacin; combinations of niacin and cholesterol absorption inhibitors and/or cholesterol lowering agents (e.g., Simcor® (niacin/simvastatin, available from Abbott Laboratories, Inc.); LXR agonists; LRP mimics; H3 receptor antagonists; histone deacetylase inhibitors; hsp90 inhibitors; 5-HT4 agonists (e.g., PRX-03140 (Epix Pharmaceuticals)); 5-HT6 receptor antagonists; mGluR1 receptor modulators or antagonists; mGluR5 receptor modulators or antagonists; mGluR2/3 antagonists; Prostaglandin EP2 receptor antagonists; PAI-1 inhibitors; agents that can induce Abeta efflux such as gelsolin; Metal-protein attenuating compound (e.g., PBT2); and GPR3 modulators; and antihistamines such as Dimebolin (e.g., Dimebon®, Pfizer); or other drugs that affect receptors or enzymes that either increase the efficacy, safety, convenience, or reduce unwanted side effects or toxicity of the compounds of the present invention.

Examples of combinations of the compounds include combinations with agents for the treatment of schizophrenia, for example in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, aiprazolam, amisulpride, amitriptyline, amobarbital, amoxapine, aripiprazole, bentazepam, benzoctamine, brotizolam, bupropion, busprione, butabarbital, butalbital, capuride, carboclo- ral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproelone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisuipride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, frihexyphenidyl, thioridazine, thiothixene, trifluoperazine or ziprasidone.

Examples of combinations of the compounds include combinations with agents for the treatment of pain, for example non-steroidal anti-inflammatory agents, such as aspirin, diclofenac, duflunisal, fenoprofen, flurbiprofen, ibuprofen, indomethacin, ketoprofen, ketorolac, naproxen, oxaprozin, piroxicam, sulindac and tolmetin; COX-2 inhibitors, such as celecoxib, rofecoxib, valdecoxib, 406381 and 644784; CB-2 agonists, such as 842166 and SAB378; VR-1 antagonists, such as AMG517, 705498, 782443, PAC20030, V114380 and A425619; bradykinin B 1 receptor antagonists, such as SSR240612 and NVPSAA164; sodium channel blockers and antagonists, such as VX409 and SPI860; nitric oxide synthase (NOS) inhibitors (including iNOS and nNOS inhibitors), such as SD6010 and 274150; glycine site antagonists, including lacosamide; neuronal nicotinic agonists, such as ABT 894; NMDA antagonists, such as AZD4282; potassium channel openers; AMPA/kainate receptor antagonists; calcium channel blockers, such as ziconotide and NMED160; GABA-A receptor IO modulators (e.g., a GABA-A receptor agonist); matrix metalloprotease (MMP) inhibitors; thrombolytic agents; opioid analgesics such as codeine, fentanyl, hydromorphone, levorphanol, meperidine, methadone, morphine, oxycodone, oxymorphone, pentazocine, propoxyphene; neutrophil inhibitory factor (NIF); pramipexole, ropinirole; anticholinergics; amantadine; monoamine oxidase B15 ("MAO-B") inhibitors; 5HT receptor agonists or antagonists; mGlu5 antagonists, such as AZD9272; alpha agonists, such as AGNXX/YY; neuronal nicotinic agonists, such as ABT894; NMDA receptor agonists or antagonists, such as AZD4282; NKI antagonists; selective serotonin reuptake inhibitors ("SSRI") and/or selective serotonin and norepinephrine reuptake inhibitors ("SSNRI"), such as duloxetine; tricyclic antidepressant drugs, norepinephrine modulators; lithium; valproate; gabapentin; pregabalin; rizatriptan; zolmitriptan; naratriptan and sumatriptan.

The compounds of the present invention may be administered in combination with compounds useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, orexin antagonists, alpha-1 antagonists, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, orexin antagonists, orexin agonists, prokineticin agonists and antagonists, pyrazolopyrimidines, T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, filorexant, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, suvorexant, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. The subject or patient to whom the compounds of the present invention is administered is generally a human being, male or female, but may also encompass other mammals, such as dogs, cats, mice, rats, cattle, horses, sheep, rabbits, monkeys, chimpanzees or other apes or primates, for which treatment of the above noted disorders is desired.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives. Pharmaceutical compositions of the present compounds may be in the form of a sterile injectable aqueous or oleagenous suspension. Pharmaceutical compositions of the present compounds in the form of a sterile injectable aqueous or oleagenous suspension may be formulated by known techniques for depo administration and thereby provide a sustained action over a longer period. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

Several methods for preparing the compounds of this invention are illustrated in the following Schemes and Examples. Starting materials are made according to procedures known in the art or as illustrated herein. The following abbreviations are used herein: Me: methyl; Et: ethyl; t-Bu: tert-butyl; Ar: aryl; Ph: phenyl; aq: aqueous; BINAP: 2,2'-bis(diphenylphosphino)-1,1'-binaphthyl; Bn: benzyl; Ac: acetyl; Boc: tert-butyloxy carbonyl; BSA: bovine serum albumin; CAN: acetonitrile; Cbz: carboxylbenzyl; CbzCl: benzylchloroformate; CDI: carbonyl diimidazole; DABCO: 1,4-diazabicyclo[2.2.2]octane; DAST: diethylaminosulfur trifluoride; DBAD: di-tert-butyl azodicarboxylate; DCM: dichloromethane; DCE: dichloroethane; DEA: diethylamine; DEAD: diethylazodicarboxylate; DIAD: diisopropyl azodicarboxylate; DIBAL: diisobutylaluminium hydride; DIPEA: N,N-diisopropylethylamine; DMAP: 4-dimethylaminopyridine; DMF: N,N-dimethylformamide; DMP: Dess-Martin periodinane; DMS: dimethylsulfide; DMSO: dimethylsulfoxide; dppf: 1,1'-bis(diphenyl-phosphino)ferrocene; CH2Cl2: dichloromethane; EDC: N-(3-Dimethylaminopropyl)-N'-ethylcarbodiimide; Et3N: triethylamine; EtOAc: ethyl acetate; EtOH: ethanol; F-TEDA: Selectfluor®; HATU: (1-[bis(dimethylamino)methylene]-1H-1,2,3-triazolo[4,5-b]pyridinium 3-oxid hexafluorophosphate); HCl: hydrogen chloride; HOAt: 1-hydroxy-7-aza-benzotriazole; HOBT: hydroxybenzotriazole hydrate; HPLC: high performance liquid chromatography; Hunig's base: N,N-diisopropylethylamine; LDA: diisopropylamine; LHMDS: lithium bis(trimethylsilyl)amide; mCPBA: meta-chloroperbenzoic acid; MeOH: methanol; MgSO4: magnesium sulfate; Ms: methanesulfonyl; MTBE: methyl tert-butyl ether; MS: Mass spectra; NaHCO3: sodium bicarbonate; NaOH: sodium hydroxide; NBS: N-bromosuccinimide; NCS: N-chlorosuccinimide; NMM: N-methylmorpholine; NMR: nuclear magnetic resonance; PG: protecting group; PtO2: platinum oxide; PCC: pyridinium chlorochromate; rt: room temperature; SEM: 2-(Trimethylsilyl)ethoxy]methyl; SFC: supercritical fluid chromatography; SOCl2: thionyl chloride; T3P: 2,4,6-tripropyl-1,3,5,2,4,6-trioxatriphosphorinane-2,4,6-trioxide; TBAF: tetra-n-butylammonium fluoride; TBS: tert-Butyldimethylsilyl; TEA: triethylamine; TES: Triethylsilyl; TFA: trifluoroacetic acid; Tf: triflate; TFAA: trifluoroacetic anhydride; THF: tetrahydrofuran; TIPS: tri-isopropylsilyl; TLC: thin layer chromatography; Ts: toluenesulfonyl; X-Phos: 2-(dicyclohexyl-phosphino)-2',4',6'-triisopropyl-biphenyl.

The compounds of the present invention can be prepared in a variety of fashions. In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. Because the schemes are an illustration, the invention should not be construed as being limited by the chemical reactions and conditions expressed. The preparation of the various starting materials used herein is well within the skill of a person versed in the art. The following examples are provided so that the invention might be more fully understood. These examples are illustrative only and should not be construed as limiting the invention in any way. Absolute stereochemistry of separate stereoisomers in the examples and intermediates are not determined unless stated otherwise in an example or explicitly in the nomenclature.

SCHEME A

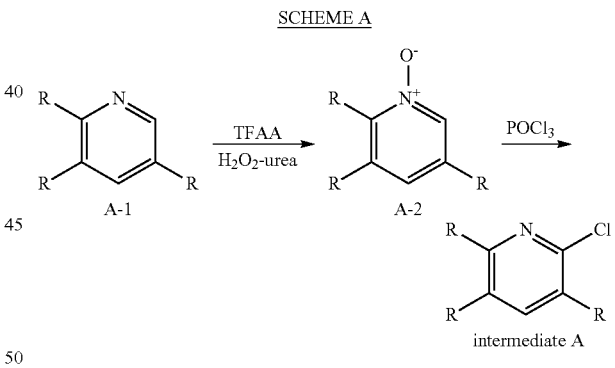

Intermediate A is prepared according to Scheme A via oxidation of commercially available pyridine A-1 with 2,2,2-trifluoroacetic anhydride to yield N-oxide A-2 and subsequent reaction with POCl3.

Intermediate A1

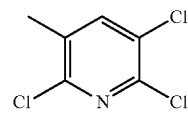

2,6-Dichloro-5-methylnicotinonitrile (Scheme A)
Step 1: 2-Chloro-5-cyano-3-methylpyridine 1-oxide To a solution of urea hydrogen peroxide (3.70 g, 39.3 mmol) in DCM (10 mL) was added TFAA (5.55 mL, 39.3 mmol) dropwise at 0° C. The mixture was stirred 15 min before the addition of 6-chloro-5-methylnicotinonitrile (1 g, 6.55 mmol). The system was then heated to 40° C. for 2 h. The reaction mixture was quenched with saturated, aqueous NaHCO$_3$ (20 mL) to pH~8 and extracted with DCM (30 mL×3), dried over anhydrous sodium sulfate, filtered and concentrated. The residue was purified by silica gel chromatography (10-50% EtOAc/petroleum ether) to give the title compound.

Step 2: 2,6-Dichloro-5-methylnicotinonitrile

A mixture of 2-chloro-5-cyano-3-methylpyridine 1-oxide (400 mg, 2.37 mmol) and POCl$_3$ (2.21 mL, 23.7 mmol) was stirred at 25° C. for 16 h and then at 90° C. for 3 h. The reaction mixture was poured into ice water (20 mL) slowly and the pH was adjusted using solid Na$_2$CO$_3$ to pH~8. The mixture was extracted with DCM (20 mL×3) and the combined organic layers were washed with brine (20 mL), dried over anhydrous sodium sulfate, filtered and concentrated. The residue was purified by silica gel chromatography (15-50% EtOAc/petroleum ether) to provide the title compound. $^1$H NMR (400 MHz, CDCl$_3$): δ 7.28 (s, 1H), 2.41 (s, 3H).

The following intermediates in table A were prepared according to scheme A using the procedure outlined in the synthesis of intermediate A1 using commercial or prepared pyridines in step 1.

TABLE A

| Intermediate | Structure | Name | MS (M + 1) |
|---|---|---|---|
| A2 | 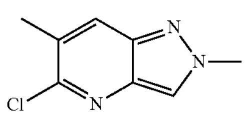 | 5-chloro-2,6-dimethyl-2H-pyrazolo[4,3-b]pyridine | 182 |
| A3 | 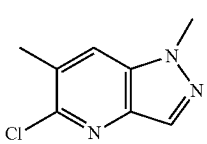 | 5-chloro-1,6-dimethyl-1H-pyrazolo[4,3-b]pyridine | 182 |

SCHEME B

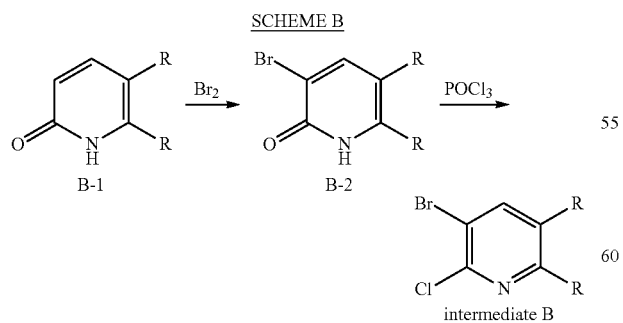

Intermediate B is prepared according to Scheme B from a commercial or known pyridone via an electrophilic bromination and subsequent reaction with phosphoryl chloride.

Intermediate B

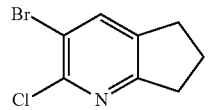

3-Bromo-2-chloro-6,7-dihydro-5H-cyclopenta[b]pyridine (Scheme B)

Step 1: 3-Bromo-2-chloro-6,7-dihydro-5H-cyclopenta[b]pyridine

To a pre-dried 100 mL round bottom flask charged with 6,7-dihydro-5H-cyclopenta[b]pyridin-2-ol (3 g, 15.54 mmol) and acetic acid (20 mL) was added solution of bromine (0.880 mL, 17.09 mmol) in acetic acid (10 mL) at 0° C. The mixture was stirred for 12 h at 15° C. The reaction was concentrated in vacuo and the residue was quenched with saturated aqueous sodium thiosulfate (200 mL) and neutralized with aqueous saturated sodium carbonate solution. The mixture was extracted with EtOAc (200 mL×4), dried over with anhydrous sodium sulfate, filtered and the filtrate was concentrated in vacuo and was purified by silica gel chromatography (1:10 MeOH:EtOAc) to give the title compound. MS: 214, 216 (M+1).

Step 2: 3-Bromo-2-chloro-6,7-dihydro-5H-cyclopenta[b]pyridine

To a solution of 3-bromo-6,7-dihydro-5H-cyclopenta[b]pyridin-2-ol (2 g, 9.34 mmol) in POCl$_3$ (5 mL) was stirred at 90° C. for 15 h. The volatiles were evaporated under reduced pressure and aqueous saturated sodium carbonate (20 mL) was added to the residue. The mixture was extracted with DCM (10 mL×3) and the combined organic fractions were washed with water (20 mL×3), dried over anhydrous sodium sulfate, filtered and concentrated. The residue was purified by silica gel chromatography (0-40% THF/petroleum ether) to give the title compound. MS: 232, 234 (M+1).

SCHEME C

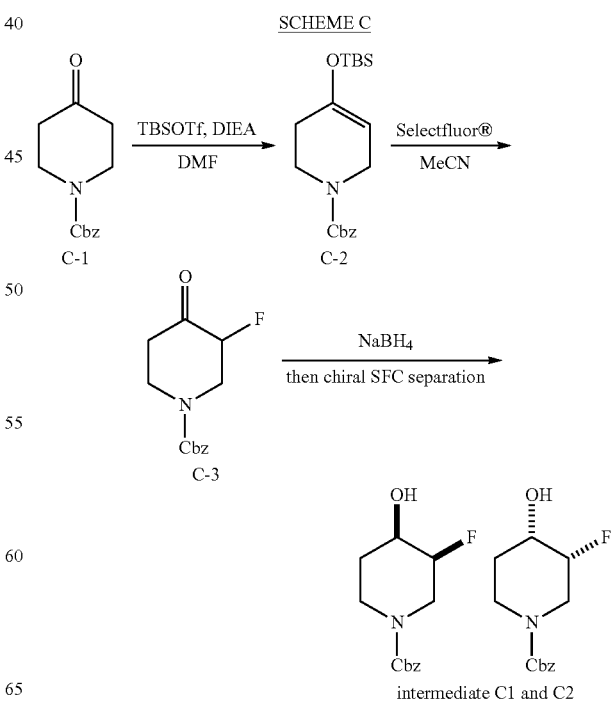

intermediate C1 and C2

Intermediate C is prepared from protected piperidone C-1 which was converted to the enol silane C-2 under the action of TBSOTf in the presence of base. Electrophilic fluorination by Selectfluor® on C-2 provided the corresponding alpha-fluorinated product C-3. Reduction by sodium borohydride and subsequent chiral SFC separation provided intermediate C1 and intermediate C2 as single enantiomers.

Intermediate C1 and C2

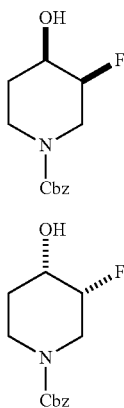

intermediate C1 intermediate C2

Benzyl (3S,4R)-3-fluoro-4-hydroxypiperidine-1-carboxylate and benzyl (3R,4S)-3-fluoro-4-hydroxypiperidine-1-carboxylate (Scheme C)

Step 1: Benzyl 4-((tert-butyldimethylsilyl)oxy)-3,6-dihydropyridine-1(2H)-carboxylate To a solution of benzyl 4-oxopiperidine-1-carboxylate (260 g, 1.11 mmol) in DMF (700 mL) was added DIPEA (216 g, 1.67 mol) and TBSOTf (83 g, 1.45 mol) at RT under an atmosphere of nitrogen. The reaction mixture was stirred for 16 h. After diluting with water (1.5 L) and extracting with EtOAc (1.5 L×3), the organic layers were combined and washed with brine (2 L×3) and concentrated. The residue was purified by silica gel column chromatography (50:1-20:1 petroleum ether:ethyl acetate) to obtain the title compound.

Step 2: Benzyl 3-fluoro-4-oxopiperidine-1-carboxylate

To a solution of benzyl 4-((tert-butyldimethylsilyl)oxy)-3,6-dihydropyridine-1(2H)-carboxylate (200 g, 0.58 mol) in MeCN (1.6 L) was added Selectfluor® (224 g, 0.63 mol) at 25° C. The reaction mixture was stirred for 10 h. The volatiles were removed under reduced pressure and the residue was diluted with EtOAc (2 L) and then washed with brine (1.5 L×3). The organic was concentrated in vacuo to give the title compound which was carried forward without further purification.

Step 3: Benzyl (3S,4R)-3-fluoro-4-hydroxypiperidine-1-carboxylate and benzyl (3R,4S)-3-fluoro-4-hydroxypiperidine-1-carboxylate To a solution of benzyl 3-fluoro-4-oxopiperidine-1-carboxylate (300 g, 1.19 mol) in MeOH (2.5 L) was added NaBH₄ (50 g, 1.31 mol) at 0° C. After stirring for 4 h at RT, the volatiles were removed under reduced pressure and the residue was diluted with EtOAc (2 L) and washed with water (2 L) and then brine (2 L×2). The organic was concentrated in vacuo and was purified on silica gel by column chromatography (10:1-2:1 petroleum ether:EtOAc) to obtain the racemic product. The material was then purified by chiral SFC (AD column, 30%/70% EtOH with 0.1% ammonium hydroxide modifier/CO₂) to afford intermediate C1 (faster eluting 3S,4R isomer): MS: 254 (M+1). ¹H NMR (400 MHz, CDCl₃): δ 7.41-7.29 (m, 1H), 5.15 (s, 1H), 4.74-4.52 (m, 1H), 4.11-3.76 (m, 3H), 3.62-3.17 (m, 2H), 2.07 (br s, 1H), 1.93-1.70 (m, 2H). Intermediate C2 (slower eluting 3R,4S isomer): MS: 254 (M+1). ¹H NMR (400 MHz, CDCl₃): δ 7.40-7.30 (m, 5H), 5.15 (s, 2H), 4.75-4.51 (m, 1H), 4.09-3.69 (m, 3H), 3.62-3.18 (m, 2H), 2.08 (br s, 1H), 1.93-1.71 (m, 2H).

SCHEME D

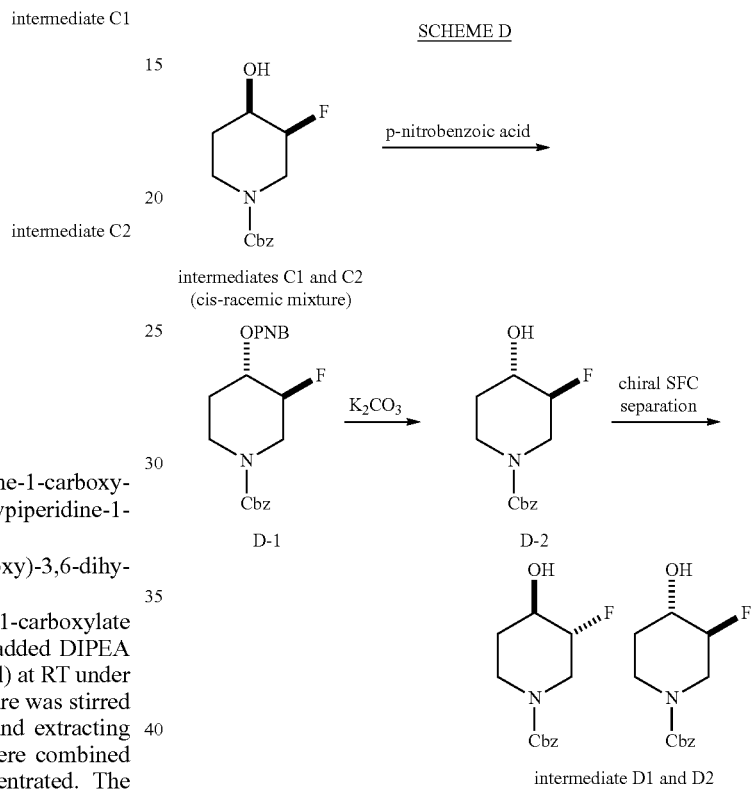

Intermediate D is prepared from a racemic mixture of intermediate C1 and intermediate C2 which is carried through a Mitsunobu reaction with p-nitrobenzoic acid to provide trans-racemic adduct D-1. Subsequent saponification reveals alcohol D-2. Chiral separation to resolve the enantiomers is carried out to provide intermediate D1 and intermediate D2 as single enantiomers.

Intermediate D1 and D2

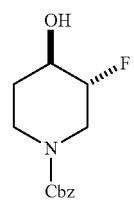

intermediate D1

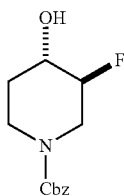

intermediate D2

Benzyl (3R,4R)-3-fluoro-4-hydroxypiperidine-1-carboxylate and benzyl (3S,4S)-3-fluoro-4-hydroxypiperidine-1-carboxylate (Scheme D)

Step 1: Benzyl trans-3-fluoro-4-((4-nitrobenzoyl)oxy)piperidine-1-carboxylate

To a stirred solution of benzyl cis-3-fluoro-4-hydroxypiperidine-1-carboxylate (60 g, 0.24 mol, intermediate C1 and C2) in THF (400 mL) was added p-nitrobenzoic acid (60 g, 0.36 mol) and Ph$_3$P (92 g, 0.35 mol) at RT. After cooling the mixture to ~0-5° C., DIAD (78 g, 0.39 mol) was added dropwise. The reaction was stirred 15 h at RT and was quenched with an aqueous, saturated NH$_4$Cl solution (600 mL) and was then extracted with EtOAc (500 mL×3). The combined organic layers were washed with brine (1 L), dried over anhydrous sodium sulfate and concentrated under reduced pressure. The residue was purified on silica gel by column chromatography (10:1 petroleum ether:EtOAc) to yield the title compound.

Step 2: Benzyl trans-3-fluoro-4-hydroxypiperidine-1-carboxylate

To a solution of benzyl cis-3-fluoro-4-((4-nitrobenzoyl)oxy)piperidine-1-carboxylate (90 g, 0.22 mol) in MeOH (900 mL) was added potassium carbonate (90 g, 0.65 mol). The resulting mixture was stirred at RT for 15 h and then the volatiles were removed under reduced pressure. The residue was partitioned between EtOAc (200 mL) and saturated, aqueous NH$_4$Cl (200 mL). The aqueous layer was extracted with EtOAc (200 mL×2) and the combined organic layers were washed with brine (500 mL), dried over anhydrous sodium sulfate, filtered and concentrated. The residue was purified by silica gel column chromatography (1:1 petroleum ether:EtOAc) to afford the title compound.

Step 3: Benzyl (3R,4R)-3-fluoro-4-hydroxypiperidine-1-carboxylate and benzyl (3S,4S)-3-fluoro-4-hydroxypiperidine-1-carboxylate Benzyl trans-3-fluoro-4-hydroxypiperidine-1-carboxylate was resolved into single enantiomers via chiral SFC (AD column, 5-40% EtOH with 0.05% diethylamine modifier/CO$_2$) to afford intermediate D1 (faster eluting 3R,4R isomer): MS: 254 (M+1). $^1$H NMR (400 MHz, CDCl$_3$): δ 7.31-7.56 (m, 5H), 5.19 (s, 2H), 4.17-4.37 (m, 2H), 3.84-3.95 (m, 2H), 3.06-3.28 (m, 2H), 2.28 (s, 1H), 2.01 (s, 1H), 1.57 (s, 1H). Intermediate D2 (slower eluting 3S,4S isomer): MS: 254 (M+1). $^1$H NMR (400 MHz, CDCl$_3$): δ 7.31-7.56 (m, 5H), 5.19 (s, 2H), 4.17-4.37 (m, 2H), 3.84-3.95 (m, 2H), 3.06-3.28 (m, 2H), 2.28 (s, 1H), 2.01 (s, 1H), 1.57 (s, 1H).

SCHEME E

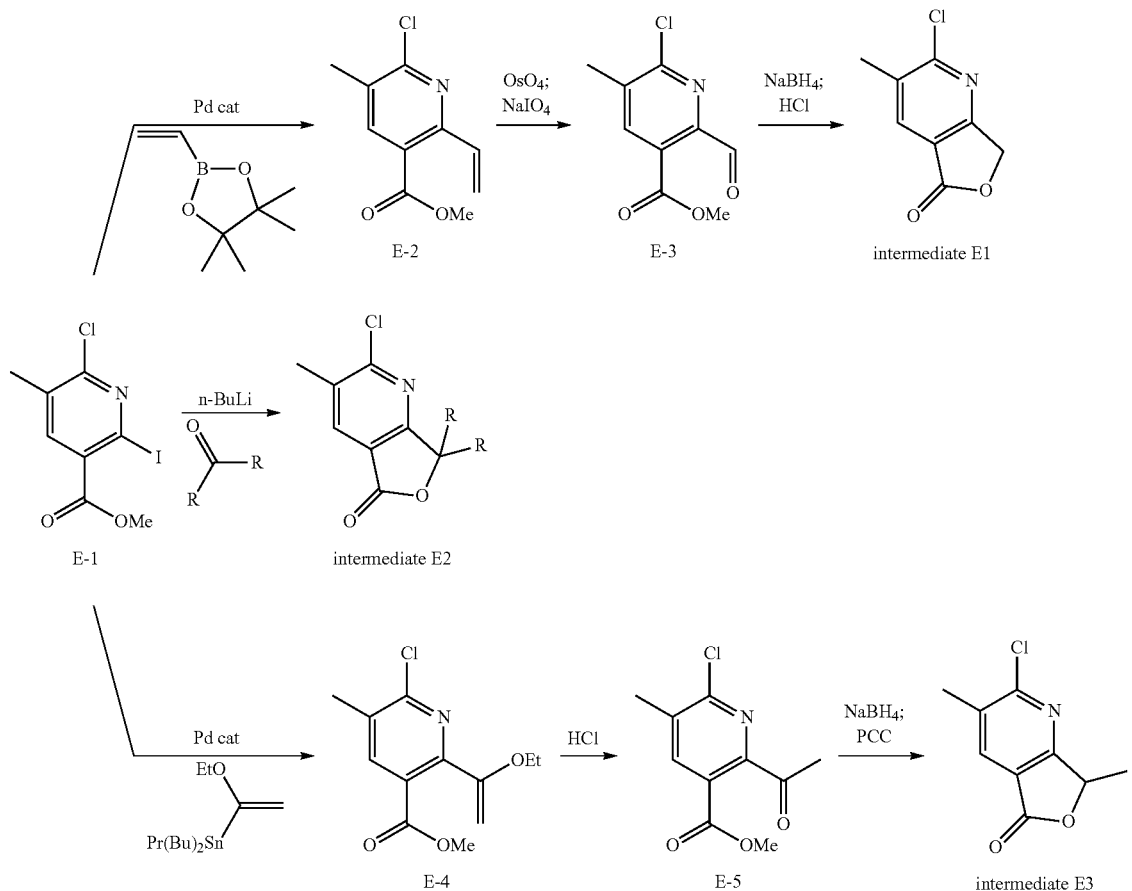

Intermediate E is prepared according to scheme E from methyl 6-chloro-2-iodo-5-methylnicotinate (prepared according to literature procedure, see e.g.: Vanlaer, S., et al. *Eur. J Org. Chem.* 2008, 15, 2571-2581). An initial palladium-mediated Suzuki coupling reaction with vinyl boronic ester furnishes alkene adduct E-2. A one-pot dihydroxylation followed by periodate cleavage yields aldehyde E-3. Aldehyde reduction leads to the corresponding alcohol which cyclizes to for intermediate E1. Alternatively, lithium halogen exchange and reaction with a ketone provides an intermediary tertiary alcohol which cyclizes to form intermediate E2. Lastly, palladium-mediated Stille reaction provides ethoxy enol E-4 which is then hydrolyzed in the presence of acid to form ketone E-5. Reduction to the diol and oxidation provides intermediate E3.

Intermediate E1

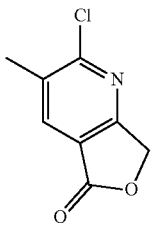

2-Chloro-3-methylfuro[3,4-b]pyridin-5(7H)-one (Scheme E)
Step 1: Methyl 6-chloro-5-methyl-2-vinylnicotinate
To a solution of methyl 6-chloro-2-iodo-5-methylnicotinate (500 mg, 1.61 mmol), 4,4,5,5-tetramethyl-2-vinyl-1,3,2-dioxaborolane (247 mg, 1.605 mmol) and K$_2$CO$_3$ (555 mg, 4.01 mmol) in THF (10 mL) and water (2 mL) was added PdCl$_2$(dppf) (117 mg, 0.161 mmol) at 18° C. The resulting mixture was stirred at 40° C. for 16 h under a nitrogen atmosphere. After cooling to RT, the reaction was diluted with water (30 mL) and extracted with EtOAc (30 mL×3). The combined organic layers were washed with brine (20 mL), dried over anhydrous sodium sulfate, filtered, and concentrated in vacuo. The residue was purified by silica gel chromatography (10:1 petroleum ether: EtOAc) to give the title compound.
Step 2: Methyl 6-chloro-2-formyl-5-methylnicotinate
To a solution of methyl 6-chloro-5-methyl-2-vinylnicotinate (230 mg, 1.09 mmol) in THF (9 mL) was added osmium tetroxide (1.02 mL, 3.26 mmol) in water (3 mL). The reaction was stirred for 1 h at 17° C., then sodium periodate (697 mg, 3.26 mmol) was added. The resulting mixture was stirred at 17° C. for 16 h before being diluted with water (20 mL) and extracted with EtOAc (10 mL×3). The combined organic layers were washed with brine (20 mL), dried over anhydrous sodium sulfate, filtered, and concentrated in vacuum. The residue was purified by silica gel chromatography (100:1-3:1 petroleum ether:EtOAc) to give the title compound.
Step 3: 2-Chloro-3-methylfuro[3,4-b]pyridin-5(7H)-one
To a solution of methyl 6-chloro-2-formyl-5-methylnicotinate (90 mg, 0.421 mmol) in THF (2 mL) was added NaBH$_4$ (6.38 mg, 0.169 mmol) at −40° C. The reaction was stirred at −40° C. for 0.5 h before being diluted with water (10 mL) and extracted with EtOAc (10 mL×3). HCl (4 M in EtOAc, 0.2 mL) was added to the combined organic layers and the mixture was stirred for 1 h at 30° C. The mixture was washed with brine (20 mL), dried over anhydrous sodium sulfate, filtered, and concentrated in vacuo. The residue was purified by silica chromatography (100:1-3:1 petroleum ether:EtOAc) to give the title compound. MS: 184 (M+1).

Intermediate E2

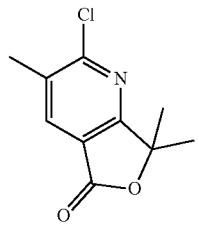

2-Chloro-3,7,7-trimethylfuro[3,4-b]pyridin-5(7H)-one (Scheme E)
To a solution of 6-chloro-2-iodo-5-methylnicotinic acid (80 mg, 0.269 mmol) in THF (3 mL) was added n-butyllithium (0.430 mL, 1.076 mmol) at −78° C. and stirred at −78° C. for 30 min. Propan-2-one (1 g, 17.22 mmol) was added and the reaction was stirred at −78° C. for 2 h. HCl (6 N in water, 5 mL) was then added to the reaction and the mixture was stirred at 15° C. for 16 h. The volatiles were removed under reduced pressure and purified by reverse phase HPLC (ACN/water with 0.1% TFA modifier) to give the title compound. MS: 212 (M+1).

Intermediate E3

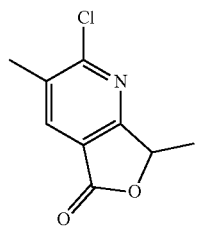

2-Chloro-3,7-dimethylfuro[3,4-b]pyridin-5(7H)-one (Scheme E)
Step 1: Methyl 6-chloro-2-(1-ethoxyvinyl)-5-methylnicotinate
A mixture of methyl 6-chloro-2-iodo-5-methylnicotinate (1.5 g, 4.82 mmol), dibutyl(1-ethoxyvinyl)(propyl)stannane (1.88 mL, 5.78 mmol) and Pd(Ph$_3$P)$_4$ (0.556 g, 0.482 mmol) in toluene (5 mL) was stirred at 120° C. for 16 h under an atmosphere of nitrogen. The volatiles were removed to yield the title compound as a crude mixture.
Step 2: Methyl 2-acetyl-6-chloro-5-methylnicotinate
A solution of methyl 6-chloro-2-(1-ethoxyvinyl)-5-methylnicotinate (0.83 g, 3.25 mmol) in aqueous hydrogen chloride (1 M, 5 mL, 5.0 mmol) and MeOH (5 mL) was stirred at 15° C. for 16 h. The reaction was neutralized by the addition of solid Na$_2$CO$_3$ to pH~8 and extracted with EtOAc. The organic layer was dried over anhydrous sodium sulfate, filtered and concentrated to dryness. Purification by silica gel chromatography (90:10 petroleum ether:THF) provided the title compound.

Step 3: 2-Chloro-3,7-dimethylfuro[3,4-b]pyridin-5(7H)-one

To a solution of methyl 2-acetyl-6-chloro-5-methylnicotinate (140 mg, 0.615 mmol) in THF (15 mL) was added sodium borohydride (23.3 mg, 0.615 mmol). The reaction was stirred at 10° C. for 16 h and was quenched by the addition of water (10 mL) and extracted with EtOAc (20 mL). The combined organic layers were dried over anhydrous sodium sulfate, filtered and the filtrate was concentrated in vacuo. The residue was diluted with DCM (10 mL) and PCC (300 mg, 1.392 mmol) and the mixture was stirred at 10° C. for 16 h. The mixture was filtered and the filtrate was concentrated and purified by reverse phase HPLC (ACN/water with 0.1% TFA modifier) to afford the title compound. MS: 198 (M+1).

SCHEME F

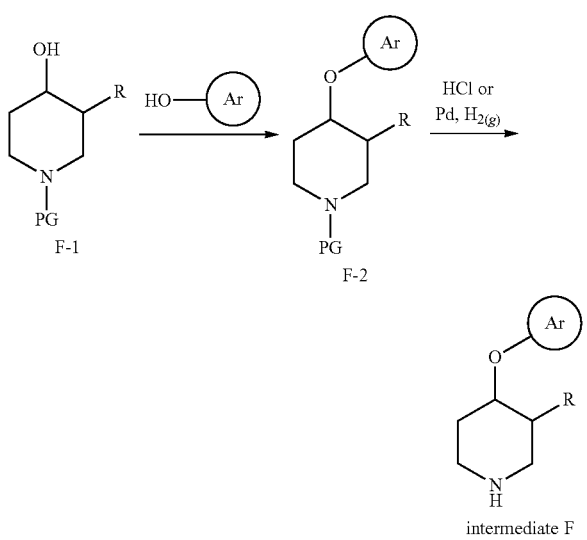

intermediate F

Intermediate F is prepared according to scheme F via Mitsunobu reaction of commercially available N-protected piperidine F-1 with known or prepared phenols (wherein Ar is an aromatic or heteroaromatic ring of $R^1$) to yield adduct F-2. Subsequent deprotection of ether F-2 provides intermediate F.

Intermediate F1

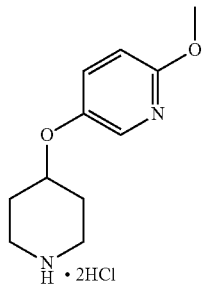

2-Methoxy-5-(piperidin-4-yloxy)pyridine dihydrochloride (Scheme F)

Step 1: tert-Butyl 4-((6-methoxypyridin-3-yl)oxy)piperidine-1-carboxylate

Into a 5-L 4-necked round-bottom flask purged and maintained with an inert atmosphere of nitrogen was placed a solution of 6-methoxypyridin-3-ol (200 g, 1.60 mol) in THF (1.5 L). tert-Butyl 4-hydroxypiperidine-1-carboxylate (386 g, 1.92 mol) and triphenylphosphine (545 g, 2.08 mol) were added followed by the dropwise addition of DIAD (420 g, 2.08 mol) at RT. After stirring for 1 h at 40° C., the resulting solution was diluted with water (2 L) and was partitioned with EtOAc (4 L). The organic layers were combined, washed with brine (2 L), dried over anhydrous sodium sulfate, filtered and concentrated. The residue was purified by silica gel column chromatography (1:10 EtOAc:petroleum ether) to yield the title compound.

Step 2: 2-Methoxy-5-(piperidin-4-yloxy)pyridine dihydrochloride

A solution of tert-butyl 4-((6-methoxypyridin-3-yl)oxy) piperidine-1-carboxylate (270 g, 875.6 mmol) in methanol (2 L) was bubbled slowly with HCl (g). The resulting solution was stirred for 2 h at RT. The volatiles were removed and the crude material was diluted with hot EtOAc: MeOH (8:1) and was then cooled to obtain a precipitate that was collected by filtration to yield the title compound. MS: 236 (M-2HCl+H). $^1$H NMR (300 MHz, D$_2$O): δ 7.79-7.98 (m, 2H), 7.24-7.23 (m, 1H), 4.0 (s, 3H), 3.36-3.40 (m, 2H), 3.15-3.26 (m, 2H), 1.97-2.14 (m, 4H).

The following intermediates in table F were prepared according to scheme F using the procedure outlined in the synthesis of intermediate F1.

TABLE F

| Intermediate | Structure | Name | MS (M + 1) |
|---|---|---|---|
| F2 | 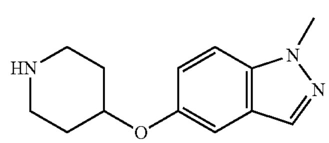 [SMILES: Cn1ncc2cc(OC3CCNCC3)ccc21] | 1-methyl-5-(piperidin-4-yloxy)-1H-indazole | 232 |
| F3 | 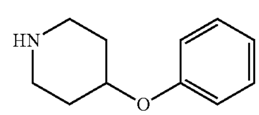 [SMILES: c1ccc(OC2CCNCC2)cc1] | 4-phenoxypiperidine | 178 |

TABLE F-continued

| Intermediate | Structure | Name | MS (M + 1) |
|---|---|---|---|
| F4 | 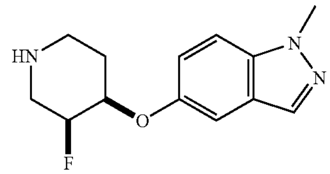 [SMILES: Cn1ncc2cc(O[C@@H]3CCNC[C@@H]3F)ccc21] | 5-(((3S,4R)-3-fluoropiperidin-4-yl)oxy)-1-methyl-1H-indazole | 250 |
| F5 | 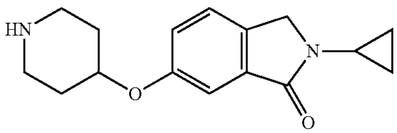 [SMILES: O=C1c2cc(OC3CCNCC3)ccc2CN1C1CC1] | 2-cyclopropyl-6-(piperidin-4-yloxy)isoindolin-1-one | 273 |
| F6 | 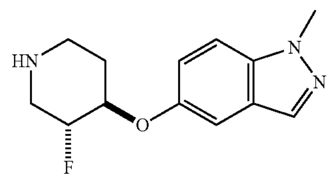 [SMILES: Cn1ncc2cc(O[C@@H]3CCNC[C@H]3F)ccc21] | 5-(((3R,4R)-3-fluoropiperidin-4-yl)oxy)-1-methyl-1H-indazole | 250 |

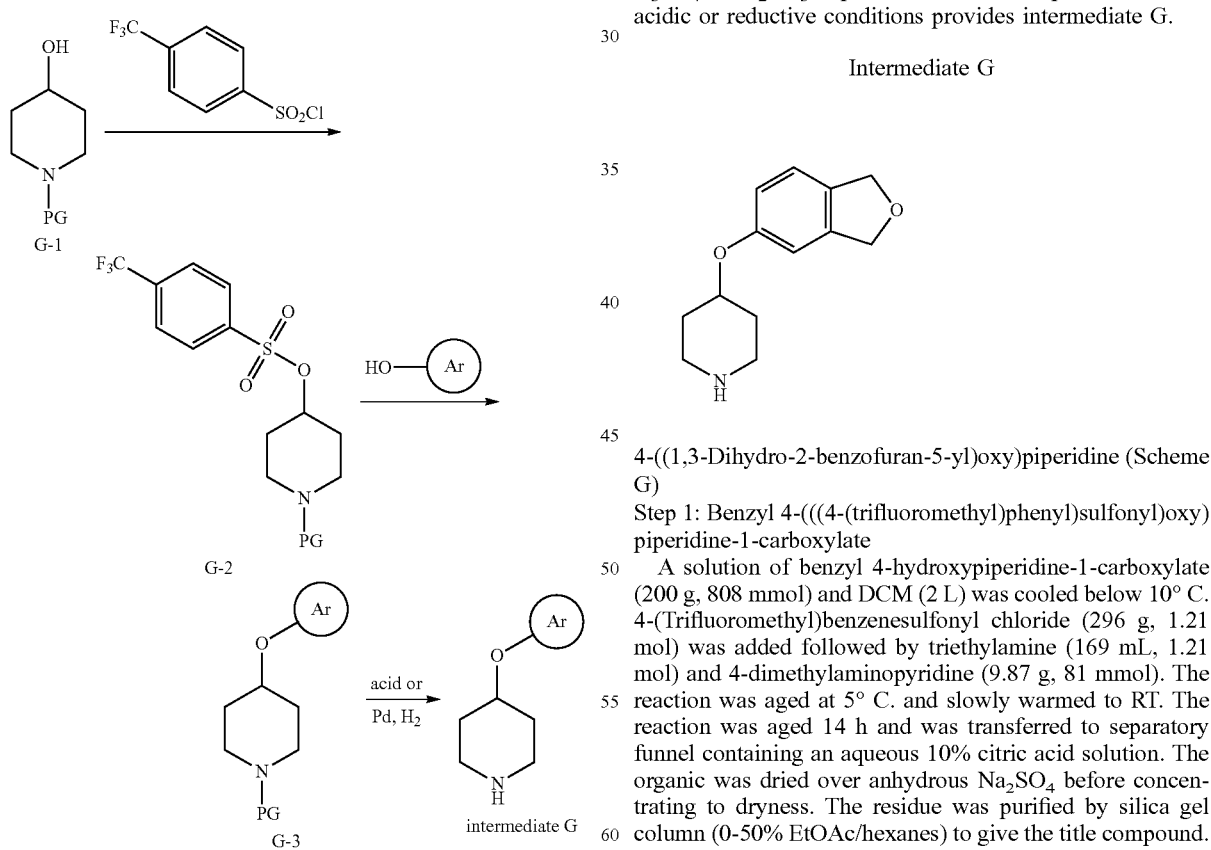

SCHEME G

Intermediate G

Intermediate G is prepared from a commercial alcohol G-1 (wherein PG is an amine protecting group), which after reaction with 4-(trifluoromethyl)benzenesulfonyl chloride forms adduct G-2. Displacement of sulfone G-2 by a known or prepared phenol or alcohol (wherein Ar is an aromatic or heteroaromatic ring of $R^1$) is carried out under the action of $K_3PO_4$ or $Cs_2CO_3$ to provide ether G-3. Deprotection under acidic or reductive conditions provides intermediate G.

4-((1,3-Dihydro-2-benzofuran-5-yl)oxy)piperidine (Scheme G)

Step 1: Benzyl 4-(((4-(trifluoromethyl)phenyl)sulfonyl)oxy)piperidine-1-carboxylate A solution of benzyl 4-hydroxypiperidine-1-carboxylate (200 g, 808 mmol) and DCM (2 L) was cooled below 10° C. 4-(Trifluoromethyl)benzenesulfonyl chloride (296 g, 1.21 mol) was added followed by triethylamine (169 mL, 1.21 mol) and 4-dimethylaminopyridine (9.87 g, 81 mmol). The reaction was aged at 5° C. and slowly warmed to RT. The reaction was aged 14 h and was transferred to separatory funnel containing an aqueous 10% citric acid solution. The organic was dried over anhydrous $Na_2SO_4$ before concentrating to dryness. The residue was purified by silica gel column (0-50% EtOAc/hexanes) to give the title compound.

Step 2: Benzyl 4-((1,3-dihydro-2-benzofuran-5-yl)oxy)piperidine-1-carboxylate

To a flask was added benzyl 4-(((4(trifluoromethyl)phenyl)sulfonyl)oxy)piperidine-1-carboxylate (73.3 g, 165 mmol) and 1,3-dihydro-2-benzofuran-5-ol (15 g, 110 mmol), a fine powder of potassium tribasic phosphate (35.1 g, 165 mmol) and MeCN (150 mL). After being stirred at 60° C. for an appropriate period, the mixture was cooled and poured into water and then extracted with EtOAc. The organic layer was dried over anhydrous Na₂SO₄ before concentrating to dryness. The residue was purified by silica gel column (0-50% EtOAc/hexanes) to give the title compound.

Step 3: 4-((1,3-Dihydro-2-benzofuran-5-yl)oxy)piperidine

To a solution of benzyl 4-((1,3-dihydro-2-benzofuran-5-yl)oxy)piperidine-1-carboxylate (9.7 g, 27.4 mmol) in methanol (194 mL) was added Pd/C (10 wt %, 0.877 g, 2.74 mmol) under an atmosphere of N₂(g). The system was purged and was placed under a balloon of H₂(g) with stirring at RT. Upon completion, the reaction was filtered and the filtrate was concentrated to provide the title compound, which was carried forward without further purification. MS: 220 (M+1).

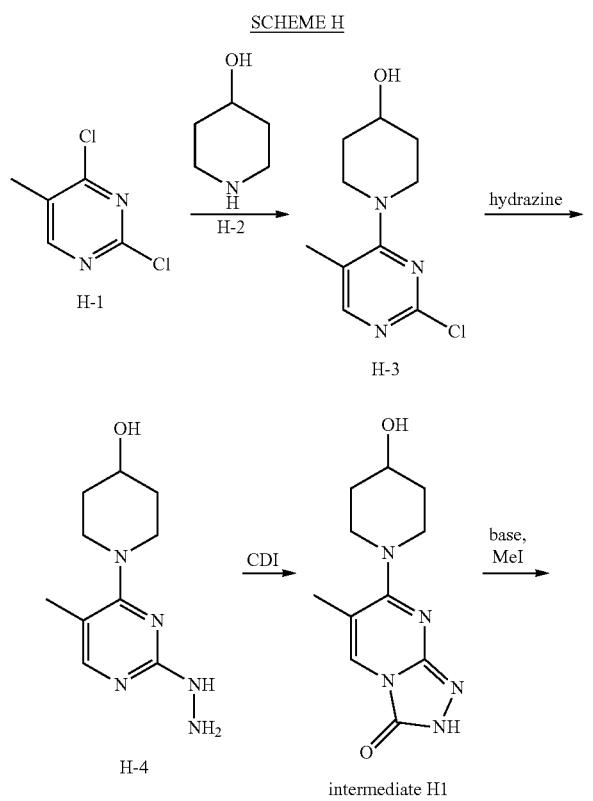

Intermediate H1 and H2 are prepared from commercially available 2,4-dichloro-5-methylpyrimidine (H-1) via an S$_N$Ar reaction of piperidinol H-2. Displacement with hydrazine provides adduct H-4, which is then subjected to reaction with CDI to form intermediate H1. Intermediate H2 is methylated under the action of base in the presence of methyl iodide to provide intermediate H2.

Intermediate H1

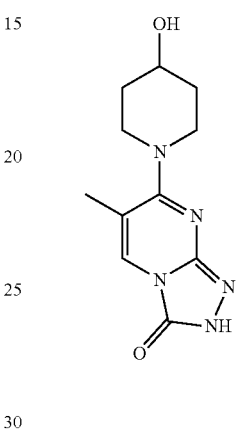

7-(4-Hydroxypiperidin-1-yl)-6-methyl-[1,2,4]triazolo[4,3-a]pyrimidin-3(2H)-one (Scheme H)

Step 1: 1-(2-Chloro-5-methylpyrimidin-4-yl)piperidin-4-ol

To a solution of 2,4-dichloro-5-methylpyrimidine (1.6 g, 9.82 mmol) in DMF (30 mL) was added piperidin-4-ol, TFA (1.09 g, 10.8 mmol) and Et₃N (2.74 mL, 19.6 mmol). The reaction was stirred at RT for 5 h after which time the volatiles were removed under reduced pressure. The residue was purified by silica gel chromatography (10:1-2:1 petroleum ether:EtOAc) to provide the title compound.

Step 2: 1-(2-Hydrazinyl-5-methylpyrimidin-4-yl)piperidin-4-ol

To a solution of 1-(2-chloro-5-methylpyrimidin-4-yl)piperidin-4-ol (2.00 g, 8.78 mmol) in EtOH (30 mL) and water (6 mL) was added hydrazine hydrate (2.13 mL, 43.9 mmol). The reaction was stirred at 90° C. for 5 h after which time the volatiles were removed under reduced pressure and diluted with water (20 mL). The title compound was isolated by filtration and was carried forward without further purification.

Step 3: 7-(4-Hydroxypiperidin-1-yl)-6-methyl-[1,2,4]triazolo[4,3-a]pyrimidin-3(2H)-one To a solution of 1-(2-hydrazinyl-5-methylpyrimidin-4-yl)piperidin-4-ol (1.7 g, 7.61 mmol) in THF (30 mL) was added CDI (1.482 g, 9.14 mmol) and the mixture was stirred at RT for 3 h. The volatiles were removed under reduced pressure and was then diluted with water (80 mL) and extracted with DCM (40 mL×3). The combined organic layers were dried over anhydrous sodium sulfate, filtered, and then purified by flash chromatography (10:1-1:4 petroleum ether::EtOAc) to give the title compound. MS: 250 (M+1).

Intermediate H2

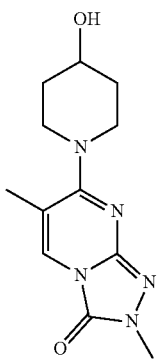

7-(4-hydroxypiperidin-1-yl)-2,6-dimethyl-[1,2,4]triazolo[4,3-a]pyrimidin-3(2H)-one (Scheme H)

To a solution of 7-(4-hydroxypiperidin-1-yl)-6-methyl-[1,2,4]triazolo[4,3-a]pyrimidin-3(21H)-one (intermediate H1, 100 mg, 0.401 mmol) in DMF (10 mL) was added $K_2CO_3$ (111 mg, 0.802 mmol) and MeI (0.038 mL, 0.602 mmol) and was heated to 60° C. for 16 h. The mixture was concentrated in vacuo, then diluted with water (50 mL) and extracted with DCM (40 mL×3). The combined organic layers were dried over anhydrous sodium sulfate, filtered, and purified by silica gel chromatography (10:1 to 1:4 petroleum ether: EtOAc) to give the title compound. MS: 264 (M+1).

SCHEME I

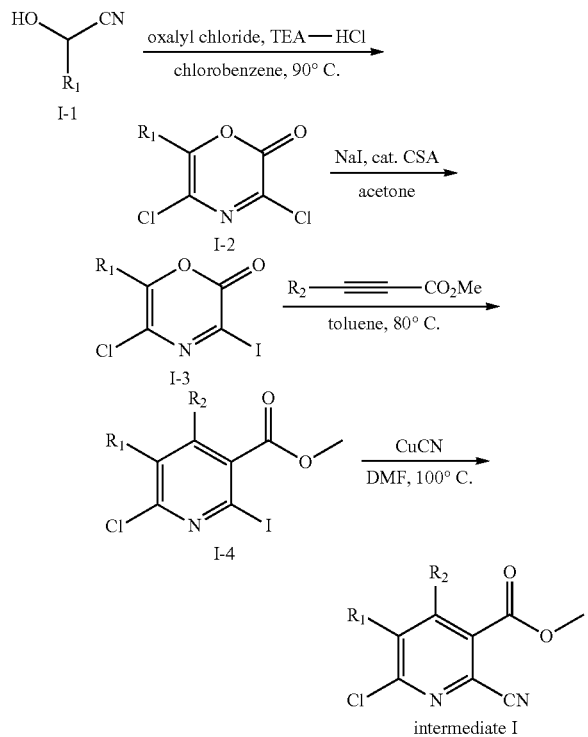

Intermediate I is prepared according to Scheme A via condensation of commercially available hydroxy nitrile I-1 with oxalyl chloride to yield adduct I-2. A Finkelstein reaction of chloride I-2 iodide product I-3. A hetero-Diels-Alder reaction of diene A-3 with a commercially available ynone gives pyridine I-4. A subsequent copper-meditated cyanation provides intermediate I.

Intermediate I

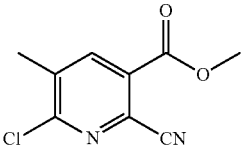

Methyl 6-chloro-2-cyano-5-methylnicotinate (Scheme I)

Step 1: 3,5-Dichloro-6-methyl-2H-1,4-oxazin-2-one

Into a 10-L 4-necked round-bottom flask was charged oxalic dichloride (3.32 kg, 26.2 mol) and chlorobenzene (3.5 L) under an inert atmosphere of nitrogen. A solution of 2-hydroxypropanenitrile (464.8 g, 6.54 mol) in chlorobenzene (500 mL) was added dropwise to the flask at 0° C. The system was heated to 90° C. and triethylamine hydrochloride (66.2 g, 481 mmol) was added in portions at 90° C. The resulting solution was stirred for 3 h before concentrating the mixture under reduced pressure. The resulting solution was diluted with ether (5 L) and the solids were filtered out. The filtrate concentrated and was then applied purified by silica gel column chromatography (0:1-1:4 EtOAc:petroleum ether) to yield the title compound.

Step 2: 5-Chloro-3-iodo-6-methyl-2H-1,4-oxazin-2-one

Into a 10-L 4-necked round-bottom flask was added 3,5-dichloro-6-methyl-2H-1,4-oxazin-2-one (470.8 g, 2.62 mol), acetone (10 L), NaI (1568 g, 10.5 mol) and camphorsulfonic acid (40 g, 172.2 mmol) under an atmosphere of nitrogen. The resulting solution was stirred for 3 h at 25° C. The mixture was concentrated and then diluted with water (20 L) and dichloromethane (3×5 L). The organic layers were combined and washed with brine (5 L). The mixture was dried over anhydrous sodium sulfate, filtered and was concentrated under reduced pressure to yield the title compound.

Step 3: Methyl 6-chloro-2-iodo-5-methylnicotinate

Into a 5-L 3-necked round-bottom flask was placed 5-chloro-3-iodo-6-methyl-2H-1,4-oxazin-2-one (638 g, 2.35 mol), toluene (2.3 L), and methyl prop-2-ynoate (592.8 g, 7.05 mol) under an atmosphere of nitrogen. The resulting solution was stirred for 2 days at 80° C. The reaction was cooled and the volatiles were removed under reduced pressure. The residue was purified by silica gel column chromatography (0:1-1:50 ethyl acetate:petroleum ether) to provide the major regioisomeric product as the title compound.

Step 4: Methyl 6-chloro-2-cyano-5-methylnicotinate

Into a 20-mL microwave tube was added methyl 6-chloro-2-iodo-5-methylpyridine-3-carboxylate (2 g, 6.42 mmol), DMF (15 mL), and CuCN (850 mg, 9.60 mmol). The resulting solution was stirred for 5 min at 100° C. by microwave irradiation. The mixture was diluted with water (20 mL) and a saturated, aqueous solution of $NH_4Cl$ (100 mL). Dichloromethane (2×20 mL) was used to extract the crude material and the organic layers were combined and dried over anhydrous sodium sulfate. The residue was purified by silica gel chromatography (0:1-1:8 ethyl acetate: petroleum ether) to provide the title compound. MS: 211 (M+1). $^1$H NMR (500 MHz, CDCl$_3$): δ 7.87 (s, 1H), 3.95 (s, 4H), 2.37 (s, 3H).

SCHEME J

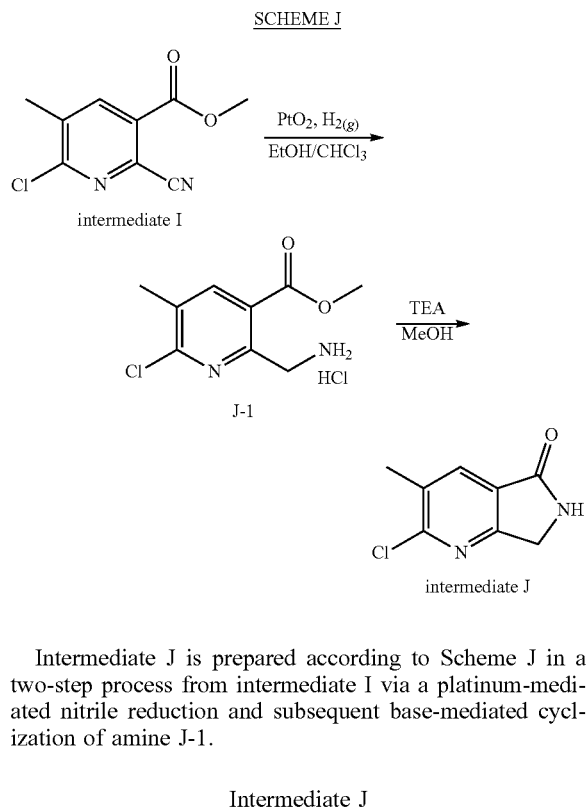

intermediate J

Intermediate J is prepared according to Scheme J in a two-step process from intermediate I via a platinum-mediated nitrile reduction and subsequent base-mediated cyclization of amine J-1.

Intermediate J

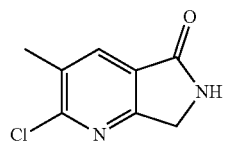

2-Chloro-3-methyl-6,7-dihydro-5H-pyrrolo[3,4-b]pyridin-5-one (Scheme J)

Step 1: Methyl 2-(aminomethyl)-6-chloro-5-methylnicotinate hydrochloride

Into a 5-L 2-necked round-bottom flask was placed methyl 6-chloro-2-cyano-5-methylpyridine-3-carboxylate (intermediate I, 82 g, 389.3 mmol), 3:1 ethanol:chloroform (2.5 L) and $PtO_2$ (15 g). The resulting solution was stirred for 36 h at RT under an atmosphere of hydrogen. The solids were removed by filtration and the filtrate was concentrated under reduced pressure to yield the title compound.

Step 2: 2-Chloro-3-methyl-6,7-dihydro-5H-pyrrolo[3,4-b]pyridin-5-one

Into a 10 L 4-necked round-bottom flask purged and maintained with an inert atmosphere of nitrogen, was placed methyl 2-(aminomethyl)-6-chloro-5-methylpyridine-3-carboxylate hydrochloride (110 g, 438 mmol), methanol (6 L), triethylamine (221.6 g, 2.19 mol). The resulting solution was stirred for 12 h at RT. The solids were removed by filtration and the filtrate was concentrated under reduced pressure to yield the crude product. Addition of hot DCM eventually resulted in the formation of a precipitate which was isolated by filtration to yield the title compound. MS: 183 (M+1). $^1H$ NMR (500 MHz, $CDCl_3$): δ 2.45 (s, 3H), 4.39 (s, 2H), 8.11 (s, 1H), 8.82 (s, 1H).

SCHEME K

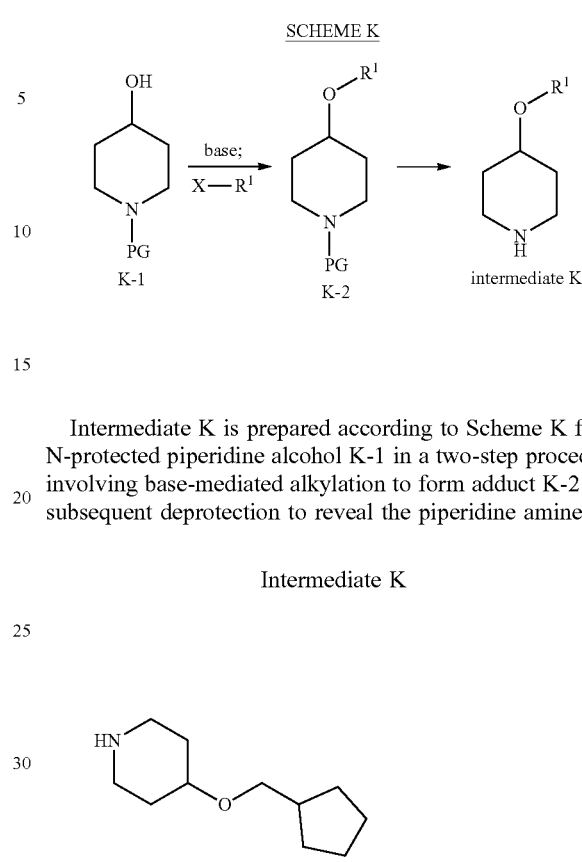

Intermediate K is prepared according to Scheme K from N-protected piperidine alcohol K-1 in a two-step procedure involving base-mediated alkylation to form adduct K-2 and subsequent deprotection to reveal the piperidine amine.

Intermediate K

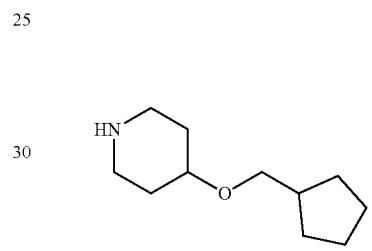

4-(Cyclopentylmethoxy)piperidine (Scheme K)

Step 1: tert-Butyl 4-(cyclopentylmethoxy)piperidine-1-carboxylate

A mixture of tert-butyl 4-hydroxypiperidine-1-carboxylate (285 mg, 1.42 mmol) and sodium hydride (60%, 42.5 mg, 1.77 mmol) in DMF (2 mL) was stirred at 70° C. for 30 min, then cyclopentylmethyl 4-methylbenzenesulfonate (300 mg, 1.18 mmol) was added to the mixture. The reaction mixture was stirred at 70° C. for 2 h. The reaction was cooled to RT and aqueous $NH_4Cl$ (saturated, 5 mL) was added to the mixture and the solution was then poured into water (5 mL), extracted with EtOAc (5 mL×3). The combined organic layers were washed with brine (5 mL×3), dried over anhydrous sodium sulfate, filtered and the filtrate was concentrated in vacuo. The residue was purified by silica gel chromatography (0-4% EtOAc/petroleum ether) to afford the title compound.

Step 2: 4-(Cyclopentylmethoxy)piperidine

A mixture of tert-butyl 4-(cyclopentylmethoxy)piperidine-1-carboxylate (200 mg, 0.706 mmol) and TFA (0.54 mL, 7.06 mmol) in DCM (2 mL) was stirred at 20° C. for 30 min. The volatiles were removed under reduced pressure to afford the title compound. $^1H$ NMR (400 MHz, methanol-d4): δ 3.59-3.68 (m, 1H), 3.35 (d, J=6.80 Hz, 2H), 3.20-3.25 (m, 2H), 3.03-3.14 (m, 2H), 2.09-2.16 (m, 1H), 1.91-2.03 (m, 2H), 1.81-1.88 (m, 2H), 1.67-1.75 (m, 2H), 1.45-1.65 (m, 4H), 1.16-1.36 (m, 2H).

SCHEME L

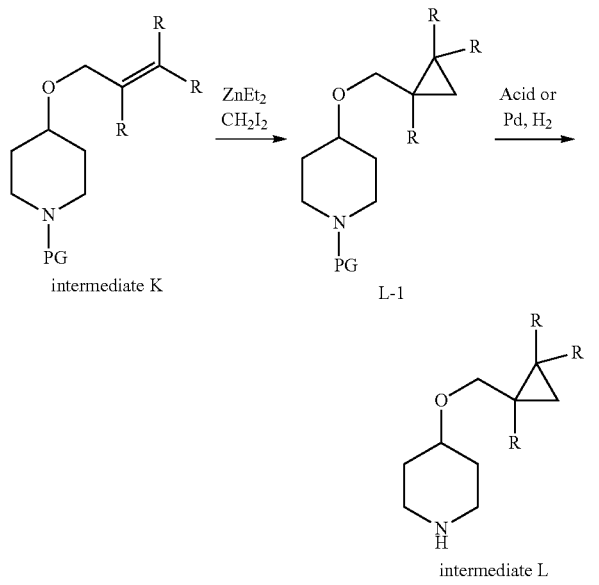

intermediate K

L-1 intermediate L

Intermediate L is prepared according to Scheme L from N-protected piperidine alcohol intermediate K in a two-step procedure involving Simmons-Smith reaction to form adduct L-1 and subsequent deprotection to reveal the piperidine amine.

Intermediate L

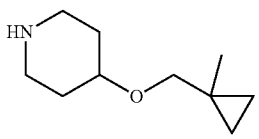

4-((1-Methylcyclopropyl)methoxy)piperidine (Scheme L)

Step 1: Benzyl 4-((1-methylcyclopropyl)methoxy)piperidine-1-carboxylate

To a solution of benzyl 4-((2-methylallyl)oxy)piperidine-1-carboxylate (9 g, 31.1 mmol) in DCM (100 mL) were added diiodomethane (41.7 g, 156 mmol) and diethylzinc (1 M, 93 mL, 93 mmol) at −5° C. for 3 h. The reaction mixture was diluted with water (100 mL) and extracted with EtOAc (100 mL×3). The combined organic layers were washed with brine (80 mL), dried over anhydrous sodium sulfate, filtered and the filtrate was concentrated in vacuo. The residue was purified by chromatography column (15% EtOAc/petroleum ether) to give the title compound.

Step 2: 4-((1-Methylcyclopropyl)methoxy)piperidine

To a solution of benzyl 4-((1-methylcyclopropyl)methoxy)piperidine-1-carboxylate (1 g, 3.30 mmol) in MeOH (10 mL) was added Pd/C (10 wt %, 3.51 g, 3.30 mmol). The reaction was stirred under an atmosphere of $H_2$ (15 psi) at RT for 1 h. The mixture was filtered and the filtrate was concentrated in vacuo to yield the title compound. MS: 170 (M+1).

SCHEME M

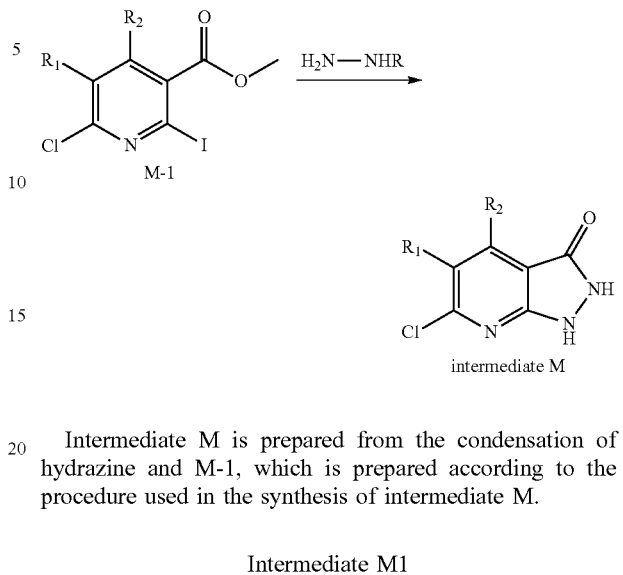

intermediate M

Intermediate M is prepared from the condensation of hydrazine and M-1, which is prepared according to the procedure used in the synthesis of intermediate M.

Intermediate M1

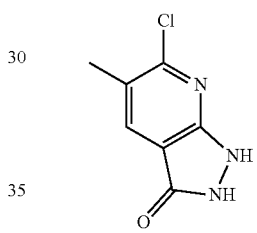

6-Chloro-5-methyl-1,2-dihydro-3H-pyrazolo[3,4-b]pyridin-3-one (Scheme M)

Hydrazine (0.50 mL, 16.1 mmol) was added to a stirred solution of methyl 6-chloro-2-iodo-5-methylnicotinate (500 mg, 1.61 mmol) in ethanol (10 mL). The reaction was stirred at 80° C. under microwave irradiation for 2 h. The volatiles were removed under reduced pressure and concentrated to give the title compound, which was used without purification. MS: 184 (M+1).

The following intermediates in table M were prepared according to scheme M using the procedure outlined in the synthesis of intermediate M1 using methyl hydrazine.

TABLE M

| Intermediate | Structure | Name | MS (M + 1) |
|---|---|---|---|
| M2 | ![structure] | 6-chloro-1,5-dimethyl-1,2-dihydro-3H-pyrazolo[3,4-b]pyridin-3-one | 198 |

SCHEME N

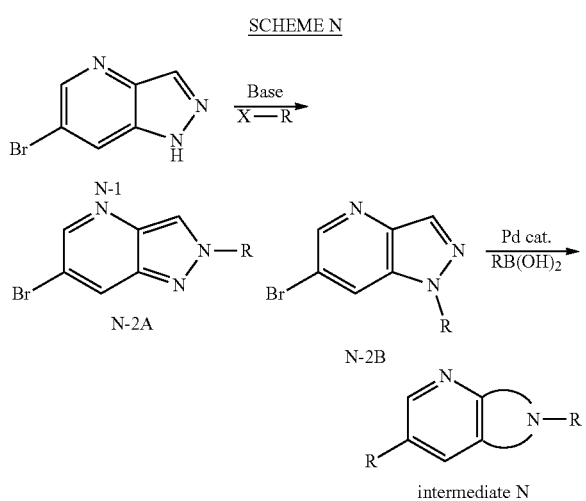

Intermediate N is prepared according to scheme N beginning with commercially available bromide N-1 via an alkylation reaction with an alkyl halide in the presence of base and a subsequent Suzuki coupling reaction with a commercially available boronic acid.

Intermediate N1

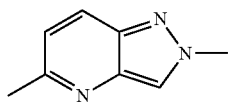

2,5-Dimethyl-2H-pyrazolo[4,3-b]pyridine (Scheme U)
Step 1: 6-Bromo-2-methyl-2H-pyrazolo[4,3-b]pyridine To a solution of 6-bromo-2H-pyrazolo[4,3-b]pyridine (1.5 g, 7.57 mmol) in DMF (30 mL) was added sodium hydride (60%, 0.364 g, 9.09 mmol) at 0° C. The reaction mixture was stirred for 30 min before iodomethane (3.23 g, 22.72 mmol) was added the reaction mixture was stirred at 0° C. for 4 h. The reaction was diluted with aqueous NH$_4$Cl (saturated, 50 mL) and extracted with EtOAc (50 mL×4). The combined organic fractions were washed with water (100 mL×3), dried over anhydrous sodium sulfate, filtered and concentrated under reduced pressure. The residue was purified by silica gel chromatography (0-40% THF/petroleum ether) to give the title compound as the lower eluting product (R$_f$=0.60, 1:1 EtOAc: petroleum ether). $^1$H NMR (400 MHz, methanol-d$_4$): δ 8.57 (1H, d, J=1.6, Hz), 8.19 (1H, d, J=9.9 Hz), 4.26 (3H, s), as well as the regioisomeric product, 6-bromo-1-methyl-1H-pyrazolo[4,3-b]pyridine as the higher eluting product (R$_f$=0.30, 1:1 EtOAc:petroleum ether). $^1$H NMR (400 MHz, methanol-d$_4$): δ 8.41 (1H, d, J=1.6, Hz), 8.20 (1H, s), 7.95 (1H, s), 4.08 (3H, s).
Step 2: 2,6-Dimethyl-2H-pyrazolo[4,3-b]pyridine To a solution of 6-bromo-2-methyl-2H-pyrazolo[4,3-b]pyridine (500 mg, 2.36 mmol), K$_3$PO$_4$ (1.50 g, 7.07 mmol) and methylboronic acid (423 mg, 7.07 mmol) in THF (4 mL) and water (1 mL) was added 1,1'-bis(di-tert-butylphosphino)ferrocene palladium dichloride (77 mg, 0.118 mmol). The reaction mixture was stirred at 70° C. for 15 h under a nitrogen atmosphere. The reaction was cooled and diluted with water (10 mL) and the mixture was extracted with EtOAc (20 mL×3). The combined organic fractions were washed with water (30 mL×3), dried over anhydrous sodium sulfate, filtered and the filtrate evaporated under reduced pressure. The residue was purified by silica gel chromatography (0-50% THF/petroleum ether) to afford the title compound. MS: 148 (M+1).

The following intermediates in table N were prepared according to scheme N using the procedure outlined in the synthesis of intermediate N1.

TABLE N

| Intermediate | Structure | Name | MS (M + 1) |
|---|---|---|---|
| M2 | 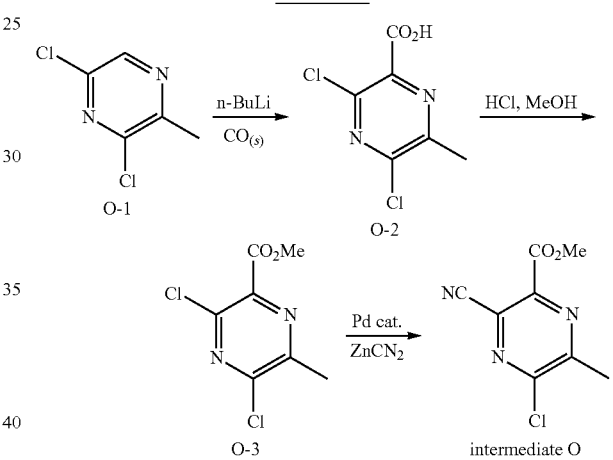 | 1,6-dimethyl-1H-pyrazolo[4,3-b]pyridine | 148 |

SCHEME O

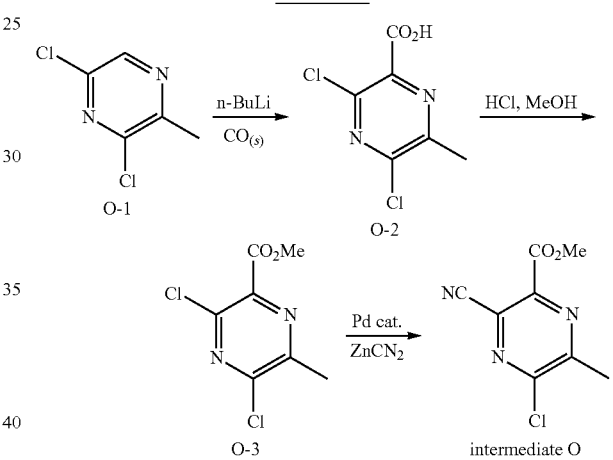

Intermediate O is prepared according to scheme O beginning with commercially available pyrazine O-1. Deprotonation with n-butyllithium and quenching with dry ice provides acid adduct O-2. Esterification under acidic conditions provides methyl ester O-3 and a subsequent palladium-mediated cyanation affords intermediate O.

Intermediate O

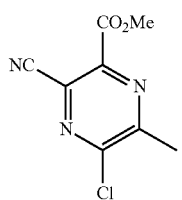

Methyl 5-chloro-3-cyano-6-methylpyrazine-2-carboxylate (Scheme O)
Step 1: 3,5-Dichloro-6-methylpyrazine-2-carboxylic acid To a solution of 2,2,6,6-tetramethylpiperidine (433 mg, 3.07 mmol) in THF (10 mL) was added n-butyllithium (2.5

M, 1.47 mL, 3.68 mmol) at −78° C. and the mixture was stirred at −78° C. for 30 min, then 3,5-dichloro-2-methylpyrazine (500 mg, 3.07 mmol) was added and stirred for an additional 30 min at −78° C. Dry ice (3 g) was added at −78° C., the mixture was stirred at 20° C. for 16 h under an atmosphere of nitrogen. The mixture was quenched with aqueous NH₄Cl (saturated, 100 mL) and extracted with DCM (70 mL×3). The combine organic layers were concentrated in vacuo to give the title compound, which was used for next step directly without further purification.

Step 2: Methyl 3,5-dichloro-6-methylpyrazine-2-carboxylate

To a solution of 3,5-dichloro-6-methylpyrazine-2-carboxylic acid (410 mg, 1.98 mmol) in MeOH (10 mL) was added conc. HCl (1.63 mL, 19.81 mmol) at 20° C. The reaction was stirred at 80° C. for 16 h. The mixture was diluted with water (100 mL) and extracted with DCM (60 mL×3). The combined organic layers were dried over anhydrous sodium sulfate, filtered, and concentrated in vacuo. The residue was purified by silica gel chromatography (100:1-7:1 petroleum ether:EtOAc) to give the title compound. ¹H NMR (400 MHz, CDCl₃): δ 4.00 (3H, s), 2.68 (3H, s).

Step 3: Methyl 5-chloro-3-cyano-6-methylpyrazine-2-carboxylate

A solution of methyl 3,5-dichloro-6-methylpyrazine-2-carboxylate (200 mg, 0.905 mmol), Pd₂(dba)₃ (207 mg, 0.226 mmol), 2-dicyclohexylphosphino-2',6'-di-iso-proproxy-1,1'-biphenyl (211 mg, 0.452 mmol) and dicyanozinc (212 mg, 1.810 mmol) in DMF (1 mL) was sealed in a microwave vial and was irradiated 150° C. for 30 min. The reaction was directly purified by The reaction was purified by prep-TLC (1:1 petroleum ether: EtOAc) to afford the title compound. MS: 384 (M+1).

SCHEME P

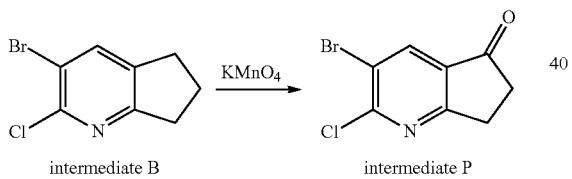

intermediate B     intermediate P

Intermediate P is prepared according to scheme P after a benzylic oxidation of intermediate B using potassium permanganate.

Intermediate P

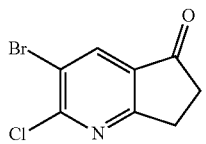

3-Bromo-2-chloro-6,7-dihydro-5H-cyclopenta[b]pyridin-5-one (Scheme P)

To a solution of magnesium sulfate (3.88 g, 32.3 mmol) and potassium permanganate (2.04 g, 12.9 mmol) in water (20 mL) and t-BuOH (60 mL) was added 3-bromo-2-chloro-6,7-dihydro-5H-cyclopenta[b]pyridine (intermediate B, 1.5 g, 6.45 mmol). The mixture was stirred at 40° C. for 3 h, and was then filtered and extracted with EtOAc (10 mL×2). The combined organic layers were washed with brine (20 mL×2), filtered, concentrated under reduced pressure and purified by silica gel chromatography (0-10% EtOAc in petroleum ether) to afford the title compound. MS: 246, 248 (M+1).

INTERMEDIATE Q

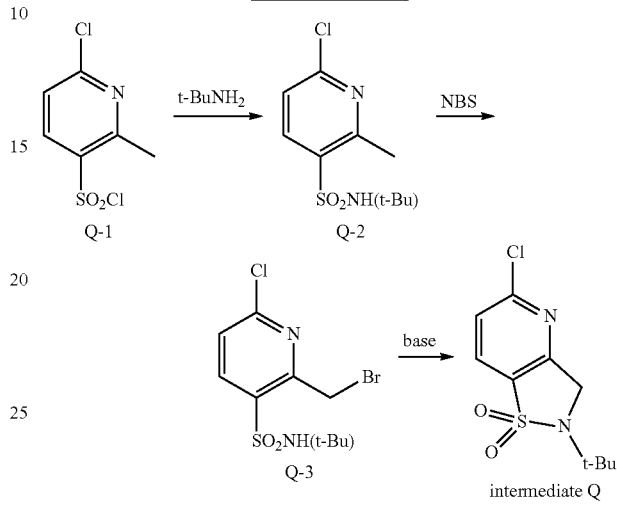

Intermediate Q is prepared according to scheme Q from commercially available sulfonyl chloride Q-1 after reaction with tert-butylamine to form sulfonamide Q-2. Radical bromination by NBS and exposure to base resulted in cyclization to form intermediate Q.

Intermediate Q

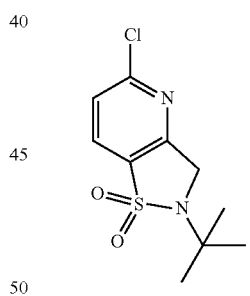

2-(tert-Butyl)-5-chloro-2,3-dihydroisothiazolo[4,5-b]pyridine 1,1-dioxide (Scheme U)

Step 1: N-(tert-butyl)-6-chloro-2-methylpyridine-3-sulfonamide

A mixture of 2-methylpropan-2-amine (0.485 g, 6.63 mmol), 6-chloro-2-methylpyridine-3-sulfonyl chloride (1 g, 4.42 mmol) and TEA (1.23 mL, 8.85 mmol) in MeCN (20 mL) was stirred at 15° C. for 16 h. The mixture was poured into EtOAc (30 mL), washed with water (50 mL), dried over anhydrous sodium sulfate, filtered and the filtrate was concentrated to give the title compound.

Step 2: 2-(Bromomethyl)-N-(tert-butyl)-6-chloropyridine-3-sulfonamide

A mixture of N-(tert-butyl)-6-chloro-2-methylpyridine-3-sulfonamide (500 mg, 1.90 mmol), NBS (339 mg, 1.90 mmol) and benzoic peroxyanhydride (92 mg, 0.38 mmol) in CCl$_4$ (3 mL) was stirred at 90° C. for 16 h. The mixture was concentrated to give the title compound.

Step 3: 2-(tert-butyl)-5-chloro-2,3-dihydroisothiazolo[4,5-b]pyridine 1,1-dioxide A mixture of 2-(bromomethyl)-N-(tert-butyl)-6-chloropyridine-3-sulfonamide (650 mg, 0.761 mmol) and sodium bicarbonate (192 mg, 2.28 mmol) in MeCN (3 mL) was stirred at 120° C. for 16 h. The mixture was filtered and the filtrate was concentrated and purified by reverse phase HPLC (ACN/water with 0.1% TFA modifier) to afford the title compound. $^1$H NMR (400 MHz, CDCl$_3$): δ 8.00 (1H, d, J=8.4 Hz), 7.47 (1H, d, J=8.4 Hz), 4.49 (2H, s), 1.57 (3H, s).

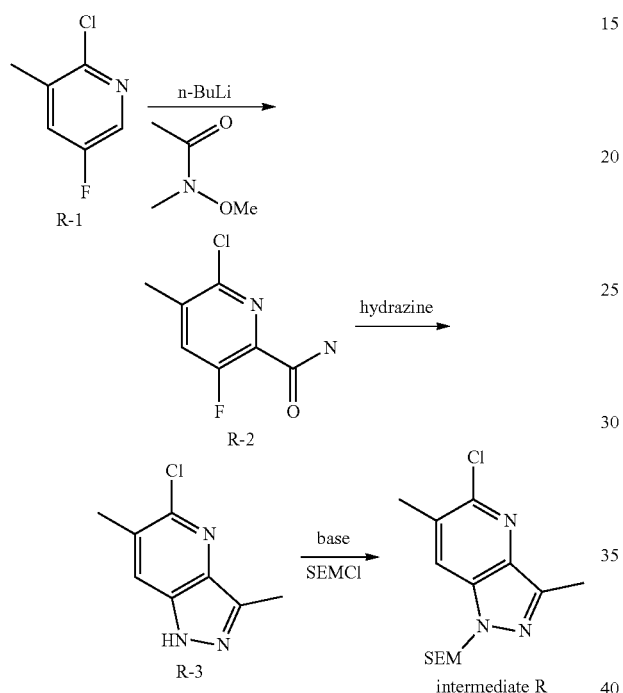

Intermediate R is prepared according to scheme R from commercially available pyridine R-1 by anion formation with n-butyllithium and reaction with N-methoxy-N-methylacetamide to form ketone R-2. Subsequent condensation with hydrazine then yields the pyrazole R-3, which is then subjected to N-protection with SEMCl.

Intermediate R

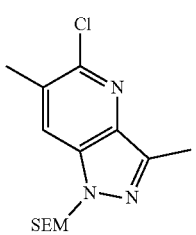

5-Chloro-3,6-dimethyl-1-((2-(trimethylsilyl)ethoxy)methyl)-1H-pyrazolo[4,3-b]pyridine (Scheme R)

Step 1: 1-(6-Chloro-3-fluoro-5-methylpyridin-2-yl)ethanone

To a solution of 2-chloro-5-fluoro-3-methylpyridine (582 mg, 4.00 mmol) in THF (10 mL) was added n-butyllithium (2.5 M, 2.50 mL, 6.25 mmol) at −78° C. under a nitrogen atmosphere. After stirring for 1 hr, N-methoxy-N-methylacetamide (495 mg, 4.80 mmol) was added to the reaction and the resulting mixture stirred at −78° C. for 1 h. The reaction was quenched with water (0.5 mL) and the volatiles were removed under reduced pressure. The residue was purified by silica gel chromatography (5% THF/petroleum ether) to give the title compound.

Step 2: 5-Chloro-3,6-dimethyl-1H-pyrazolo[4,3-b]pyridine 1-(6-Chloro-3-fluoro-5-methylpyridin-2-yl)ethanone (160 mg, 0.853 mmol) was dissolved in hydrazine monohydrate (5n mL) and the mixture was heated to 120° C. for 5 h. The reaction was cooled to RT and was diluted with water (20 mL), extracted with DCM (10 mL×3), dried over anhydrous sodium sulfate, filtered and concentrated to afford the title compound.

Step 3: 5-Chloro-3,6-dimethyl-1-((2-(trimethylsilyl)ethoxy)methyl)-1H-pyrazolo[4,3-b]pyridine To a solution of 5-chloro-3,6-dimethyl-1H-pyrazolo[4,3-b]pyridine (100 mg, 0.551 mmol) was dissolved in DMF (3 mL) at 0° C. was added sodium hydride (60%, 33.0 mg, 0.826 mmol) under a nitrogen atmosphere. The mixture was stirred for 30 min before (2-(chloromethoxy)ethyl)trimethylsilane (138 mg, 0.826 mmol) was added and the resulting mixture was gradually warmed to RT and was stirred for 2 h. The reaction was diluted with water (15 mL), extracted with EtOAc (10 mL×3) and the combined organic phases were washed with water (10 mL×3), dried over anhydrous sodium sulfate, filtered and concentrated. The residue was purified by silica gel chromatography (5% THF/petroleum ether) to give the title compound. MS: 312 (M+1).

SCHEME S

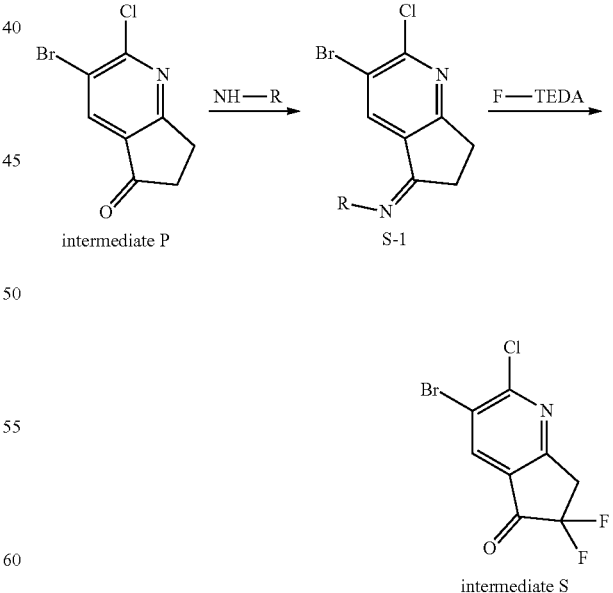

Intermediate S is prepared from intermediate P via activation via formation of an intermediary imine S-1 to enable the subsequent α-difluorination reaction.

Intermediate S

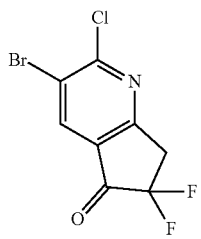 [SMILES: O=C1c2cc(Br)c(Cl)nc2CC1(F)F]

3-Bromo-2-chloro-6,6-difluoro-6,7-dihydro-5H-cyclopenta[b]pyridin-5-one (Scheme S)

Step 1: N-(3-bromo-2-chloro-6,7-dihydro-5H-cyclopenta[b]pyridin-5-ylidene)butan-1-amine To a solution of 3-bromo-2-chloro-6,7-dihydro-5H-cyclopenta[b]pyridin-5-one (intermediate P, 62 mg, 0.252 mmol) in cyclohexane (2 mL) was added butan-1-amine (22 mg, 0.302 mmol) and TFA (1.9 µL, 0.025 mmol), the mixture was stirred at 130° C. for 14 h. The mixture was concentrated to give a residue that was dissolved MTBE (50 mL). The solution was washed by aqueous saturated sodium bicarbonate (10 mL×2), then brine (10 mL×2), dried over anhydrous sodium sulfate and concentrated to afford the title compound.

Step 2: 3-Bromo-2-chloro-6,6-difluoro-6,7-dihydro-5H-cyclopenta[b]pyridin-5-one

To a solution of N-(3-bromo-2-chloro-6,7-dihydro-5H-cyclopenta[b]pyridin-5-ylidene)butan-1-amine (90 mg, 0.239 mmol) in MeCN (3 mL) was added sodium sulfate (24 mg, 0.169 mmol) and 1-chloromethyl-4-fluoro-1,4-diazoniabicyclo[2.2.2]octane bis(tetrafluoroborate) (169 mg, 0.477 mmol). The suspension was mixed and heated at 100° C. for 12 h. HCl (37%, 0.2 mL, 2.435 mmol) was added and the mixture was stirred for an additional 15 min. After cooling to RT, the mixture was diluted with MTBE (20 mL), washed with saturated aqueous sodium bicarbonate (5 mL×2), 10% brine (5 mL×2) and concentrated to give the title compound. $^1$H NMR (400 MHz, CDCl$_3$): δ 8.34 (1H, s), 3.64 (2H, t, J=12 Hz).

Intermediate T

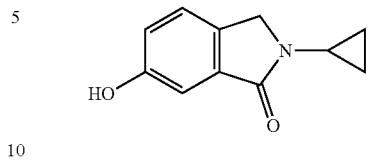

2-Cyclopropyl-6-hydroxyisoindolin-1-one (Scheme T)

Step 1: 2-Cyclopropyl-6-(4,4,5,5-tetramethyl-1,3,2-dioxaborolan-2-yl)isoindolin-1-one 6-Bromo-2-Cyclopropyl isoindolin-1-one (900 mg, 3.57 mmol), bis(pinacolato)diboron (997 mg, 3.93 mmol), 1,1'-bis(di-tert-butylphosphino)ferrocene palladium dichloride (233 mg, 0.357 mmol) and KOAc (701 mg, 7.14 mmol) were suspended in toluene (14.5 mL) under an atmosphere of nitrogen. The reaction was heated to 60° C. for 1 h before cooling to RT and filtering off solids. The filtrate is concentrated and diluted with THF (15 mL) and hexanes (50 mL) and is aged for 4 h. The solids are collected by filtration (hexanes wash) to afford the title compound. Additional material is recovered from the filtrate which is purified by silica gel chromatography (0-75% EtOAc/hexanes).

Step 2: 2-Cyclopropyl-6-hydroxyisoindolin-1-one

To a solution of 2-cyclopropyl-6-(4,4,5,5-tetramethyl-1,3,2-dioxaborolan-2-yl)isoindolin-1-one (1.0 g, 3.34 mmol) in acetic acid (7 mL) was added H$_2$O$_2$ (1.14 mL, 11.1 mmol) at 0° C. The reaction was gradually warmed to RT and was stirred for 75 min. The mixture was cooled to 0° C., and the solids were collected by filtration and were washed with cold AcOH and ether (3×) to a yield the title compound. Additional material was collected from the filtrate which was treated with aqueous sodium thiosulfate solution and then concentrated to remove acetic acid. The residue was extracted with EtOAc (3×) and the combined organic extracts were washed with aqueous NaHCO$_3$ (saturated), water, brine, then dried over anhydrous sodium sulfate, filtered, and concentrated. The solids were taken up in ether and were filtered to afford a second batch of the title compound. MS: 190 (M+1).

SCHEME T

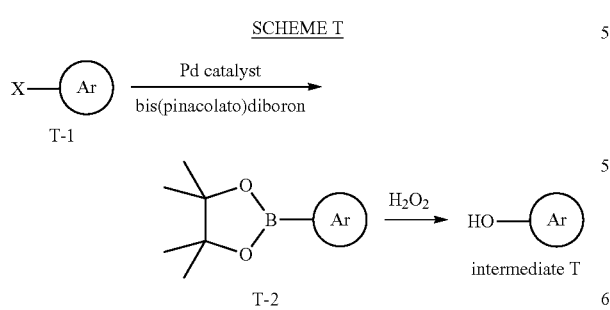

SCHEME U

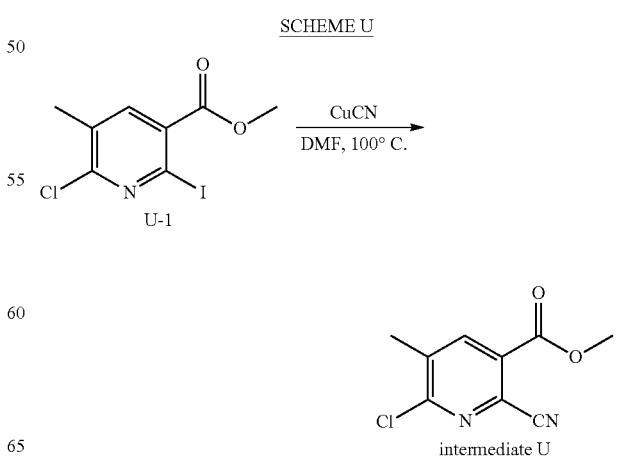

Intermediate T is prepared according to scheme T beginning with commercially available aryl halide T-1. A Miyaura borylation reaction provides boronic ester T-2 which is subsequently transformed by an oxidative hydroxylation to provide intermediate T.

Intermediate U

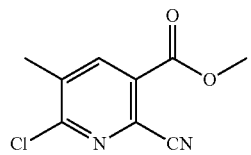

Methyl 6-chloro-2-cyano-5-methylnicotinate

Into a 20-mL microwave tube was added methyl 6-chloro-2-iodo-5-methylpyridine-3-carboxylate (2 g, 6.42 mmol), DMF (15 mL), and CuCN (850 mg, 9.60 mmol). The resulting solution was stirred for 5 min at 100° C. by microwave irradiation. The mixture was diluted with water (20 mL) and a saturated, aqueous solution of NH$_4$Cl (100 mL). Dichloromethane (2×20 mL) was used to extract the crude material and the organic layers were combined and dried over anhydrous sodium sulfate. The residue was purified by silica gel chromatography (0:1-1:8 ethyl acetate: petroleum ether) to provide the title compound. MS: 211 (M+1). $^1$H NMR (500 MHz, CDCl$_3$): δ 7.87 (s, 1H), 3.95 (s, 4H), 2.37 (s, 3H).

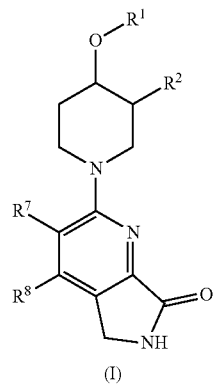

Compounds of formula (I) are synthesized from a S$_N$Ar reaction of prepared 2-chloro pyridines 1-1, and commercially available or prepared piperidines 1-2. Chloride 1-3 is then transformed to the corresponding ester 1-4 via a palladium-catalyzed carbonylation reaction. Nitrile reduction in the presence of base provides compounds of the formula (I).

SCHEME 1

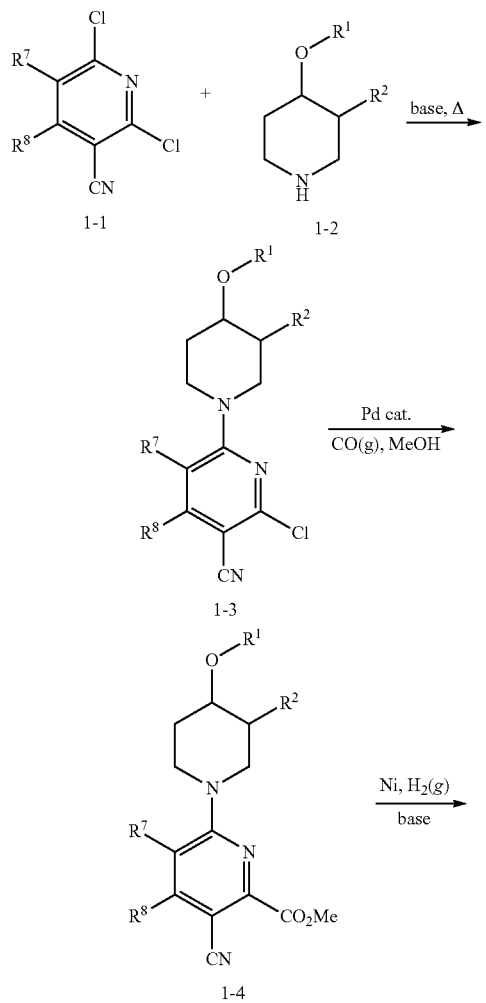

SCHEME 2

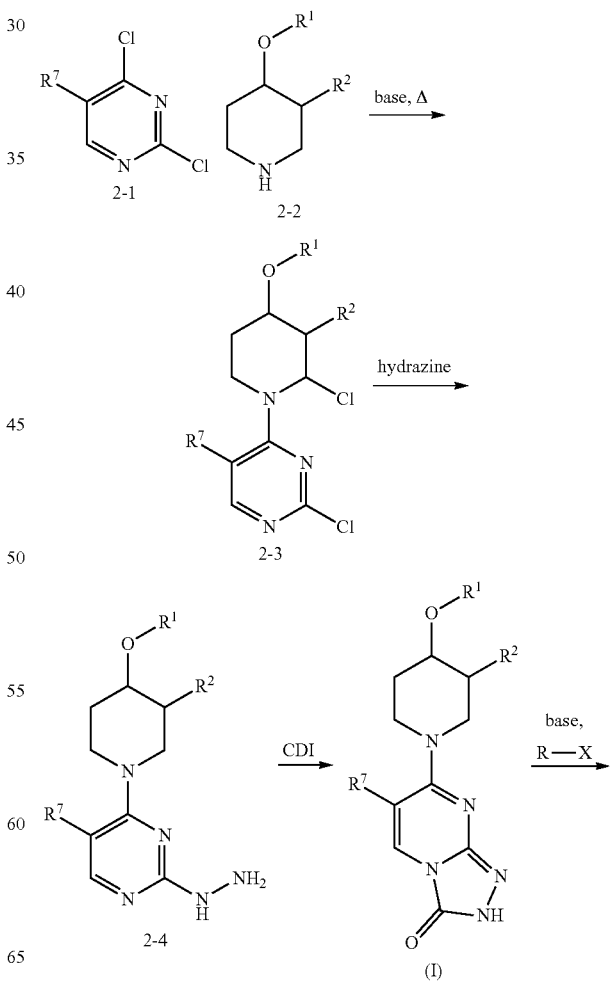

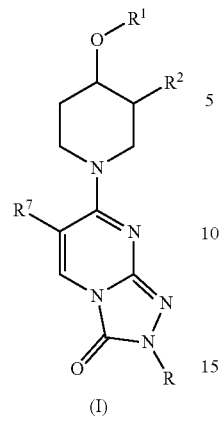

(I)

Compounds of formula (I) are synthesized via a $S_NAr$ reaction using a known 2-chloropyridine 2-1 and known or prepared piperidine 2-2. A second $S_NAr$ reaction with hydrazine provides amine adduct 2-4, which is subsequently acylated to form compound (I). Additionally, alkylation can be carried out using base in the presence of an alkyl halide.

SCHEME 4

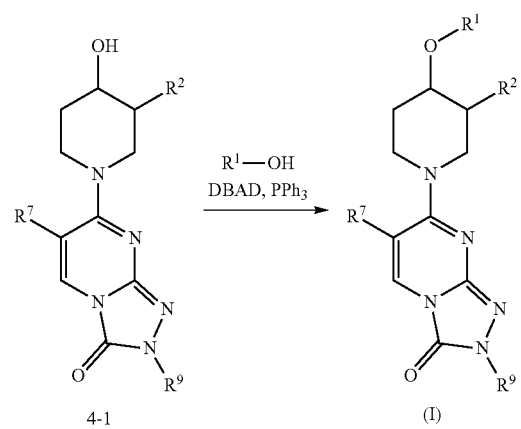

Compounds of formula (I) are synthesized from a Mitsunobu reaction using triphenyl phosphine and an azodicarboxylate with a phenol and prepared alcohol 4-1.

SCHEME 3

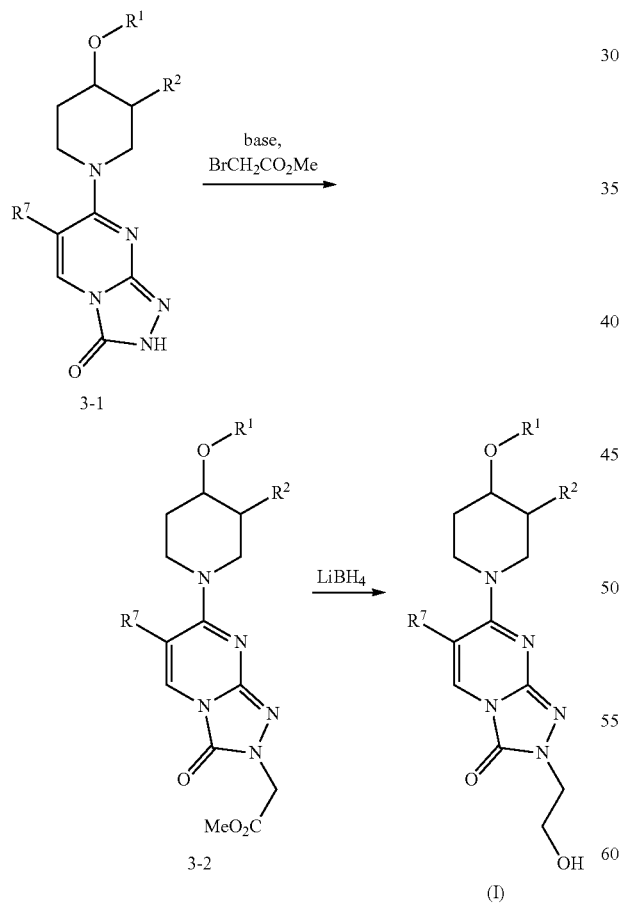

Compounds of formula (I) are synthesized from lactam 3-1, which is transformed to 3-2 via an alkylation with methyl 2-bromoacetate after treatment with base and subsequent reduction by lithium borohydride.

SCHEME 5

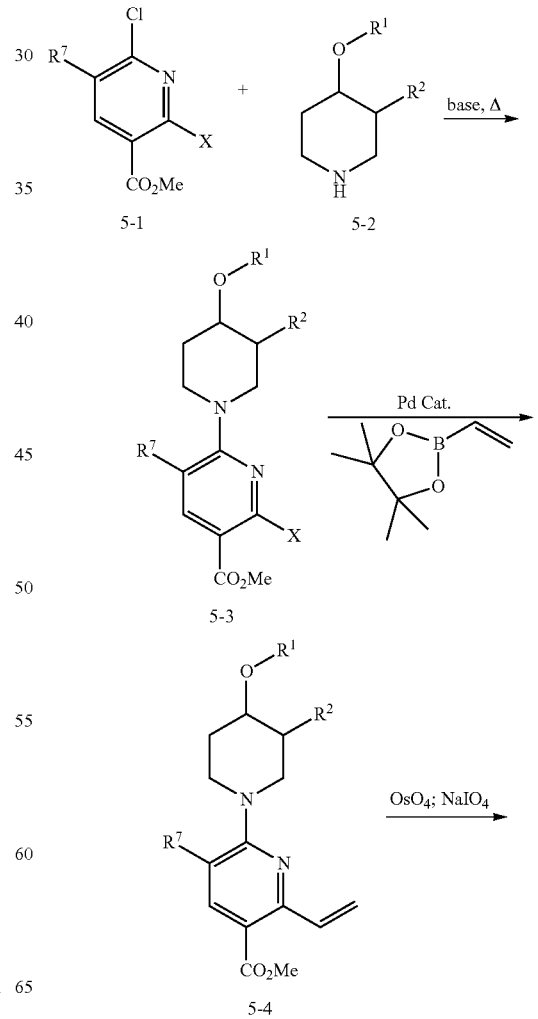

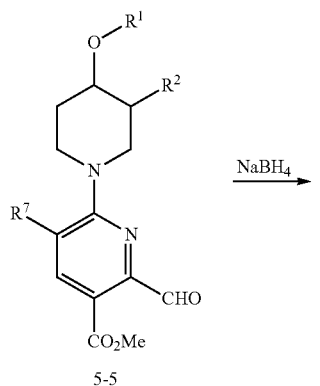

5-5

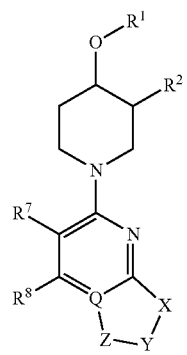

Compounds of formula (I) are synthesized via a $S_NAr$ reaction of prepared fused 2-halo pyridines 6-1 with prepared or known piperidine ether 6-2 in the presence of base.

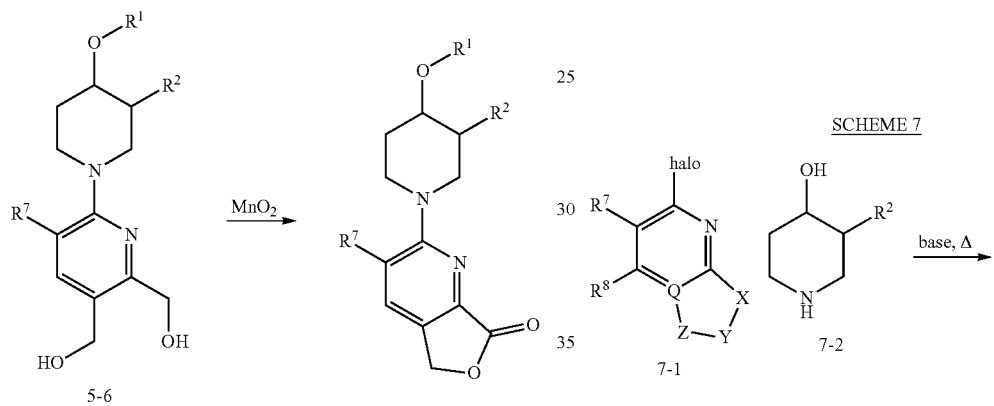

5-6

Compounds of formula (I) are synthesized from 2-halopyridine 5-1 via a $S_NAr$ reaction with a known or prepared piperidine 5-2 to provide adduct 5-3. A palladium-mediated Suzuki coupling reaction provides vinyl adduct 5-4, which is transformed via a dihydroxylation and periodate cleavage reaction to give aldehyde 5-5. Reduction of ester 5-5 can be carried out with sodium borohydride and a subsequent oxidation of diol 5-6 leads to cyclization to form the lactone in yield compounds of the formula (I).

SCHEME 7

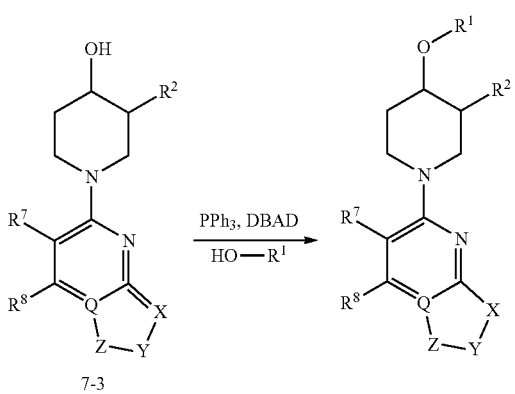

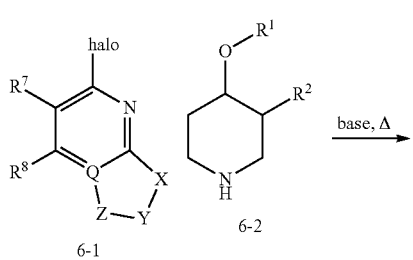

SCHEME 6

Compounds of formula (I) are synthesized from a two-step procedure of prepared pyridine 7-1 and known or prepared piperidine 7-2 and a Mitsunobu reaction of alcohol 7-3 with a known phenol.

SCHEME 8

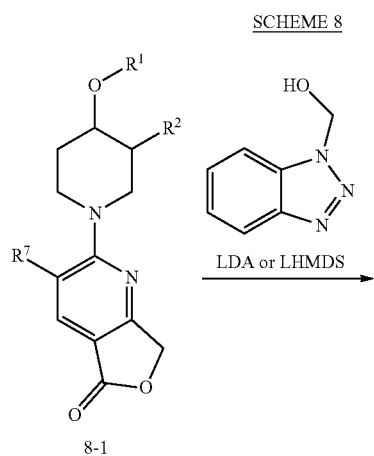

Compounds of formula (I) are synthesized from the reaction of lactone 8-1 in the presence of base with 1-hydroxy methylbenzotriazole, which generates in situ anhydrous formaldehyde.

SCHEME 9

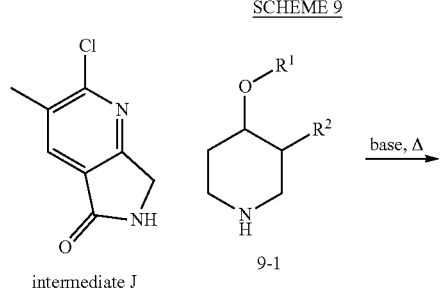

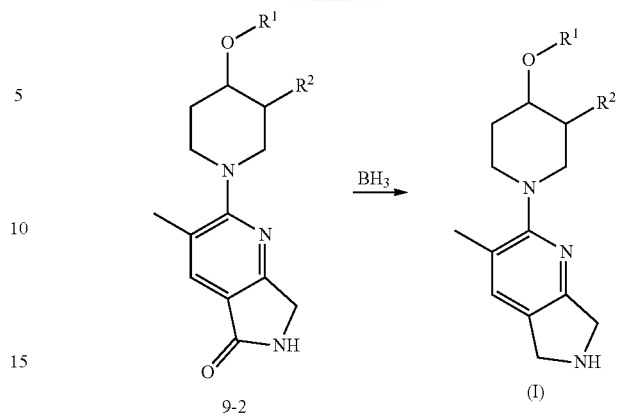

Compounds of formula (I) are synthesized from the reaction of intermediate J with prepared piperidine 9-1 by way of a $S_NAr$ reaction to form adduct 9-2 and subsequent reduction with borane.

SCHEME 10

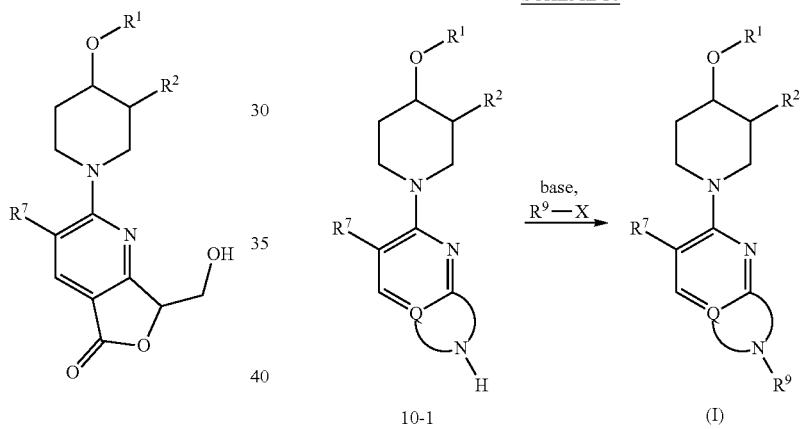

Compounds of formula (I) are synthesized from the alkylation reaction of amide or amine 10-1 in the presence of base with an electrophile.

SCHEME 11

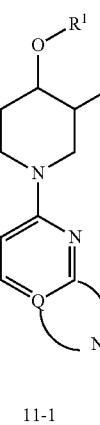

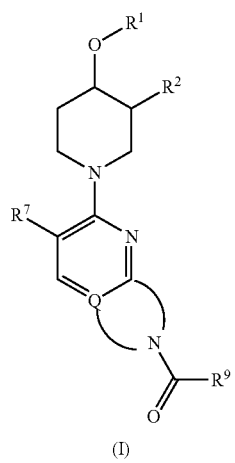

(I)

Compounds of formula (I) are synthesized from a coupling reaction of amide or amine 11-1 in the presence of HATU with a known or commercially available carboxylic acid.

SCHEME 12

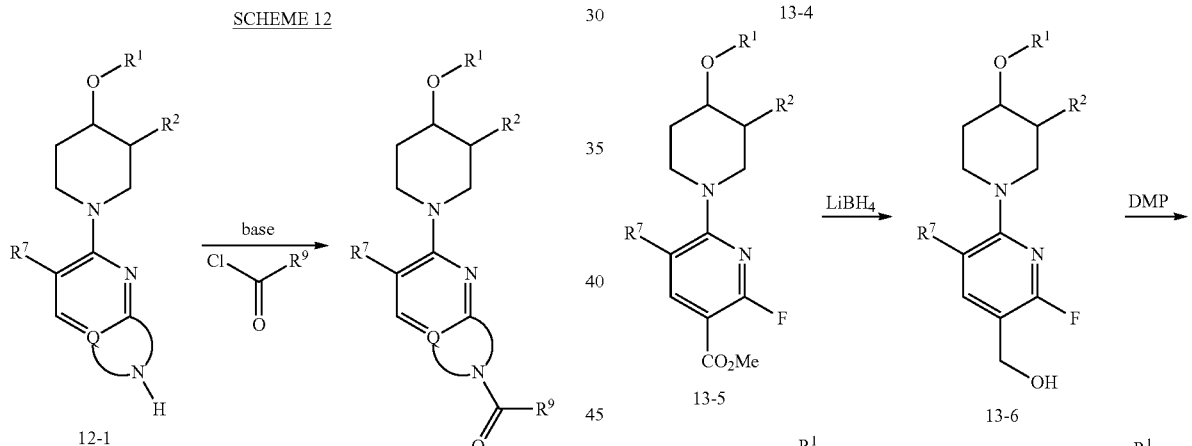

Compounds of formula (I) are synthesized via reaction of amide or amine 12-1 with a commercial acyl chloride or sulfonyl chloride in the presence of base.

SCHEME 13

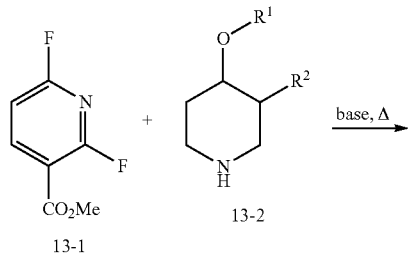

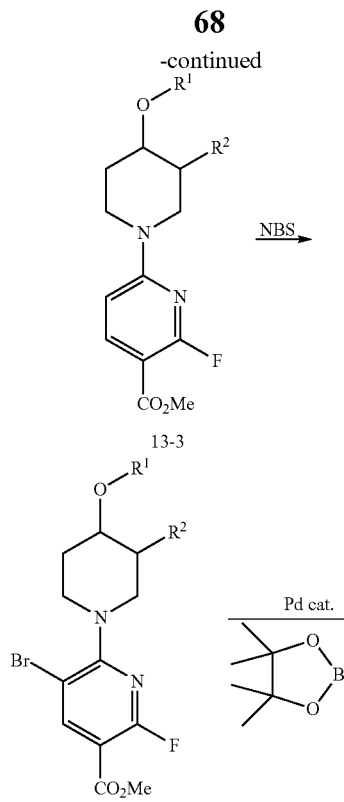

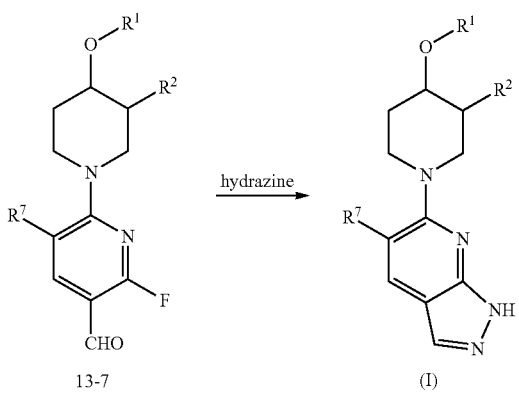

Compounds of formula (I) are synthesized from a $S_NAr$ reaction of methyl 2,6-difluoronicotinate 13-1 with a prepared piperidine 13-2. Electrophilic bromination by NBS affords bromide 14-4, which is a handle for a palladium-catalyzed Suzuki coupling reaction to provide adduct 13-5. A two-step protocol is used to reduce ester 13-5 to give aldehyde 13-7, via and intermediary alcohol 13-6. Condensation of the aldehyde 13-7 with hydrazine yields compounds having the formula (I).

SCHEME 14

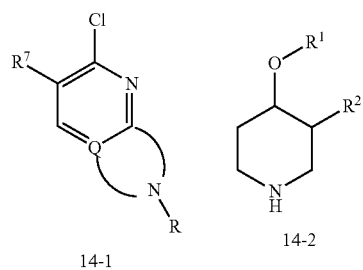

14-1    14-2

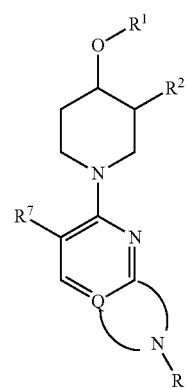

Compounds of formula (I) are synthesized via reaction 2-chloropyridine 14-1 with a prepared piperidine 14-2 via a palladium-mediated C—N coupling reaction.

SCHEME 15

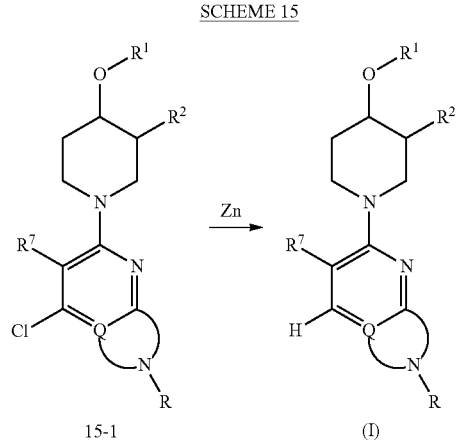

15-1    (I)

Compounds of formula (I) are synthesized via a Zn-mediated reduction of 15-1.

SCHEME 16

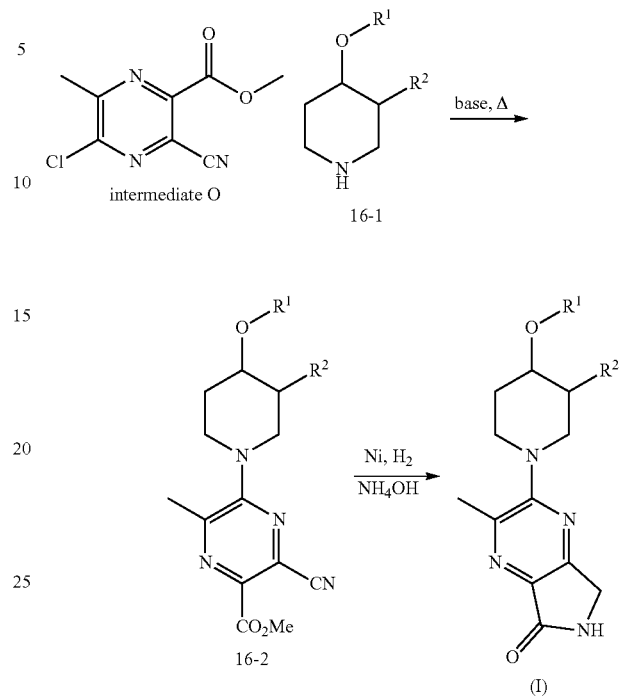

Compounds of formula (I) are synthesized via reaction of intermediate O and prepared piperidine 16-1 followed by a Ni-mediated nitrile reduction in the presence of base to elicit cyclization.

SCHEME 17

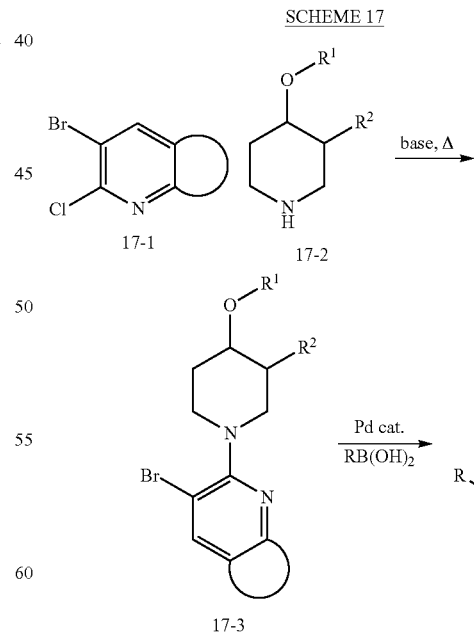

Compounds of formula (I) are synthesized via a S$_N$Ar reaction of 2-chloropyridine 17-1 with prepared piperidine 17-1 followed by a Pd-catalyzed Suzuki coupling reaction.

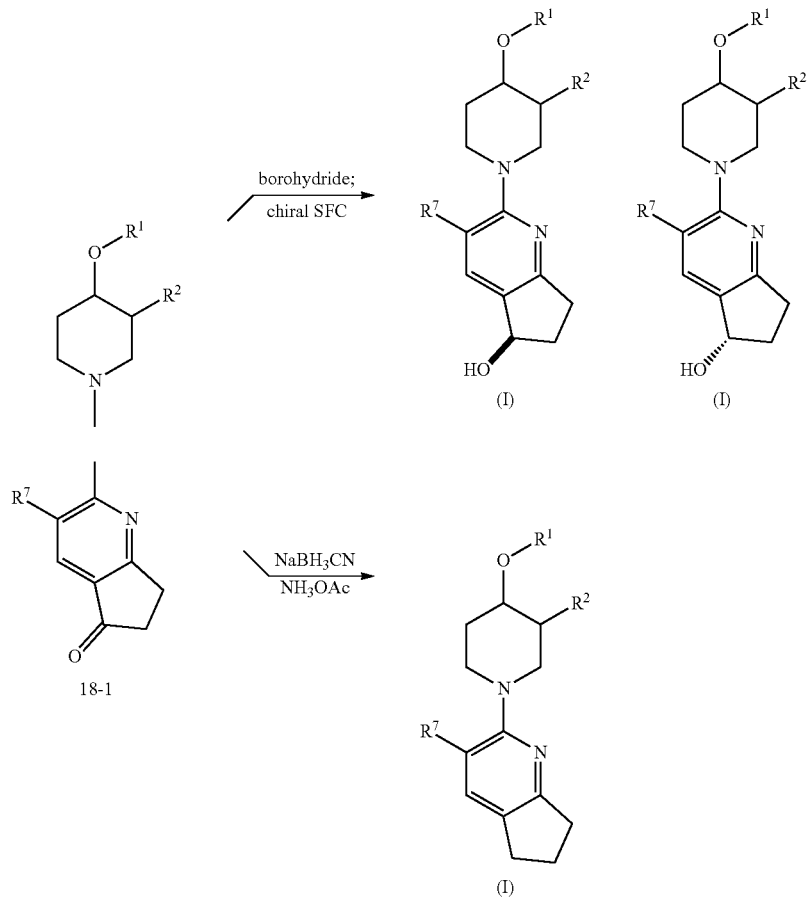
Compounds of formula (I) are prepared from ketone 18-1 and exposure to a borohydride reagent to either furnish the alcohol, followed by chiral SFC for resolution of the enantiomers, or else full reduction to the methylene product.
Compounds of formula (I) are prepared from ketone 19-1 via alkylation with an alkyl halide in the presence of base.
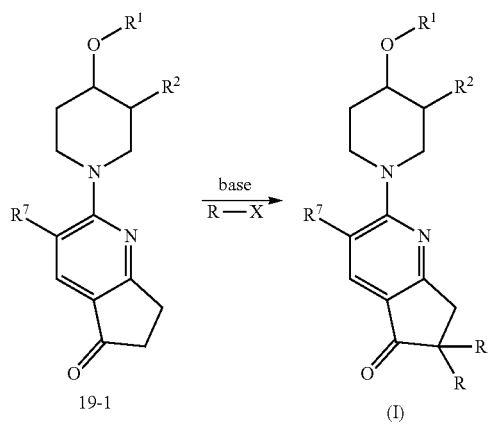
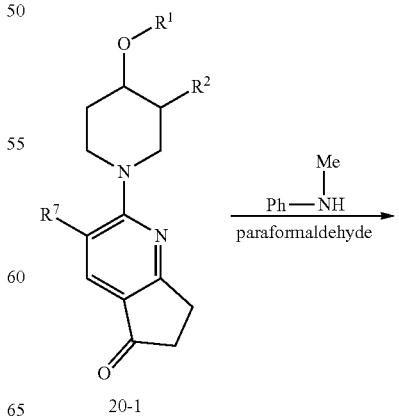

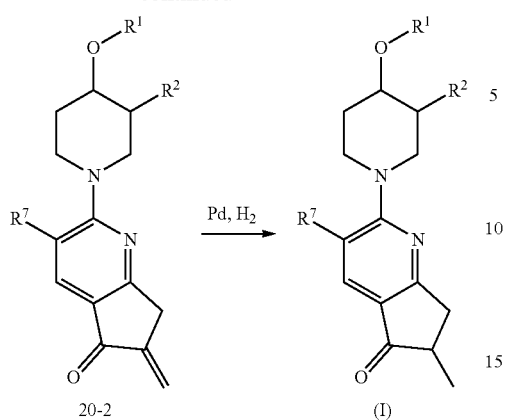

Compounds of formula (I) are synthesized from prepared ketone 20-1 and formation of an intermediary enamine in the presence of paraformaldehyde furnishes olefin 20-2, which is subsequently hydrogenated to the corresponding alkane.

SCHEME 21

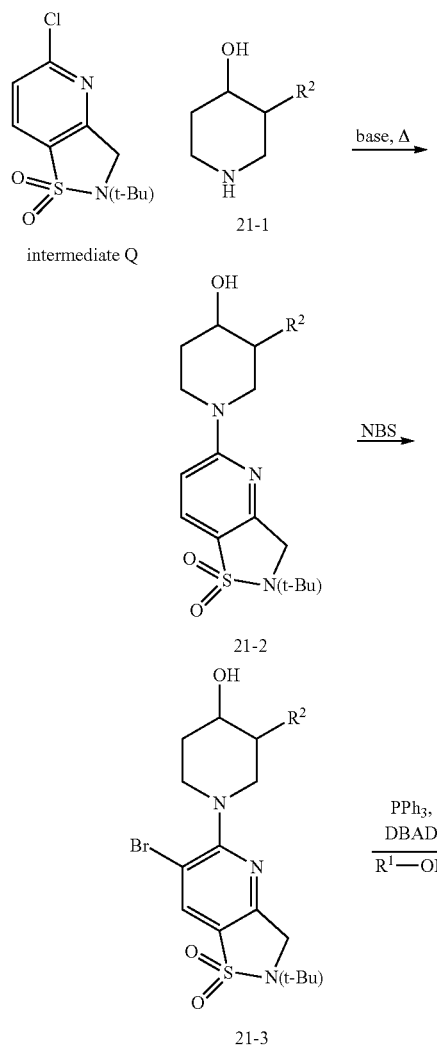

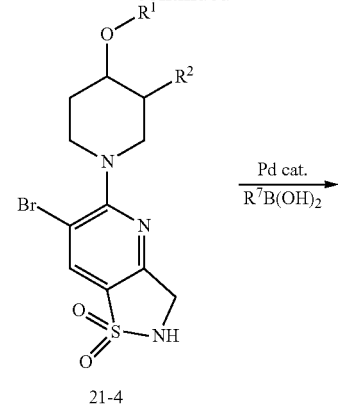

Compounds of formula (I) are prepared from intermediate Q via a S$_N$AR reaction with prepared piperidine 21-1 to furnish adduct 21-2. Electrophilic bromination with NBS installs bromide 21-3 and subsequent Mitsunobu reaction with a commercial phenol and yields ether 21-4. A Suzuki coupling reaction with bromide 21-4 provides adduct 21-5, which upon exposure to TFA yields the final deprotected product.

SCHEME 22

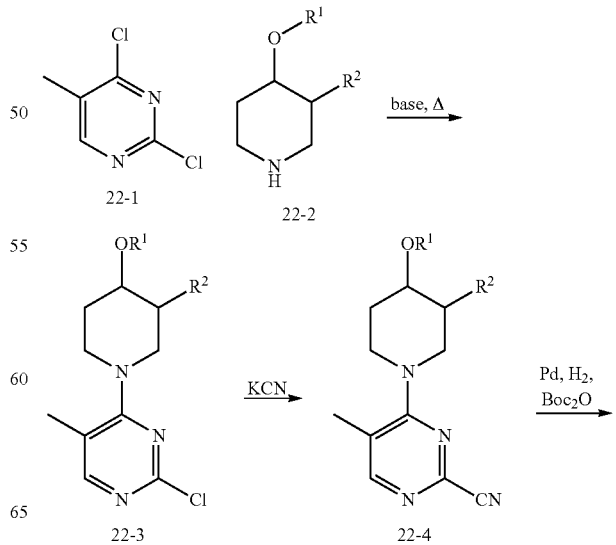

SCHEME 23

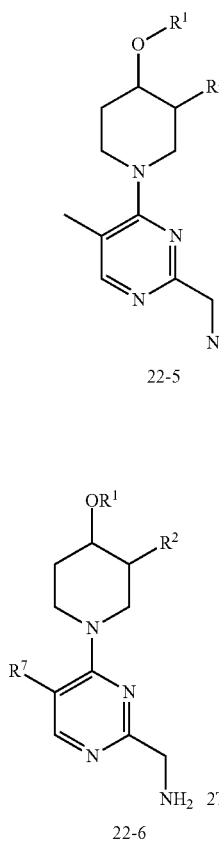

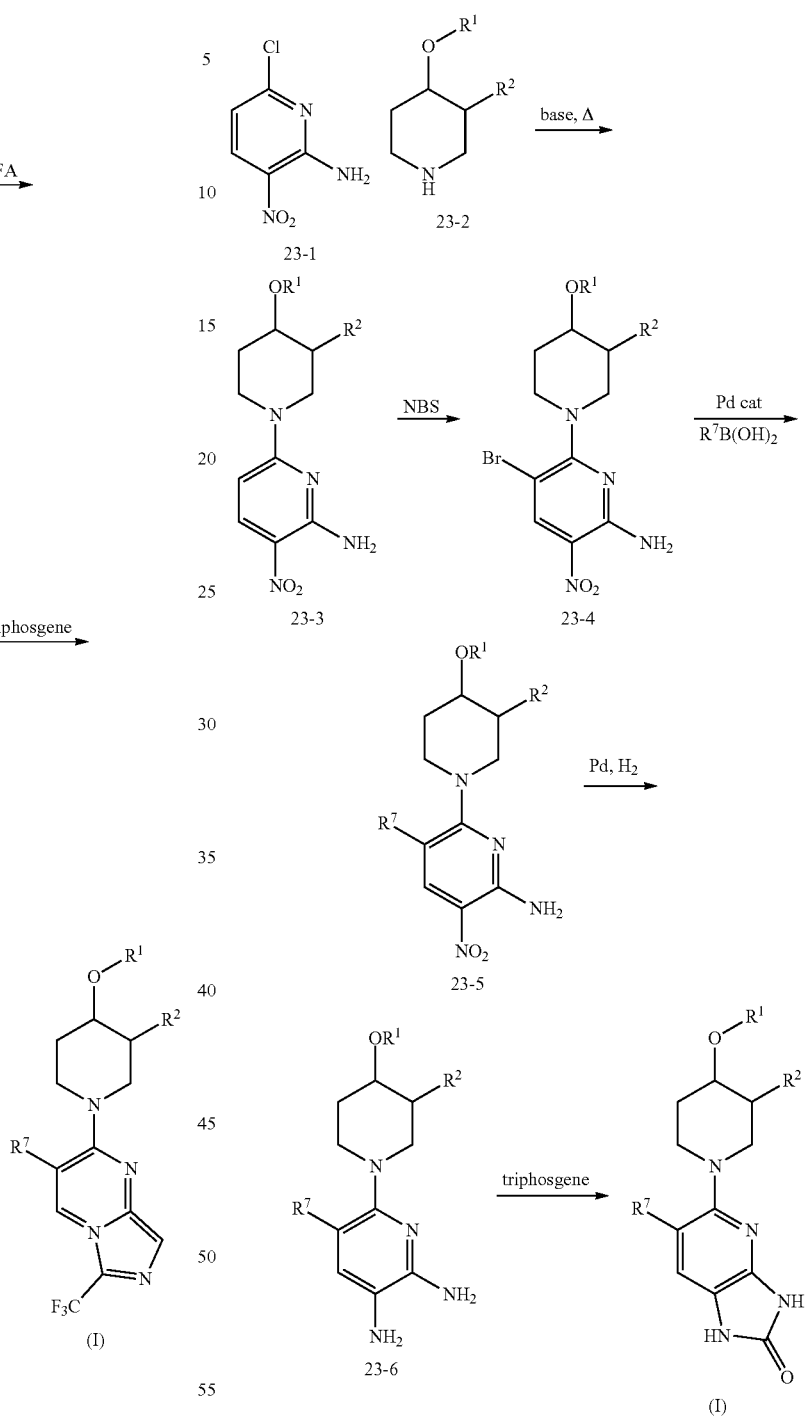

Compounds of formula (I) are prepared via a $S_NAr$ reaction with pyrimidine 22-1 and prepared piperidine 22-2 to furnish adduct 22-3. A second $S_NAr$ reaction of pyrimidine 22-3 with KCN yields nitrile 22-4. Reduction of the nitrile in the presence of di-tert-butyl dicarbonate yield the N-Boc protected amine 22-5 which is subsequently deprotected in the presence of TFA to form the TFA salt 22-6. Exposure to triphosgene provides compounds of the formula (I).

Compounds of formula (I) are prepared via a $S_NAr$ reaction with pyrimidine 23-1 and prepared piperidine 23-2 to furnish adduct 23-3. An electrophilic bromination reaction with NBS yields bromide 23-4, which is subsequently functionalized via a Suzuki coupling reaction to afford adduct 23-5. Reduction of the nitro group under the action of palladium under an atmosphere of hydrogen yields dianiline 23-6. Exposure to triphosgene provides compounds of the formula (I).

SCHEME 24
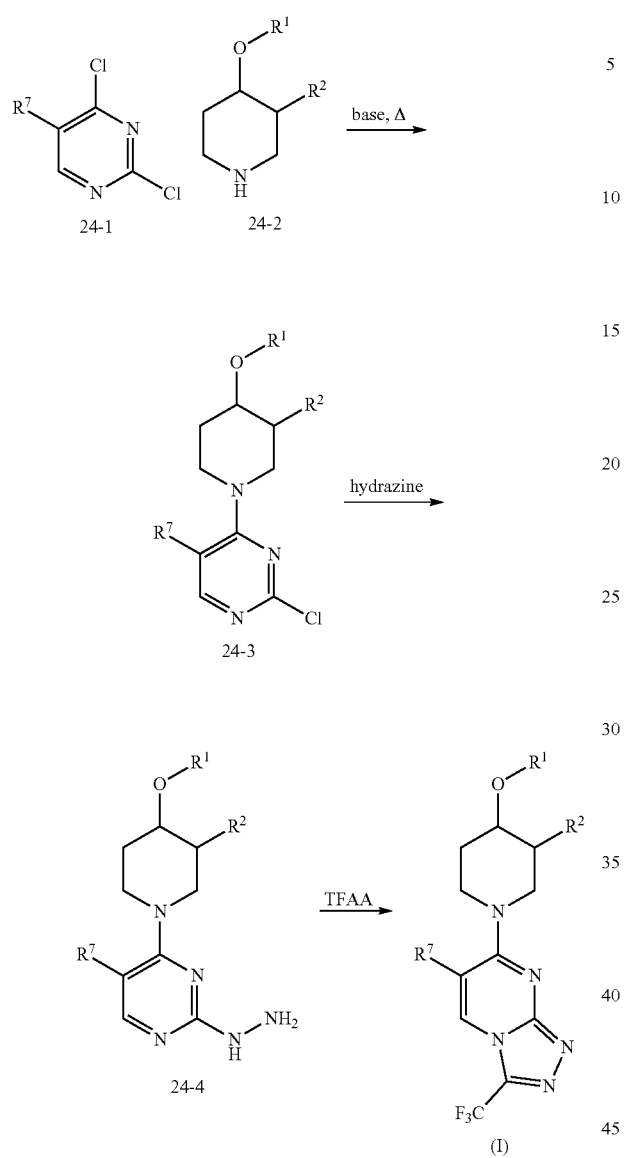
Compounds of formula (I) are synthesized via a S$_N$Ar reaction using a known 2-chloropyridine 24-1 and known or prepared piperidine 24-2. A second S$_N$Ar reaction with hydrazine provides amine adduct 24-4, which is subsequently reacted with TFFA to form compound (I).
SCHEME 25
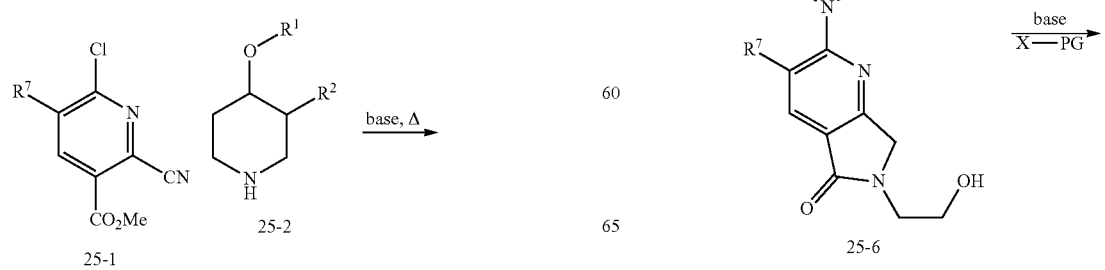

-continued

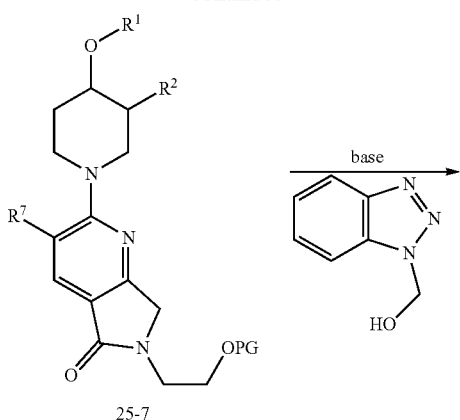

25-7

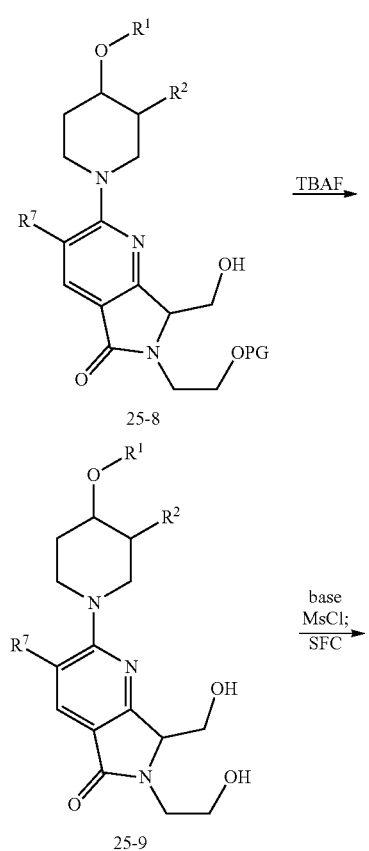

25-8

25-9

(I)

Compounds of formula (I) are synthesized via a $S_NAr$ reaction using a known 2-chloropyridine 25-1 and known or prepared piperidine 25-2. A nickel-mediated reduction of nitrile 25-3 in the presence of base elicits cyclization to form lactam 25-4. N-alkylation by methyl 2-bromoacetate in the presence of base is followed by a borohydride reduction of ester 25-5. Subsequent protection of alcohol 25-6 by a silyl-based protecting group enables the anionic reaction of 25-7 via a method for the in situ formation of anhydrous formaldehyde to yield 25-8. The deprotection of the silyl protecting group reveals diol 25-9 which undergoes activation by mesyl chloride and base to form compounds of the formula (I).

SCHEME 26

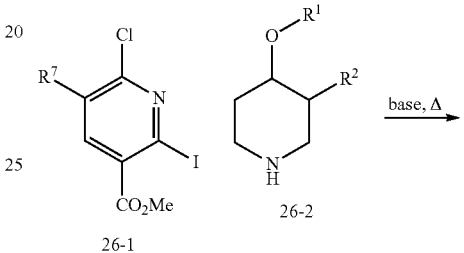

26-1    26-2

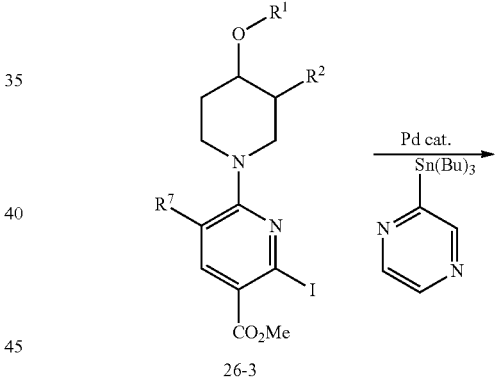

26-3

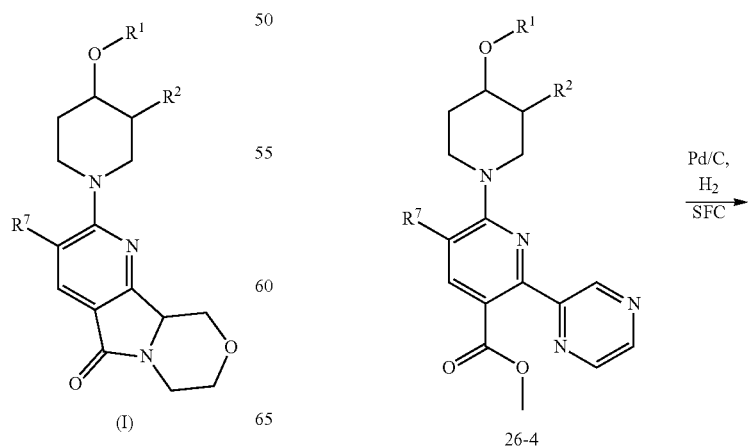

26-4

81

-continued

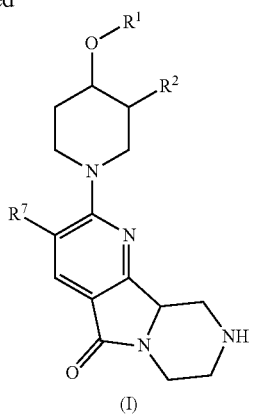

(I)

Compounds of formula (I) are synthesized via a $S_NAr$ reaction using a known 2-chloropyridine 26-1 and known or prepared piperidine 26-2. A palladium-mediated coupling reaction of iodide 26-3 with a commercially available stannane provides adduct 26-4. Reduction of pyrazine 26-4 results in a cyclization reaction to form compounds of the formula (I).

Example 1

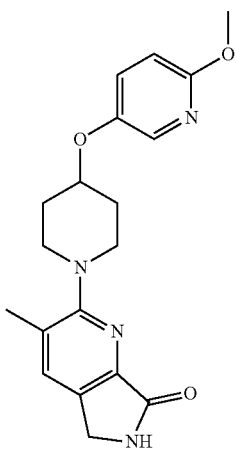

(4-((6-Methoxypyridin-3-yl)oxy)piperidin-1-yl)-3-methyl-5H-pyrrolo[3,4-b]pyridin-7(6H)-one (Scheme 1)

Step 1: 2-Chloro-6-(4-((6-methoxypyridin-3-yl)oxy)piperidin-1-yl)-5-methylnicotinonitrile To a solution of 2-methoxy-5-(piperidin-4-yloxy)pyridine hydrochloride (144 mg, 0.588 mmol) and 2,6-dichloro-5-methylnicotinonitrile (intermediate A1, 200 mg, 0.535 mmol) in DMF (2 mL) was added $K_2CO_3$ (222 mg, 1.604 mmol). The reaction was stirred at 25° C. for 2 h. The mixture was diluted with water (30 mL), extracted with EtOAc (30 mL×3) and the combined organic layers was washed with water (20 mL) then brine (20 mL). The organic was dried over anhydrous sodium sulfate, filtered and concentrated, the crude residue was purified by prep-TLC (1:1 petroleum ether:EtOAc) as the major product to provide the title compound. MS: 359 (M+1).

82

Step 2: Methyl 3-cyano-6-(4-((6-methoxypyridin-3-yl)oxy)piperidin-1-yl)-5-methylpicolinate To a solution of 2-chloro-6-(4-((6-methoxypyridin-3-yl)oxy)piperidin-1-yl)-5-methylnicotinonitrile (180 mg, 0.502 mmol) and triethylamine (0.210 mL, 1.51 mmol) in MeOH (5 mL) was added $PdCl_2(dppf)$ (367 mg, 0.502 mmol). The resulting mixture was stirred under an atmosphere of CO (50 psi) for 12 h at 50° C. The mixture was filtered, the filtrate was then concentrated and the residue was purified by prep-TLC (1:1 petroleum ether:EtOAc) to provide the title compound.

Step 3: (4-((6-Methoxypyridin-3-yl)oxy)piperidin-1-yl)-3-methyl-5H-pyrrolo[3,4-b]pyridin-7(6H)-one To a stirred solution of methyl 3-cyano-6-(4-((6-methoxypyridin-3-yl)oxy)piperidin-1-yl)-5-methylpicolinate (180 mg, 0.471 mmol) in MeOH (20 mL) was added ammonium hydroxide (16.5 mg, 0.471 mmol) and molybdenum-promoted nickel (skeletal, 72.8 mg, 0.471 mmol). The system was placed under a hydrogen atmosphere (50 psi) and was stirred for 3 h at RT. The suspension was filtered and the filtrate was concentrated and the residue was purified by reverse phase HPLC (ACN/water with 0.1% ammonium hydroxide modifier) to afford the title compound. MS: 355 (M+1). $^1$H NMR (400 MHz, methanol-$d_4$): δ 7.82 (1H, s), 7.71 (1H, s), 7.41 (1H, dd, J=8.8, 2.8 Hz), 6.73 (1H, d, J=9.2 Hz), 4.43-4.51 (1H, m), 4.34 (2H, s), 3.84 (3H, s), 3.45-3.51 (2H, m), 3.06-3.11 (2H, m), 2.40 (3H, s), 2.11-2.14 (2H, m), 1.85-1.91 (2H, m).

Example 2

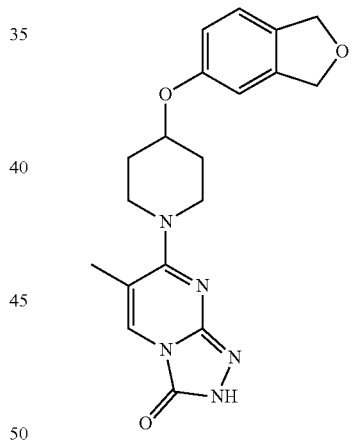

7-(4-((1,3-Dihydro-2-benzofuran-5-yl)oxy)piperidin-1-yl)-6-methyl-[1,2,4]triazolo[4,3-a]pyrimidin-3(2H)-one (Scheme 2)

Step 1: 2-Chloro-4-(4-((1,3-dihydro-2-benzofuran-5-yl)oxy)piperidin-1-yl)-5-methylpyrimidine To a solution of 2,4-dichloro-5-methylpyrimidine (191 mg, 1.173 mmol) and 4-((1,3-dihydroisobenzofuran-5-yl)oxy)piperidine, HCl (300 mg, 1.173 mmol) in DMF (5 mL) was added DIPEA (1.64 mL, 9.38 mmol). The reaction was stirred at 90° C. for 16 h before being cooled to RT and was diluted with water (10 mL). The mixture was extracted with DCM (30 mL×3) and the combined organic layers were dried over anhydrous sodium sulfate, filtered and concentrated in vacuo. The residue was purified by combiflash (0-40% EtOAc/petroleum ether) to give the title compound. MS: 346 (M+1).

Step 2: 4-(4-((1,3-Dihydroisobenzofuran-5-yl)oxy)piperidin-1-yl)-2-hydrazinyl-5-methylpyrimidine To a solution of 2-chloro-4-(4-((1,3-dihydroisobenzofuran-5-yl)oxy)piperidin-1-yl)-5-methylpyrimidine (40 mg, 0.116 mmol) in EtOH (1 mL) was added hydrazine hydrate (116 mg, 2.313 mmol) and MgSO$_4$ (278 mg, 2.31 mmol). The reaction mixture was stirred at 90° C. for 15 h before water (10 mL) was added and the mixture was extracted with DCM (10 mL×3). The combined organic fractions were washed with water (20 mL×3), dried over anhydrous sodium sulfate, filtered and concentrated to provide the title compound. MS: 342 (M+1).

Step 3: 7-(4-((1,3-Dihydro-2-benzofuran-5-yl)oxy)piperidin-1-yl)-6-methyl-[1,2,4]triazolo[4,3-a]pyrimidin-3 (2H)-one To a solution of 4-(4-((1,3-dihydroisobenzofuran-5-yl)oxy)piperidin-1-yl)-2-hydrazinyl-5-methylpyrimidine (250 mg, 0.732 mmol) in THF (5 mL) were added di(1H-imidazol-1-yl)methanone (119 mg, 0.732 mmol) and TEA (0.306 mL, 2.197 mmol). The reaction was stirred at 25° C. for 1h and was diluted with water (10 mL) and extracted with DCM (30 mL×3). The combined organic layers were dried over anhydrous sodium sulfate, filtered and concentrated in vacuo before purification by reverse phase HPLC (ACN/water with 0.1% NH$_3$OH modifier) to afford the title compound. MS: 368 (M+1). $^1$H NMR (400 MHz, CDCl$_3$): δ 7.65 (1H, s), 7.12 (1H, d, J=8.0 Hz), 6.80-6.84 (2H, m), 5.05 (4H, s), 4.49-4.57 (1H, m), 3.73-3.79 (2H, m), 3.54-3.58 (2H, m), 2.23 (3H, s), 2.03-2.09 (2H, m), 1.92-1.97 (2H, m).

Example 3

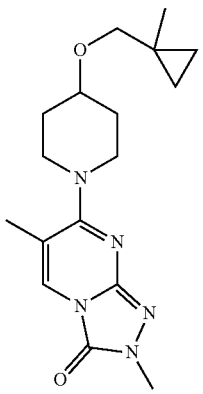 [SMILES: Cc1cn2c(=O)n(C)nc2nc1N1CCC(OCC2(C)CC2)CC1]

2,6-Dimethyl-7-(4-((1-methylcyclopropyl)methoxy)piperidin-1-yl)-[1,2,4]triazolo[4,3-a]pyrimidin-3(2H)-one (Scheme 2)

Step 1: 2-Chloro-5-methyl-4-(4-((1-methylcyclopropyl)methoxy)piperidin-1-yl)pyrimidine To a solution of 2,4-dichloro-5-methylpyrimidine (200 mg, 1.227 mmol) in DMF (10 mL) was added 4-((1-methylcyclopropyl)methoxy)piperidine, TFA (208 mg, 1.227 mmol) and K$_2$CO$_3$ (339 mg, 2.454 mmol). The reaction stirred at 60° C. for 16 h after which time the mixture was concentrated under reduced pressure. The residue was purified by silica gel chromatography (100:1-5:1 petroleum ether:EtOAc) to give the title compound. MS: 296 (M+1).

Step 2: 2-Hydrazinyl-5-methyl-4-(4-((1-methylcyclopropyl)methoxy)piperidin-1-yl)pyrimidine To a solution of 2-chloro-5-methyl-4-(4-((1-methylcyclopropyl)methoxy)piperidin-1-yl)pyrimidine (260 mg, 0.879 mmol) in EtOH (10 mL) and water (1 mL) was added hydrazine hydrate (0.128 mL, 2.64 mmol). The reaction was stirred at 80° C. for 16 h after which time the mixture was concentrated under reduced pressure. The residue was diluted with water (20 mL) and filtered and the solids were washed with water (20 mL×2) and concentrated to afford the title compound. MS: 292 (M+1).

Step 3: 6-Methyl-7-(4-((1-methylcyclopropyl)methoxy)piperidin-1-yl)-[1,2,4]triazolo[4,3-a]pyrimidin-3 (2H)-one To a solution of 2-hydrazinyl-5-methyl-4-(4-((1-methylcyclopropyl)methoxy)piperidin-1-yl)pyrimidine (160 mg, 0.549 mmol) in THF (10 mL) was added CDI (98 mg, 0.604 mmol). The reaction was stirred at 27° C. for 16 h after which time the mixture was diluted with EtOAc (10 mL), washed with water (20 mL), dried over anhydrous sodium sulfate, filtered, and concentrated in vacuo. The residue was purified by prep-TLC (EtOAc) to afford the title compound. MS: 318 (M+1).

Step 4: 2,6-Dimethyl-7-(4-((1-methylcyclopropyl)methoxy)piperidin-1-yl)-[1,2,4]triazolo[4,3-a]pyrimidin-3 (2H)-one To a solution of 6-methyl-7-(4-((1-methylcyclopropyl)methoxy)piperidin-1-yl)-[1,2,4]triazolo[4,3-a]pyrimidin-3 (2H)-one (100 mg, 0.315 mmol) in DMF (3 mL) was added NaH (60%, 12.6 mg, 0.315 mmol) at 0° C. under a nitrogen atmosphere. The reaction was stirred at 0° C. for 30 min, then MeI (0.020 mL, 0.315 mmol) was added and the mixture was stirred at 27° C. for 2 h. The volatiles were removed under reduced pressure and the residue was purified by reverse phase HPLC (ACN/water with 0.1% NH$_3$OH modifier) to furnish the title compound. MS: 332 (M+1). $^1$H NMR (400 MHz, CDCl$_3$): δ 7.29 (1H, s), 3.42-3.47 (2H, m), 3.25 (4H, s), 2.93-2.99 (4H, m), 1.89 (3H, s), 1.62-1.67 (2H, m), 1.36-1.43 (2H, m), 0.82 (3H, s), 0.02-0.85 (4H, m).

The following examples in table 2 were prepared according to scheme 2 using the procedure outlined in the synthesis of Examples 2 and 3 using known or prepared intermediates. In some examples, step 4 may be omitted.

TABLE 2

| Example | Structure | Name | MS (M + 1) |
|---|---|---|---|
| 4 | 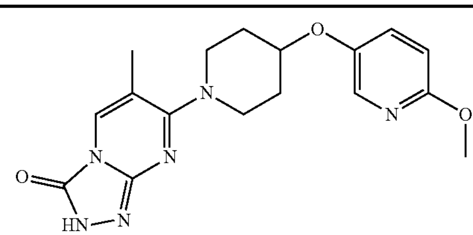 | 7-(4-((6-methoxypyridin-3-yl)oxy)piperidin-1-)yl)-6-methyl-[1,2,4]triazolo[4,3-a]pyrimidin-3(2H)-one | 357 |

TABLE 2-continued

| Example | Structure | Name | MS (M + 1) |
|---|---|---|---|
| 5 | 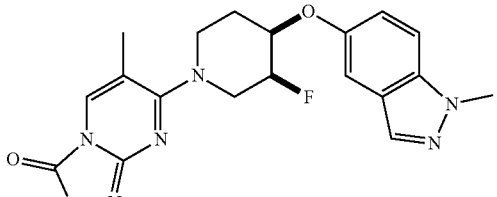 | 7-((3S,4R)-3-fluoro-4-((1-methyl-1H-indazol-5-yl)oxy)piperidin-1-yl)-6-methyl-[1,2,4]triazolo[4,3-a]pyrimidin-3(2H)-one | 398 |
| 6 | 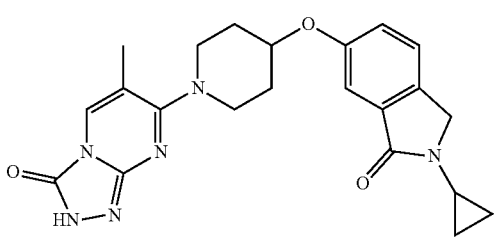 [SMILES: Cc1cn2c(=O)[nH]nc2nc1N1CCC(Oc2ccc3c(c2)C(=O)N(C2CC2)C3)CC1] | 7-(4-((2-cyclopropyl-3-oxoisoindolin-5-yl)oxy)piperidin-1-yl)-6-methyl-[1,2,4]triazolo[4,3-a]pyrimidin-3(2H)-one | 421 |
| 7 | 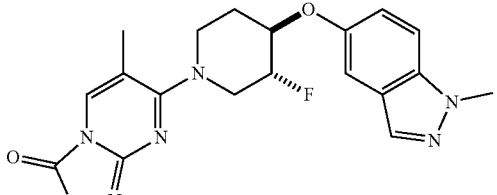 | 7-((3R,4R)-3-fluoro-4-((1-methyl-1H-indazol-5-yl)oxy)piperidin-1-yl)-6-methyl-[1,2,4]triazolo[4,3-a]pyrimidin-3(2H)-one | 398 |
| 8 | 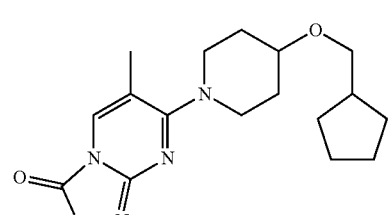 | 7-(4-(cyclopentylmethoxy)piperidin-1-yl)-6-methyl-[1,2,4]triazolo[4,3-a]pyrimidin-3(2H)-one | 332 |
| 9 | 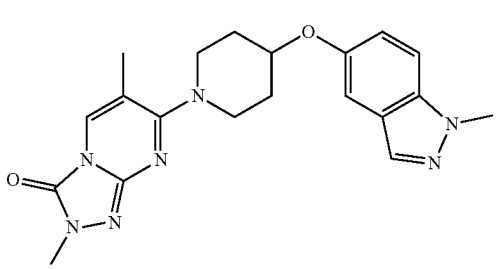 [SMILES: Cc1cn2c(=O)n(C)nc2nc1N1CCC(Oc2ccc3c(cnn3C)c2)CC1] | 2,6-dimethyl-7-(4-((1-methyl-1H-indazol-5-yl)oxy)piperidin-1-yl)-[1,2,4]triazolo[4,3-a]pyrimidin-3(2H)-one | 394 |
| 10 | 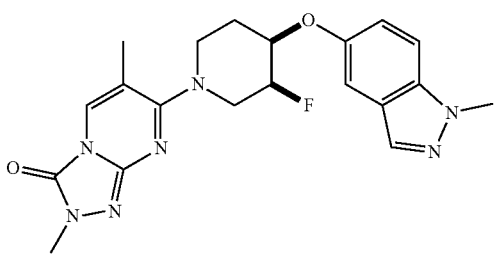 | 7-((3S,4R)-3-fluoro-4-((1-methyl-1H-indazol-5-yl)oxy)piperidin-1-yl)-2,6-dimethyl-[1,2,4]triazolo[4,3-a]pyrimidin-3(2H)-one | 412 |

TABLE 2-continued

| Example | Structure | Name | MS (M + 1) |
|---|---|---|---|
| 11 | 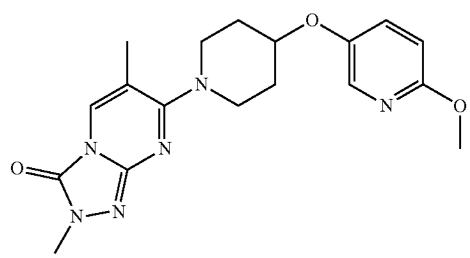 [SMILES: COc1ccc(OC2CCN(c3nc4nn(C)c(=O)n4cc3C)CC2)cn1] | 7-(4-((6-methoxypyridin-3-yl)oxy)piperidin-1-yl)-2,6-dimethyl-[1,2,4]triazolo[4,3-a]pyrimidin-3(2H)-one | 371 |
| 12 | 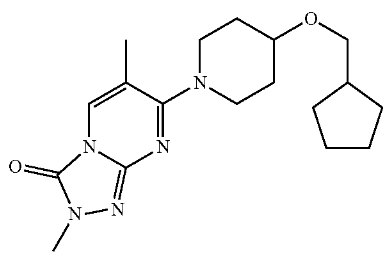 [SMILES: Cc1cn2c(=O)n(C)nc2nc1N1CCC(OCC2CCCC2)CC1] | 7-(4-(cyclopentylmethoxy)piperidin-1-yl)-2,6-dimethyl-[1,2,4]triazolo[4,3-a]pyrimidin-3(2H)-one | 346 |

Example 13

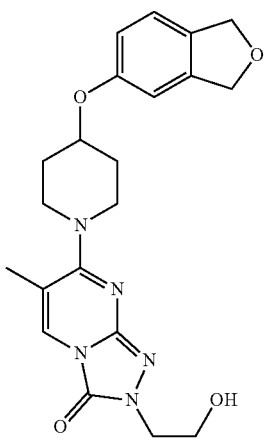 [SMILES: Cc1cn2c(=O)n(CCO)nc2nc1N1CCC(Oc2ccc3c(c2)COC3)CC1]

7-(4-((1,3-Dihydro-2-benzofuran-5-yl)oxy)piperidin-1-yl)-2-(2-hydroxyethyl)-6-methyl-[1,2,4]triazolo[4,3-a]pyrimidin-3(2H)-one (Scheme 3)

Step 1: Methyl 2-(7-(4-((1,3-dihydro-2-benzofuran-5-yl)oxy)piperidin-1-yl)-6-methyl-3-oxo-[1,2,4]triazolo[4,3-a]pyrimidin-2(3H)-yl)acetate To a solution of 7-(4-((1,3-dihydro-2-benzofuran-5-yl)oxy)piperidin-1-yl)-6-methyl-[1,2,4]triazolo[4,3-a]pyrimidin-3(2H)-one (190 mg, 0.517 mmol) in THF (3 mL) was added sodium hydride (24.8 mg, 1.03 mmol). The reaction was stirred for 5 min at RT and methyl 2-bromoacetate (396 mg, 2.59 mmol) was added. The reaction was stirred at 25° C. for 16 h and was quenched with water (10 mL) and extracted with DCM (30 mL×3). The combined organic layers were dried over anhydrous sodium sulfate, filtered, concentrated in vacuo. The residue was purified by silica gel chromatography (40-80% THF in petroleum ether) to yield the title compound. MS: 440 (M+1).

Step 2: 7-(4-((1,3-Dihydro-2-benzofuran-5-yl)oxy)piperidin-1-yl)-2-(2-hydroxyethyl)-6-methyl-[1,2,4]triazolo[4,3-a]pyrimidin-3(2H)-one To a solution of methyl 2-(7-(4-((1,3-dihydro-2-benzofuran-5-yl)oxy)piperidin-1-yl)-6-methyl-3-oxo-[1,2,4]triazolo[4,3-a]pyrimidin-2(3H)-yl)acetate (90 mg, 0.205 mmol) in THF (3 mL) was added lithium borohydride (6.69 mg, 0.307 mmol). The reaction was stirred at 25° C. for 1 h and was then quenched with MeOH (5 mL) and concentrated in vacuo. The residue was purified by reverse phase HPLC (ACN/water with 0.1% $NH_3OH$ modifier) to afford the title compound. MS: 412 (M+1). $^1H$ NMR (400 MHz, $CDCl_3$): δ 7.65 (1H, s), 7.15 (1H, d, J=8.4 Hz), 6.85 (1H, d, J=8.4 Hz), 6.82 (1H, s), 5.08 (4H, d, J=3.2 Hz), 4.54-4.61 (1H, m), 4.07-4.12 (2H, m), 3.94-4.03 (2H, m), 3.71-3.82 (2H, m), 3.48-3.58 (2H, m), 3.10-3.16 (1H, m), 2.24 (3H, s), 2.04-2.13 (2H, m), 1.92-1.99 (2H, m).

The following examples in table 3 were prepared according to scheme 3 using the procedure outlined in the synthesis of Example 13.

TABLE 3

| Example | Structure | Name | MS (M + 1) |
|---|---|---|---|
| 14 | 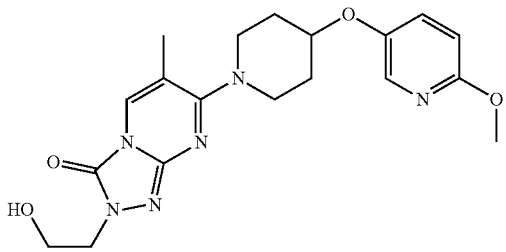 [SMILES: COc1ccc(OC2CCN(c3nc4nn(CCO)c(=O)n4cc3C)CC2)cn1] | 2-(2-hydroxyethyl)-7-(4-((6-methoxypyridin-3-yl)oxy)piperidin-1-yl)-6-methyl-[1,2,4]triazolo[4,3-a]pyrimidin-3(2H)-one | 401 |

Example 15

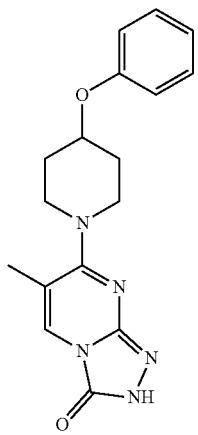 [SMILES: Cc1cn2c(=O)[nH]nc2nc1N1CCC(Oc2ccccc2)CC1]

15

6-Methyl-7-(4-phenoxypiperidine-1-yl)-[1.2.4]triazolo[4,3-a]pyrimidin-3(2H)-one (Scheme 4)

A solution of 7-(4-hydroxypiperidin-1-yl)-6-methyl-[1,2,4]triazolo [4,3-a]pyrimidin-3(2H)-one (200 mg, 0.80 mmol) in THF (15 mL) was added (E)-di-tert-butyl diazene-1,2-dicarboxylate (277 mg, 1.204 mmol), triphenylphosphine (316 mg, 1.20 mmol) and phenol (91 mg, 0.96 mmol). The mixture was stirred at 70° C. for 16 h before removing the volatiles and direct purification by reverse phase HPLC (ACN/water with 0.1% TFA modifier) to afford the title compound. MS: 326 (M+1). $^1$H NMR (400 MHz, methanol-d$_4$): δ 7.77 (1H, s), 7.25-7.28 (2H, m), 6.89-7.02 (3H, m), 4.62-4.66 (1H, m), 3.76-3.83 (2H, m), 3.45-3.53 (2H, m), 2.26 (3H, s), 2.05-2.15 (2H, m), 1.82-1.92 (2H, m).

The following examples in table 4 were prepared according to scheme 4 using the procedure outlined in the synthesis of Example 15 with known or commercial phenols.

TABLE 4

| Example | Structure | Name | MS (M + 1) |
|---|---|---|---|
| 16 | 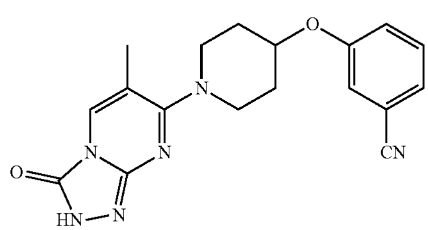 [SMILES: Cc1cn2c(=O)[nH]nc2nc1N1CCC(Oc2cccc(C#N)c2)CC1] | 3-((1-(6-methyl-3-oxo-2,3-dihydro-[1,2,4]triazolo[4,3-a]pyrimidin-7-yl)piperidin-4-yl)oxy)benzonitrile | 351 |
| 17 | 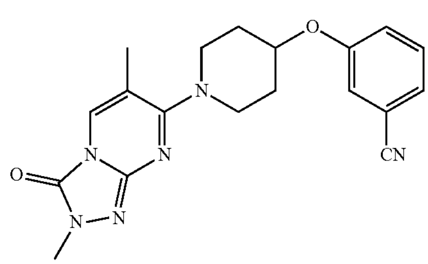 [SMILES: Cc1cn2c(=O)n(C)nc2nc1N1CCC(Oc2cccc(C#N)c2)CC1] | 3-((1-(2,6-dimethyl-3-oxo-2,3-dihydro-[1,2,4]triazolo[4,3-a]pyrimidin-7-yl)piperidin-4-yl)oxy)benzonitrile | 365 |

TABLE 4-continued

| Example | Structure | Name | MS (M + 1) |
|---|---|---|---|
| 18 | 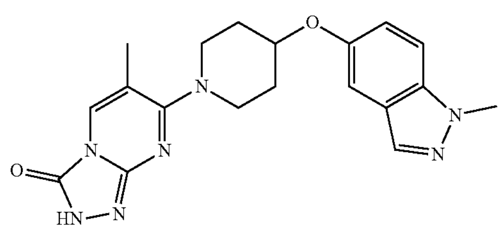 [SMILES: Cc1cn2c(=O)[nH]nc2nc1N1CCC(Oc2ccc3c(cnn3C)c2)CC1] | 3-((1-(6-methyl-3-oxo-2,3-dihydro-[1,2,4]triazolo[4,3-a]pyrimidin-7-yl)piperidin-4-yl)oxy)benzonitrile | 380 |
| 19 | 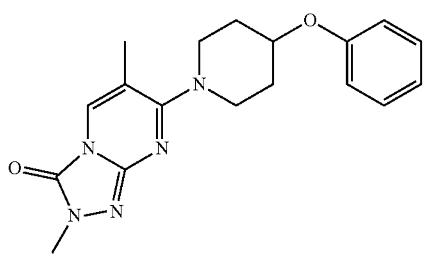 [SMILES: Cc1cn2c(=O)n(C)nc2nc1N1CCC(Oc2ccccc2)CC1] | 2,6-dimethyl-7-(4-phenoxypiperidin-1-yl)-[1,2,4]triazolo[4,3-a]pyrimidin-3(2H)-one | 340 |

Example 20

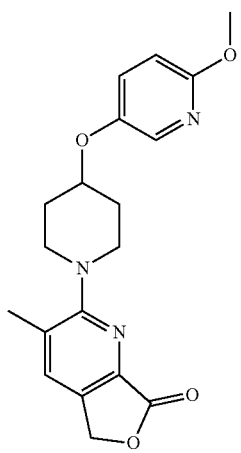

2-(4-((6-Methoxypyridin-3-yl)oxy)piperidin-1-yl)-3-methylfuro[3,4-b]pyridin-7(5H)-one (Scheme 5)

Step 1: Methyl 2-iodo-6-(4-((6-methoxypyridin-3-yl)oxy)piperidin-1-yl)-5-methylnicotinate To methyl 6-chloro-2-iodo-5-methylnicotinate (prepared according to literature procedure, see e.g.: Vanlaer, S., et al. *Eur. J. Org. Chem.* 2008, 15, 2571-2581) (987 mg, 3.17 mmol), 2-methoxy-5-(piperidin-4-yloxy)pyridine (600 mg, 2.88 mmol) in DMF (5 mL) was added $K_2CO_3$ (1195 mg, 8.64 mmol). The reaction was stirred at 70° C. for 8 h and was cooled to Rt before diluting with water (7 mL) and extracting with EtOAc (30 mL×3). The combined organic layers were washed with brine (8 mL), dried over anhydrous $Na_2SO_4$, filtered and concentrated under reduced pressure. The residue was purified by prep-TLC (3:1 petroleum ether: EtOAc) to afford the title compound as the minor regioisomeric product. MS: 484 (M+1).

Step 2: Methyl 6-(4-((6-methoxypyridin-3-yl)oxy)piperidin-1-yl)-5-methyl-2-vinylnicotinate To a solution of methyl 2-iodo-6-(4-((6-methoxypyridin-3-yl)oxy)piperidin-1-yl)-5-methylnicotinate (800 mg, 0.91 mmol) in dioxane (7 mL) and water (0.7 mL) was added 4,4,5,5-tetramethyl-2-vinyl-1,3,2-dioxaborolane (211 mg, 1.37 mmol), $K_2CO_3$ (316 mg, 2.29 mmol), $PdCl_2(dppf)$ (66.9 mg, 0.091 mmol). The reaction was stirred under a nitrogen atmosphere at 90° C. for 8 h. After cooling to RT, the mixture was diluted with water (20 mL) and was extracted with EtOAc (20 mL×3). The combined organic layers were washed with brine (25 mL), dried over anhydrous sodium sulfate, filtered and concentrated under reduced pressure. The residue was purified by prep-TLC (2.5:1 petroleum ether:EtOAc) to afford the title compound. MS: 384 (M+1).

Step 3: Methyl 2-formyl-6-(4-((6-methoxypyridin-3-yl)oxy) piperidin-1-yl)-5-methylnicotinate To a solution of methyl 6-(4-((6-methoxypyridin-3-yl) oxy)piperidin-1-yl)-5-methyl-2-vinylnicotinate (100 mg, 0.261 mmol) in THF (1 mL) and water (1 mL) at 15° C. was added osmium tetroxide (99 mg, 0.391 mmol). The mixture was stirred at 15° C. for 5 min, then sodium periodate (84 mg, 0.391 mmol) was added at this temperature. The mixture was stirred at 30° C. for 8 h before being diluted with water (7 mL), and extracted with EtOAc (30 mL×3). The combined organic layers were washed with brine (8 mL), dried over anhydrous sodium sulfate, filtered and concentrated under reduced pressure to provide the title compound. MS: 386 (M+1).

Step 4: (6-(4-((6-Methoxypyridin-3-yl)oxy)piperidin-1-yl)-5-methylpyridine-2,3-diyl)dimethanol To a solution of methyl 2-formyl-6-(4-((6-methoxypyridin-3-yl)oxy)piperidin-1-yl)-5-methylnicotinate (35 mg, 0.091 mmol) in THF (4 mL) was added NaBH$_4$ (3.44 mg, 0.091 mmol) at 0° C. The reaction was stirred at 20° C. for 1 h and was then poured into aqueous ammonium chloride (saturated, 7 mL). The mixture was extracted with DCM (20 mL×3), dried over anhydrous sodium sulfate, filtered and the filtrate was concentrated in vacuo to give the title compound MS: 360 (M+1).

Step 5: 2-(4-((6-Methoxypyridin-3-yl)oxy)piperidin-1-yl)-3-methylfuro[3,4-b]pyridin-7(5H)-one To (6-(4-((6-methoxypyridin-3-yl)oxy)piperidin-1-yl)-5-methylpyridine-2,3-diyl)dimethanol (30 mg, 0.083 mmol) in DCM (3 mL) was added manganese dioxide (43.5 mg, 0.501 mmol). The mixture was stirred at 20° C. for 8 h before adding water (7 mL) and extracting the product with EtOAc (8 mL×3). The combined organic layers were washed with brine (8 mL), dried over anhydrous sodium sulfate, filtered and concentrated under reduced pressure. The residue was purified by reverse phase HPLC (ACN/water with 0.1% TFA modifier) to afford the title compound. MS: 356 (M+1). $^1$H NMR (400 MHz, methanol-d$_4$): δ 7.89 (1H, s), 7.78 (1H, s), 7.53 (1H, dd, J=9.2, 2.4 Hz), 6.85 (1H, d, J=9.2 Hz), 5.33 (2H, s), 4.49-4.51 (1H, m), 3.91 (3H, s), 3.49-3.54 (2H, m), 3.08-3.20 (2H, m), 2.48 (3H, s), 2.12-2.17 (2H, m), 1.91-1.97 (2H, m).

Example 21

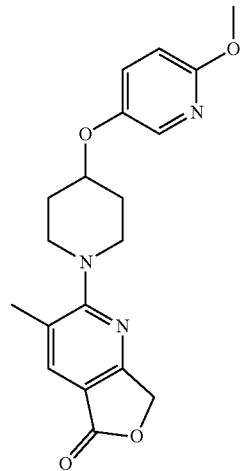

2-(4-((6-Methoxypyridin-3-yl)oxy)piperidin-1-yl)-3-methylfuro[3,4-b]pyridin-5(7H)-one (Scheme 6)

Step 1: Methyl 2-iodo-6-(4-((6-methoxypyridin-3-yl)oxy) piperidin-1-yl)-5-methylnicotinate A solution of 2-chloro-3-methylfuro[3,4-b]pyridin-5 (7H)-one (intermediate E-1, 15 mg, 0.082 mmol) and 2-methoxy-5-(piperidin-4-yloxy)pyridine (170 mg, 0.817 mmol) in DMF (1 mL) was stirred at 140° C. for 2 h. After cooling, the mixture was diluted with MeOH (2 mL) was directly purified by reverse phase HPLC (ACN/water with 0.1% HCl modifier) to afford the title compound. MS: 356 (M+1). $^1$H NMR (400 MHz, methanol-d$_4$): δ 8.24 (1H, dd, J=9.6, 2.8 Hz), 8.15 (1H, d, J=2.8 Hz), 7.92 (1H, s), 7.55 (1H, d, J=9.6 Hz), 5.47 (2H, s), 4.75-4.81 (1H, m), 4.18 (3H, s), 3.72-3.78 (2H, m), 3.42-3.48 (2H, m), 2.42 (3H, s), 2.17-2.23 (2H, m), 1.94-2.01 (2H, m).

The following examples in table 6 were prepared according to scheme 6 using the procedure outlined in the synthesis of Example 21.

TABLE 6

| Example | Structure | Name | MS (M + 1) |
|---|---|---|---|
| 22 | 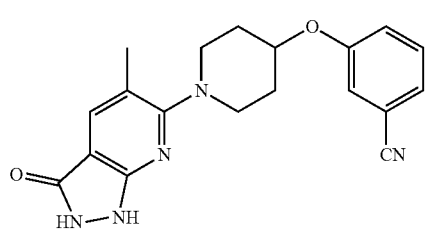 [SMILES: Cc1cc2c(=O)[nH][nH]c2nc1N1CCC(Oc2cccc(C#N)c2)CC1] | 3-((1-(5-methyl-3-oxo 2,3-dihydro-1H-pyrazolo[3,4-b]pyridin-6-yl)piperidin-4-yl)oxy)benzonitrile | 350 |

TABLE 6-continued

| Example | Structure | Name | MS (M + 1) |
|---|---|---|---|
| 23 | 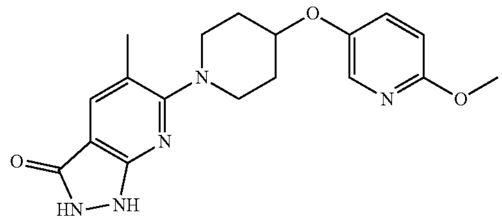 [SMILES: COc1ccc(OC2CCN(c3nc4[nH][nH]c(=O)c4cc3C)CC2)cn1] | 6-(4-((6-methoxypyridin-3-yl)oxy)piperidin-1-yl)-5-methyl-1,2-dihydro-3H-pyrazolo[3,4-b]pyridin-3-one | 356 |
| 24 | 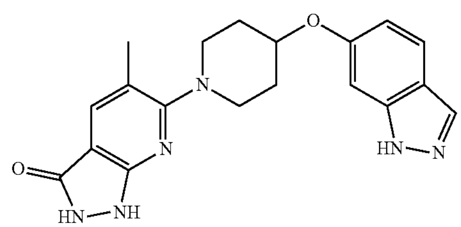 [SMILES: Cc1cc2c(=O)[nH][nH]c2nc1N1CCC(Oc2ccc3cn[nH]c3c2)CC1] | 6-(4-((1H-indazol-6-yl)oxy)piperidin-1-yl)-5-methyl-1,2-dihydro-3H-pyrazolo[3,4-b]pyridin-3-one | 365 |
| 25 | 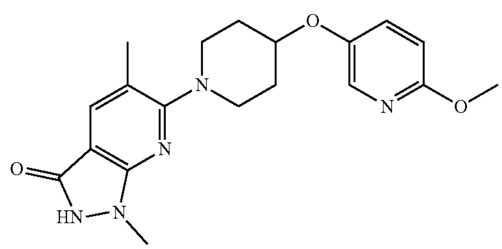 [SMILES: COc1ccc(OC2CCN(c3nc4c(cc3C)c(=O)[nH]n4C)CC2)cn1] | 6-(4-((6-methoxypyridin-3-yl)oxy)piperidin-1-yl)-1,5-dimethyl-1,2-dihydro-3H-pyrazolo[3,4-b]pyridin-3-one | 370 |
| 26 | 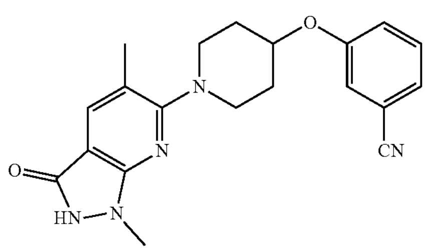 [SMILES: Cc1cc2c(=O)[nH]n(C)c2nc1N1CCC(Oc2cccc(C#N)c2)CC1] | 3-((1-(1,5-dimethyl-3-oxo-2,3-dihydro-1H-pyrazolo[3,4-b]pyridin-6-yl)piperidin-4-yl)oxy)benzonitrile | 364 |
| 27 | 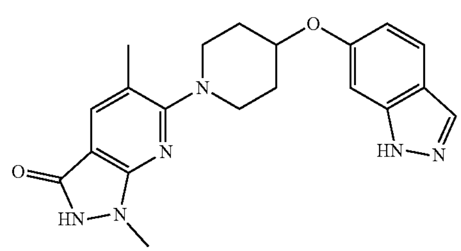 [SMILES: Cc1cc2c(=O)[nH]n(C)c2nc1N1CCC(Oc2ccc3cn[nH]c3c2)CC1] | 6-(4-((1H-indazol-6-yl)oxy)piperidin-1-yl)-1,5-dimethyl-1,2-dihydro-3H-pyrazolo[3,4-b]pyridin-3-one | 379 |
| 28* | 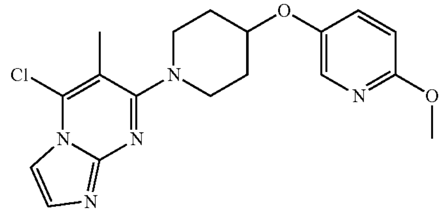 [SMILES: COc1ccc(OC2CCN(c3nc4nccn4c(Cl)c3C)CC2)cn1] | 5-chloro-7-(4-((6-methoxypyridin-3-yl)oxy)piperidin-1-yl)-6-methylimidazo[1,2-a]pyrimidine | 374 |

*Pyridine starting material is prepared as descrived in literature procedures, see e.g.: Tetsuji, O.; et al. *Bioorg. Med. Chem.* 2011, 19, 5955-5966.

Example 29A and 29B

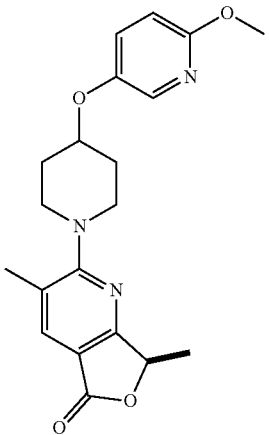

(R)-2-(4-((6-Methoxypyridin-3-yl)oxy)piperidin-1-yl)-3,7-dimethylfuro[3,4-b]pyridin-5(7H)-one and (S)-2-(4-((6-

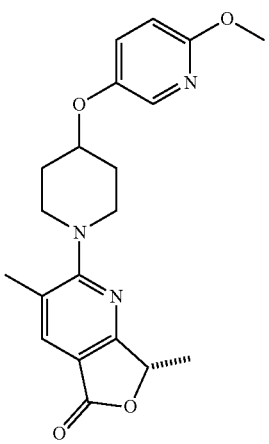

methoxypyridin-3-yl)oxy)piperidin-1-yl)-3,7-dimethylfuro[3,4-b]pyridin-5(7H)-one (Scheme 7)

Step 1: 2-(4-Hydroxypiperidin-1-yl)-3,7-dimethylfuro[3,4-b]pyridin-5(7H)-one

A mixture of piperidin-4-ol (1 g, 9.89 mmol) and 2-chloro-3,7-dimethylfuro[3,4-b]pyridin-5(7H)-one (intermediate E3, 200 mg, 1.01 mmol) was stirred at 100° C. for 2 h. The reaction was cooled to 80° C. and HCl (2M, 3 mL, 6.00 mmol) and MeOH (3 mL) was added and the mixture was stirred 30 min. After cooling to RT, an aqueous, saturated solution of sodium carbonate was added pH~10 and the mixture was extracted with EtOAc (35 mL). The organic layer was dried over anhydrous sodium sulfate, filtrated and the filtrate was concentrated. The residue was purified by silica gel chromatography (1:1 petroleum ether:THF) to afford the title compound. MS: 263 (M+1).

Step 2: (R)-2-(4-((6-Methoxypyridin-3-yl)oxy)piperidin-1-yl)-3,7-dimethylfuro[3,4-b]pyridin-5(7)-one and (S)-2-(4-((6-methoxypyridin-3-yl)oxy)piperidin-1-yl)-3,7-dimethylfuro[3,4-b]pyridin-5(7H)-one A mixture of 6-methoxypyridin-3-ol (6-methoxypyridin-3-ol (52.5 mg, 0.412 mmol), 2-(4-hydroxypiperidin-1-yl)-3,7-dimethylfuro[3,4-b]pyridin-5(7H)-one (100 mg, 0.38 mmol), PPh$_3$ (120 mg, 0.46 mmol) and DBAD (105 mg, 0.46 mmol) in toluene (10 mL) was stirred at 80° C. for 16 h. The volatiles were removed under reduced pressure and the residue was purified by reverse phase HPLC (ACN/water with 0.1% TFA modifier) and then by chiral SFC (AD column, 60%/40% MeOH with 0.1% DEA modifier/CO$_2$) to afford Example 29A (faster eluting isomer): MS: 370 (M+1). $^1$H NMR (400 MHz, methanol-$_4$): δ 7.91 (1H, d, J=2.0 Hz), 7.78 (1H, s), 7.61 (1H, dd, J=9.2, 2.8 Hz), 6.94 (1H, d, J=9.2 Hz), 5.37 (1H, q, J=6.8 Hz), 4.52-4.61 (1H, m), 3.67-3.74 (2H, m), 3.30-3.37 (2H, m), 2.37 (3H, s), 2.10-2.17 (2H, m), 1.84-1.95 (2H, m), 1.59 (3H, d, J=6.8 Hz). Example 29B (slower eluting isomer): MS: 370 (M+1). $^1$H NMR (400 MHz, methanol-$_4$): δ 7.91 (1H, d, J=2.0 Hz), 7.78 (1H, s), 7.61 (1H, dd, J=9.2, 2.8 Hz), 6.94 (1H, d, J=9.2 Hz), 5.37 (1H, q, J=6.8 Hz), 4.52-4.61 (1H, m), 3.67-3.74 (2H, m), 3.30-3.37 (2H, m), 2.37 (3H, s), 2.10-2.17 (2H, m), 1.84-1.95 (2H, m), 1.59 (3H, d, J=6.8 Hz).

The following examples in table 7 were prepared according to scheme 7 using the procedure outlined in the synthesis of Examples 29A and 29B with known or commercial phenols. In examples where there are no stereoisomers, SFC chiral separation was not carried out.

TABLE 7

| Example | Structure | Name | MS (M + 1) |
|---|---|---|---|
| 30 | 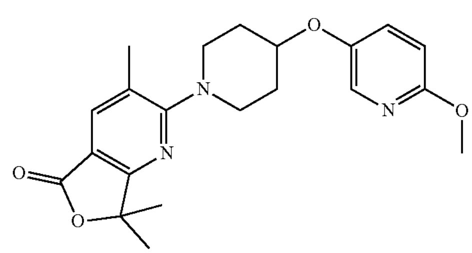 [SMILES: COc1ccc(OC2CCN(c3nc4c(cc3C)C(=O)OC4(C)C)CC2)cn1] | 2-(4-((6-methoxypyridin-3-yl)oxy)piperidin-1-yl)-3,7,7-trimethylfuro[3,4-b]pyridin-5(7H)-one | 384 |

TABLE 7-continued

| Example | Structure | Name | MS (M + 1) |
|---|---|---|---|
| 31 | 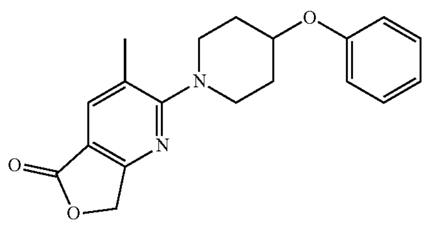 [SMILES: Cc1cc2c(nc1N1CCC(Oc3ccccc3)CC1)COC2=O] | 3-methyl-2-(4-phenoxypiperidin-1-yl)furo[3,4-b]pyridin-5(7H)-one | 325 |
| 32 | 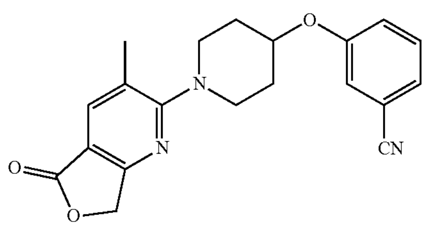 [SMILES: Cc1cc2c(nc1N1CCC(Oc3cccc(C#N)c3)CC1)COC2=O] | 3-((1-(3-methyl-5-oxo-5,7-dihydrofuro[3,4-b]pyridin-2-yl)piperidin-4-yl)oxy)benzonitrile | 350 |

Example 33

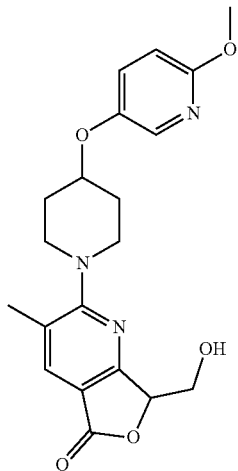

7-(Hydroxymethyl)-2-(4-((6-methoxypyridin-3-yl)oxy)piperidin-1-yl)-3-methylfuro[3,4-b]pyridin-5(7H)-one (Scheme 8)

To a solution of 2-(4-((6-methoxypyridin-3-yl)oxy)piperidin-1-yl)-3-methylfuro[3,4-b]pyridin-5(7H)-one (70 mg, 0.197 mmol) in THF (3 mL) was added LDA (2.5 M in THF, 0.095 mL, 0.236 mmol) at −78° C. under a nitrogen atmosphere. The reaction was stirred at −78° C. for 15 min before (1H-benzo[d][1,2,3]triazol-1-yl)methanol (29.4 mg, 0.197 mmol) was added. After 30 min the reaction was quenched with aqueous ammonium chloride (saturated, 5 mL) and was extracted with DCM (10 mL×3). The combined organic layers were concentrated and purified by reverse phase HPLC (ACN/water with 0.1% NH$_3$OH modifier) to afford the title compound. MS: 386 (M+1). $^1$H NMR (400 MHz, methanol-d$_4$): δ 7.84 (1H, d, J=2.8 Hz), 7.79 (1H, s), 7.43 (1H, dd, J=8.8, 2.8 Hz), 6.76 (1H, d, J=8.8 Hz), 5.34 (1H, s), 4.52-4.54 (1H, m), 4.16 (1H, dd, J=12.8, 2.8 Hz), 3.95 (1H, dd, J=4.0, 0.8 Hz), 3.85 (3H, s), 3.71-3.73 (2H, m), 3.28-3.35 (2H, m), 2.38 (3H, s), 2.11-2.16 (2H, m), 1.87-1.92 (2H, m).

Example 34

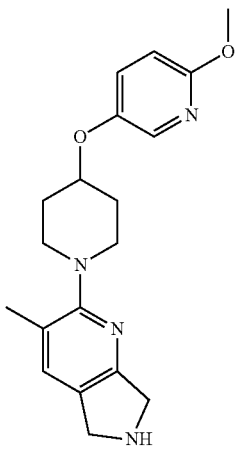

2-(4-((6-Methoxypyridin-3-yl)oxy)piperidin-1-yl)-3-methyl-6,7-dihydro-5H-pyrrolo[3,4-b]pyridine (Scheme 9)

Step 1: 2-(4-((6-Methoxypyridin-3-yl)oxy)piperidin-1-yl)-3-methyl-6,7-dihydro-5H-pyrrolo[3,4-b]pyridin-5-one To a 500 mL flask containing 2-chloro-3-methyl-6,7-dihydro-5H-pyrrolo[3,4-b]pyridin-5-one (intermediate J, 18 g, 99 mmol,), 2-methoxy-5-(piperidin-4-yloxy)pyridine dihydrochloride (intermediate F-1, 29.1 g, 104 mmol) and sodium bicarbonate (33.1 g, 394 mmol) was added N-methyl-2-pyrrolidinone (246 mL). The system was fitted with a condenser and the system was heated to 160° C. and was stirred for 15 h. The mixture was cooled to RT and filtered and the filtrate was partitioned with water (1.5 L) and 1:5 EtOAc:DCM (500 mL). The organic layer was washed with 1:1 brine:water (500 mL), dried over anhydrous sodium sulfate, filtered over a small pad of celite/silica gel/activated carbon, and concentrated. The residue was dissolved in hot iPrOH with DCM (~10%) and the mixture was sonicated and heated to 60° C. for 30 min. After slowly cooling the mixture to RT, the solids were collected and washed with 1:1:1 ether:iPrOH:heptane and was lyophilized to yield the title compound. MS: 355 (M+1).

Step 2: 2-(4-((6-Methoxypyridin-3-yl)oxy)piperidin-1-yl)-3-methyl-6,7-dihydro-5H-pyrrolo[3,4-b]pyridine BH$_3$·THF (1M in THF, 1.69 mL, 1.69 mmol) was added to a stirred, cooled 0° C. mixture of 2-(4-((6-methoxypyridin-3-yl)oxy)piperidin-1-yl)-3-methyl-6,7-dihydro-5H-pyrrolo[3,4-b]pyridin-5-one (200 mg, 0.564 mmol) in THF (10 mL). The mixture was stirred at reflux for 3 h. after which time the volatiles were removed under reduced pressure. The residue was purified by silica gel column chromatography (DCM/MeOH) to give the title compound. MS: 341 (M+1). 1H NMR (400 MHz, methanol-d$_4$): δ 7.82 (1H, d, J=2.8 Hz), 7.54 (1H, s), 7.43 (1H, dd, J=9.2, 2.8 Hz), 6.77 (1H, d, J=8.8 Hz), 4.57 (2H, s), 4.41-4.78 (3H, m), 3.85 (3H, s), 3.27-3.42 (2H, m), 2.98-3.07 (2H, m), 2.32 (3H, s), 2.05-2.32 (2H, m), 1.84-1.90 (2H, m).

The following examples in table 9 were prepared according to scheme 9 using the procedure outlined in the synthesis of Example 34 with known or prepared piperidines.

TABLE 9

| Example | Structure | Name | MS (M + 1) |
|---|---|---|---|
| 35 | 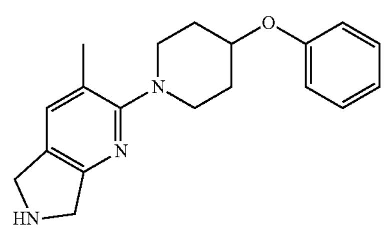 [SMILES: Cc1cc2c(nc1N1CCC(Oc3ccccc3)CC1)CNC2] | 3-methyl-2-(4-phenoxypiperidin-1-yl)-6,7-dihydro-5H-pyrrolo[3,4-b]pyridine | 385 |

Example 36

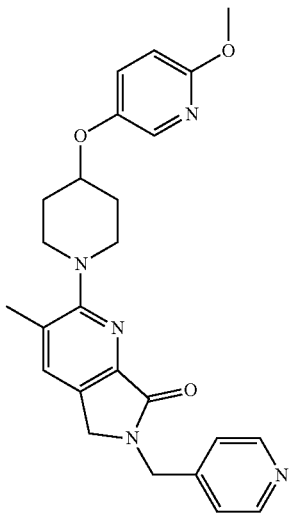 [SMILES: COc1ccc(OC2CCN(c3nc4c(cc3C)CN(Cc3ccncc3)C4=O)CC2)cn1]

2-(4-((6-Methoxypyridin-3-yl)oxy)piperidin-1-yl)-3-methyl-6-(pyridin-4-ylmethyl)-5,6-dihydro-7H-pyrrolo[3,4-b]pyridin-7-one (Scheme 10)

To a solution of 2-(4-((6-methoxypyridin-3-yl)oxy)piperidin-1-yl)-3-methyl-5H-pyrrolo[3,4-b]pyridin-7(6H)-one (30 mg, 0.085 mmol) in THF (2 mL) at 0° C. was added NaH (10 mg, 0.254 mmol, 60%) in a schlenk tube. After 1 h at 0° C., 4-(bromomethyl)pyridine hydrobromide (25.7 mg, 0.102 mmol) was added and the mixture was stirred for 16 h. The mixture was diluted with aqueous NH₄Cl (saturated, 20 mL), extracted with EtOAc (20 mL×3), the combined organic layers were washed with water (20 mL) and brine (20 mL), dried over anhydrous sodium sulfate, filtered and concentrated. The residue was purified by reverse phase HPLC (ACN/water with 0.1% NH₃OH modifier) to afford the title compound. MS: 446 (M+1). ¹H NMR (400 MHz, methanol-d₄): δ 8.73 (1H, s), 7.87 (2H, d, J=3.2 Hz), 7.81 (2H, d, J=5.6 Hz), 7.77 (1H, s), 7.47 (1H, dd, J=9.2, 3.2 Hz), 6.79 (1H, dd, J=8.8 Hz), 5.09 (2H, s), 4.84-4.86 (1H, m), 4.50 (2H, s), 3.89 (2H, s), 3.29-3.41 (2H, m), 3.12-3.19 (2H, m), 2.46 (3H, s), 2.13-2.22 (2H, m), 1.98-2.01 (2H, m).

The following examples in table 10 were prepared according to scheme 10 using the procedure outlined in the synthesis of Example 36 with known or commercial alkyl halides. Alternative reaction conditions include elevated reaction temperature (80° C.) and the use of DMF or MeCN as the solvent and DIPEA as the base.

Example 39

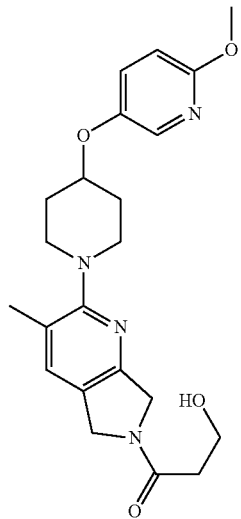

3-Hydroxy-1-(2-(4-((6-methoxypyridin-3-yl)oxy)piperidin-1-yl)-3-methyl-5,7-dihydro-6H-pyrrolo[3,4-b]pyridin-6-yl)propan-1-one (Scheme 11)

2-(4-((6-Methoxypyridin-3-yl)oxy)piperidin-1-yl)-3-methyl-6,7-dihydro-5H-pyrrolo[3,4-b]pyridine (8 mg, 0.024

TABLE 10

| Example | Structure | Name | MS (M + 1) |
|---|---|---|---|
| 37 | 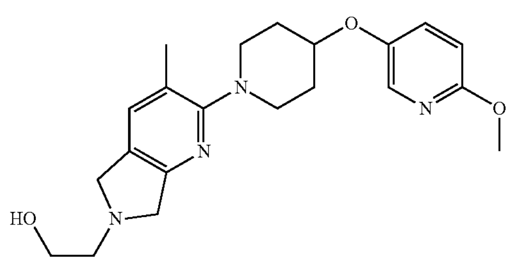 [SMILES: COc1ccc(OC2CCN(c3nc4c(cc3C)CN(CCO)C4)CC2)cn1] | 2-(2-(4-((6-methoxypyridin-3-yl)oxy)piperidin-1-yl)-3-methyl-5,7-dihydro-6H-pyrrolo[3,4-b]pyridin-6-yl)ethan-1-ol | 385 |
| 38 | | 6-(4-((6-methoxypyridin-3-yl)oxy)piperidin-1-yl)-1,5-dimethyl-1H-pyrazolo[3,4-b]pyridine | 354 | mmol) was added to a stirred mixture of 3-hydroxypropanoic acid (10.6 mg, 0.118 mmol), HATU (13.4 mg, 0.035 mmol) and DIPEA (0.041 mL, 0.235 mmol) in DMF (5 mL) and the mixture was stirred at RT for 1 h. The crude reaction mixture was directly purified by mass triggered reverse phase HPLC (ACN/water with 0.1% NH₃OH modifier) to give the title compound. MS: 413 (M+1). ¹H NMR (500 MHz, CDCl₃) δ 7.96 (1H, d, J=3.0 Hz), 7.54 (1H, s), 7.38 (1H, dd, J=8.9, 3.0 Hz), 6.79 (1H, d, J=8.9 Hz), 4.81-4.76 (4H, m), 4.45 (1H, m), 3.98 (2H, m), 3.95 (3H, s), 3.55-3.18 (4H, m), 2.63 (2H, m), 2.38 (3H, s), 2.23-2.15 (2H, m), 2.05-1.95 (2H, m).

The following examples in table 11 were prepared according to scheme 11 using the procedure outlined in the synthesis of Example 39 with known or commercial carboxylic acids.

TABLE 11

| Example | Structure | Name | MS (M + 1) |
| --- | --- | --- | --- |
| 40 | 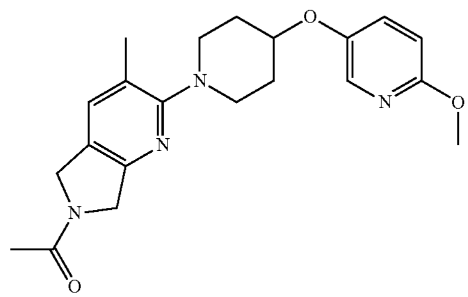 [SMILES: COc1ccc(OC2CCN(c3nc4c(cc3C)CN(C(C)=O)C4)CC2)cn1] | 1-(2-(4-((6-methoxypyridin-3-yl)oxy)piperidin-1-yl)-3-methyl-5,7-dihydro-6H-pyrrolo[3,4-b]pyridin-6-yl)ethan-1-one | 383 |
| 41 | 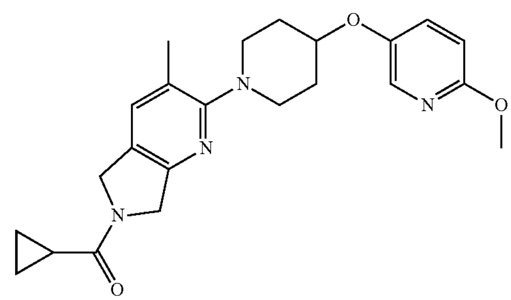 [SMILES: COc1ccc(OC2CCN(c3nc4c(cc3C)CN(C(=O)C3CC3)C4)CC2)cn1] | cyclopropyl(2-(4-((6-methoxypyridin-3-yl)oxy)piperidin-1-yl)-3-methyl-5,7-dihydro-6H-pyrrolo[3,4-b]pyridin-6-yl)methanone | 409 |
| 42 | 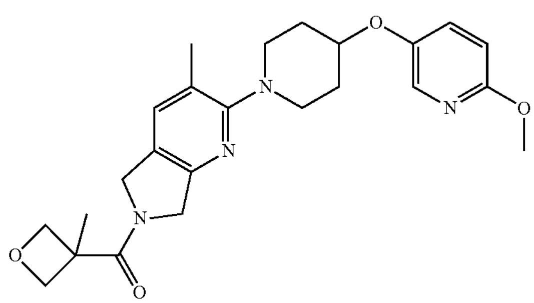 [SMILES: COc1ccc(OC2CCN(c3nc4c(cc3C)CN(C(=O)C3(C)COC3)C4)CC2)cn1] | (2-(4-((6-methoxypyridin-3-yl)oxy)piperidin-1-yl)-3-methyl-5,7-dihydro-6H-pyrrolo[3,4-b]pyridin-6-yl)(3-methyloxetan-3-yl)methanone | 439 |
| 43 | 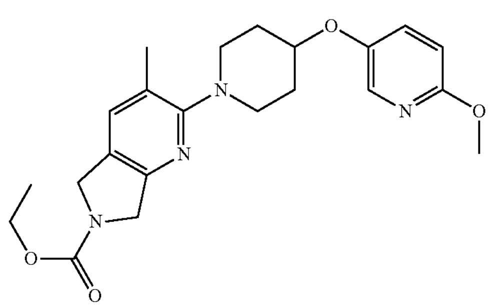 [SMILES: CCOC(=O)N1Cc2cc(C)c(N3CCC(Oc4ccc(OC)nc4)CC3)nc2C1] | ethyl 2-(4-((6-methoxypyridin-3-yl)oxy)piperidin-1-yl)-3-methyl-5,7-dihydro-6H-pyrrolo[3,4-b]pyridine-6-carboxylate | 413 |

TABLE 11-continued

| Example | Structure | Name | MS (M + 1) |
|---|---|---|---|
| 44 | 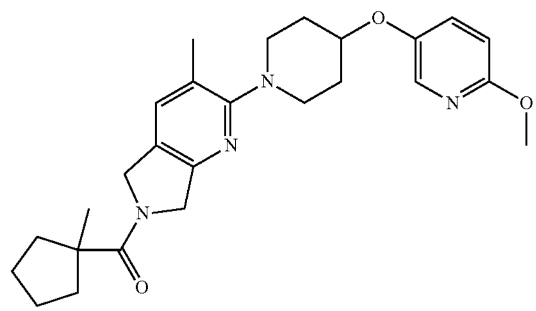 [SMILES: COc1ccc(OC2CCN(c3nc4c(cc3C)CN(C(=O)C3(C)CCCC3)C4)CC2)cn1] | (2-(4-((6-methoxypyridin-3-yl)oxy)piperidin-1-yl)-3-methyl-5,7-dihydro-6H-pyrrolo[3,4-b]pyridin-6-yl)(1-methylcyclopentyl)methanone | 451 |
| 45 | 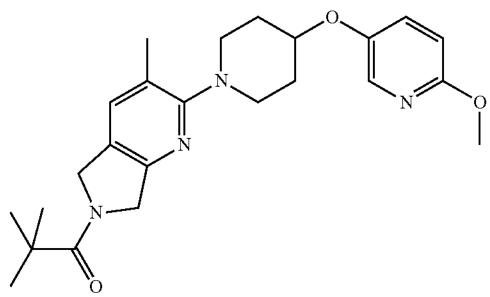 [SMILES: COc1ccc(OC2CCN(c3nc4c(cc3C)CN(C(=O)C(C)(C)C)C4)CC2)cn1] | 1-(2-(4-((6-methoxypyridin-3-yl)oxy)piperidin-1-yl)-3-methyl-5,7-dihydro-6H-pyrrolo[3,4-b]pyridin-6-yl)-2,2-dimethylpropan-1-one | 425 |
| 46 | 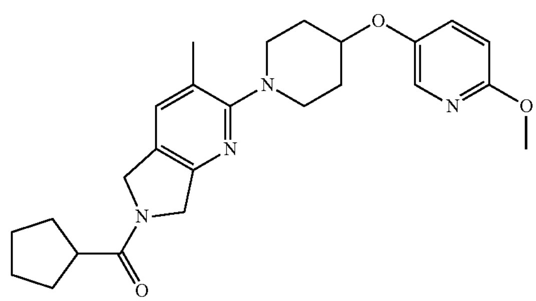 [SMILES: COc1ccc(OC2CCN(c3nc4c(cc3C)CN(C(=O)C3CCCC3)C4)CC2)cn1] | cyclopentyl(2-(4-((6-methoxypyridin-3-yl)oxy)piperidin-1-yl)-3-methyl-5,7-dihydro-6H-pyrrolo[3,4-b]pyridin-6-yl)methanone | 451 |
| 47 | 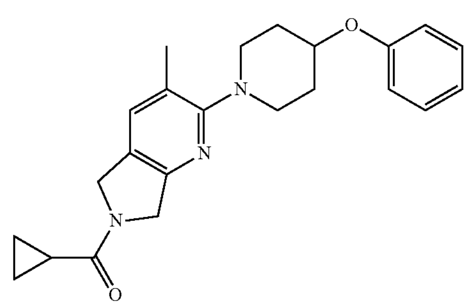 [SMILES: Cc1cc2c(nc1N1CCC(Oc3ccccc3)CC1)CN(C(=O)C1CC1)C2] | cyclopropyl(3-methyl-2-(4-phenoxypiperidin-1-yl)-5,7-dihydro-6H-pyrrolo[3,4-b]pyridin-6-yl)methanone | 378 |
| 48 | 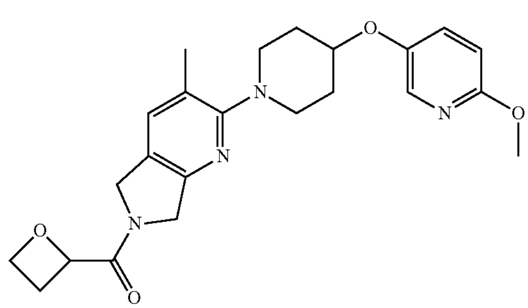 [SMILES: COc1ccc(OC2CCN(c3nc4c(cc3C)CN(C(=O)C3CCO3)C4)CC2)cn1] | (2-(4-((6-methoxypyridin-3-yl)oxy)piperidin-1-yl)-3-methyl-5,7-dihydro-6H-pyrrolo[3,4-b]pyridin-6-yl)(oxetan-2-yl)methanone | 423 |

TABLE 11-continued

| Example | Structure | Name | MS (M + 1) |
|---|---|---|---|
| 49 | 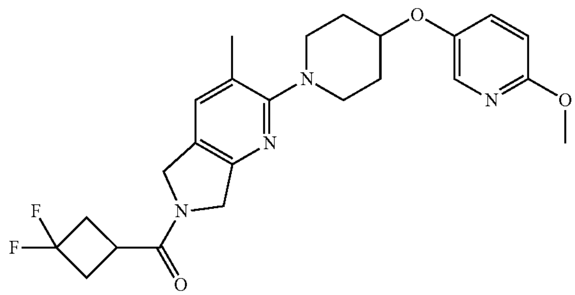 [SMILES: COc1ccc(OC2CCN(c3nc4c(cc3C)CN(C(=O)C3CC(F)(F)C3)C4)CC2)cn1] | (3,3-difluorocyclobutyl)(2-(4-((6-methoxypyridin-3-yl)oxy)piperidin-1-yl)-3-methyl-5,7-dihydro-6H-pyrrolo[3,4-b]pyridin-6-yl)methanone | 459 |
| 50 | 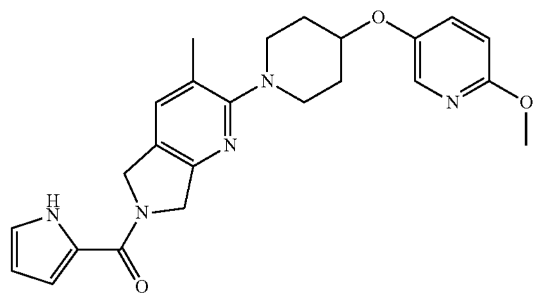 [SMILES: COc1ccc(OC2CCN(c3nc4c(cc3C)CN(C(=O)c3ccc[nH]3)C4)CC2)cn1] | (2-(4-((6-methoxypyridin-3-yl)oxy)piperidin-1-yl)-3-methyl-5,7-dihydro-6H-pyrrolo[3,4-b]pyridin-6-yl)(1H-pyrrol-2-yl)methanone | 434 |
| 51 | 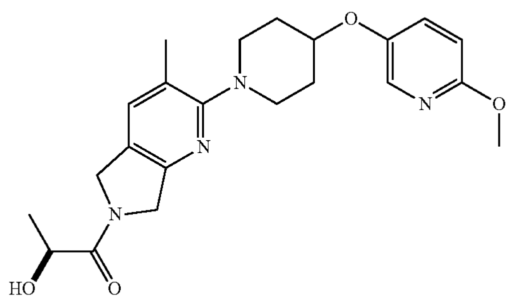 [SMILES: COc1ccc(OC2CCN(c3nc4c(cc3C)CN(C(=O)[C@H](C)O)C4)CC2)cn1] | (S)-2-hydroxy-1-(2-(4-((6-methoxypyridin-3-yl)oxy)piperidin-1-yl)-3-methyl-5,7-dihydro-6H-pyrrolo[3,4-b]pyridin-6-yl)propan-1-one | 413 |
| 52 | 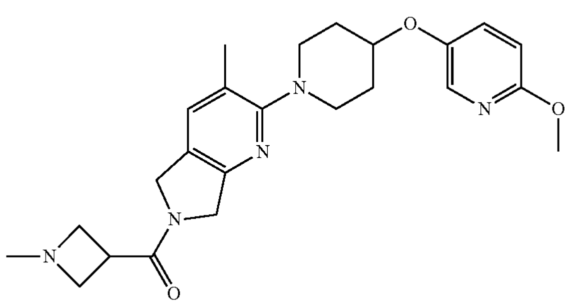 | (2-(4-((6-methoxypyridin-3-yl)oxy)piperidin-1-yl)-3-methyl-5,7-dihydro-6H-pyrrolo[3,4-b]pyridin-6-yl)(1-methylazetidin-3-yl)methanone | 438 |
| 53 | 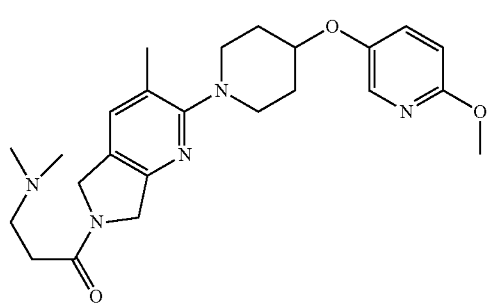 [SMILES: COc1ccc(OC2CCN(c3nc4c(cc3C)CN(C(=O)CCN(C)C)C4)CC2)cn1] | 3-(dimethylamino)-1-(2-(4-((6-methoxypyridin-3-yl)oxy)piperidin-1-yl)-3-methyl-5,7-dihydro-6H-pyrrolo[3,4-b]pyridin-6-yl)propan-1-one | 440 |

TABLE 11-continued

| Example | Structure | Name | MS (M + 1) |
| --- | --- | --- | --- |
| 54 | 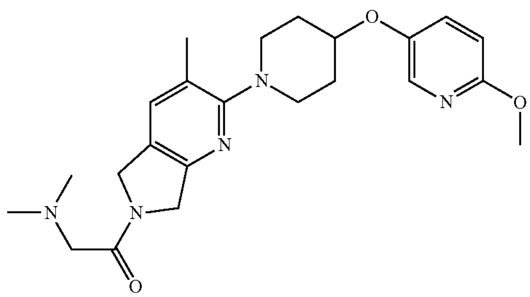 | 2-(dimethylamino)-1-(2-(4-((6-methoxypyridin-3-yl)oxy)piperidin-1-yl)-3-methyl-5,7-dihydro-6H-pyrrolo[3,4-b]pyridin-6-yl)ethan-1-one | 426 |
| 55 | 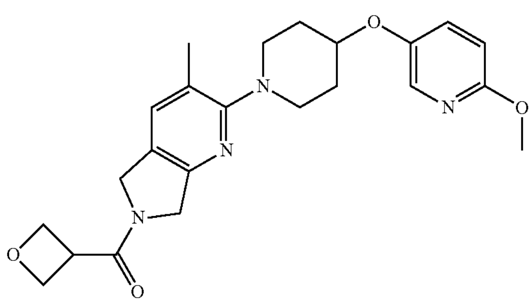 [SMILES: COc1ccc(OC2CCN(c3nc4c(cc3C)CN(C(=O)C3COC3)C4)CC2)cn1] | (2-(4-((6-methoxypyridin-3-yl)oxy)piperidin-1-yl)-3-methyl-5,7-dihydro-6H-pyrrolo[3,4-b]pyridin-6-yl)(oxetan-3-yl)methanone | 425 |
| 56 | 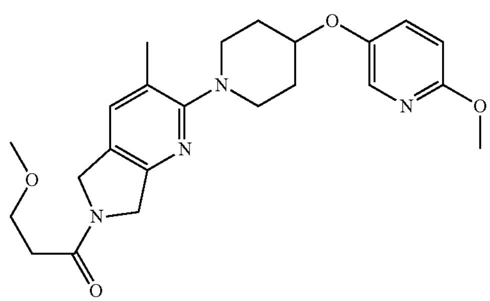 [SMILES: COCCC(=O)N1Cc2cc(C)c(N3CCC(Oc4ccc(OC)nc4)CC3)nc2C1] | 3-methoxy-1-(2-(4-((6-methoxypyridin-3-yl)oxy)piperidin-1-yl)-3-methyl-5,7-dihydro-6H-pyrrolo[3,4-b]pyridin-6-yl)propan-1-one | 427 |
| 57 | 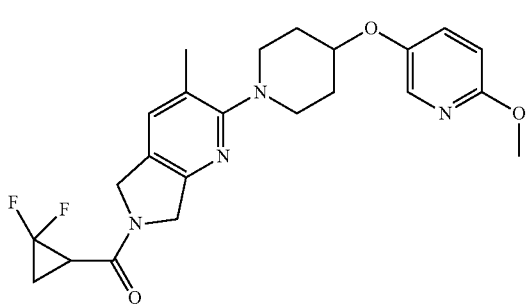 [SMILES: COc1ccc(OC2CCN(c3nc4c(cc3C)CN(C(=O)C3CC3(F)F)C4)CC2)cn1] | (2,2-difluorocyclopropyl)(2-(4-((6-methoxypyridin-3-yl)oxy)piperidin-1-yl)-3-methyl-5,7-dihydro-6H-pyrrolo[3,4-b]pyridin-6-yl)methanone | 445 |

Example 58

6-(Cyclopropylsulfonyl)-2-(4-((6-methoxypyridin-3-yl)oxy)piperidin-1-yl)-3-methyl-6,7-dihydro-5H-pyrrolo[3,4-b]pyridine (Scheme 12)

Cyclopropanesulfonyl chloride (24.78 mg, 0.176 mmol) was added to a stirred mixture of 2-(4-((6-methoxypyridin-3-yl)oxy)piperidin-1-yl)-3-methyl-6,7-dihydro-5H-pyrrolo[3,4-b]pyridine (20 mg, 0.018 mmol) and triethylamine (17.84 mg, 0.176 mmol) in DCM (5 mL) at 0° C. and the mixture was stirred at RT for 10 min. The volatiles were removed under reduced pressure and was directly purified by silica gel chromatography (40:1 DCM:MeOH) to afford the title compound. MS: 445 (M+1). $^1$H NMR (500 MHz, CDCl$_3$): δ 7.90 (1H, d, J=3.0 Hz), 7.33 (1H, s), 7.28 (1H, dd, J=8.9, 3.0 Hz), 6.73 (1H, d, J=8.9 Hz), 4.79-4.62 (4H, m), 4.36 (1H, tt, J=7.9, 3.9 Hz), 3.93 (3H, s), 3.44-3.20 (2H, m), 3.02 (2H, ddd, J=12.5, 8.9, 3.1 Hz), 2.43 (1H, tt, J=8.0, 4.8 Hz), 2.33 (3H, s), 2.14 (2H, m), 1.95 (2H, dtd, J=12.5, 8.5, 3.6 Hz), 1.31-1.28 (3H, m), 1.16-0.97 (2H, m).

The following examples in table 12 were prepared according to scheme 12 using the procedure outlined in the synthesis of Example 58 with known or commercial acylating agents, such as methyl chloroformate.

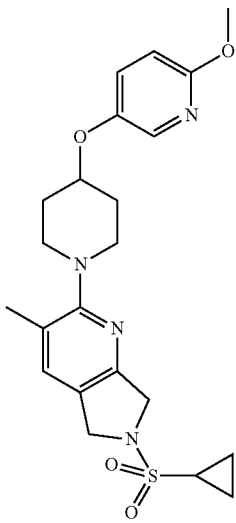 [SMILES: COc1ccc(OC2CCN(c3nc4c(cc3C)CN(S(=O)(=O)C3CC3)C4)CC2)cn1]

TABLE 12

| Example | Structure | Name | MS (M + 1) |
|---|---|---|---|
| 59 | 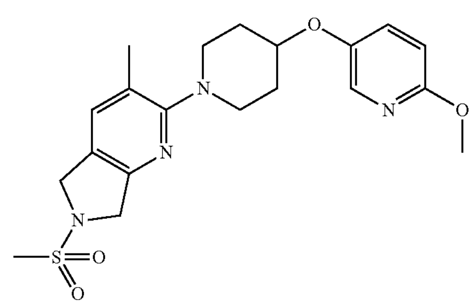 | 2-(4-((6-methoxypyridin-3-yl)oxy)piperidin-1-yl)-3-methyl-6-(methylsulfonyl)-6,7-dihydro-5H-pyrrolo[3,4-b]pyridine | 419 |
| 60 | 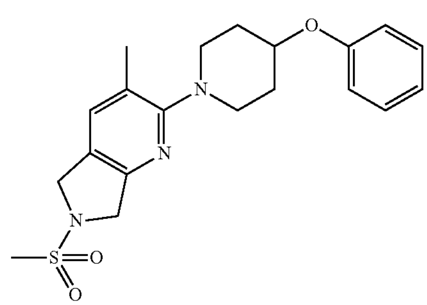 [SMILES: Cc1cc2c(nc1N1CCC(Oc3ccccc3)CC1)CN(S(C)(=O)=O)C2] | 3-methyl-6-(methylsulfonyl)-2-(4-phenoxypiperidin-1-yl)-6,7-dihydro-5H-pyrrolo[3,4-b]pyridine | 388 |
| 61 | 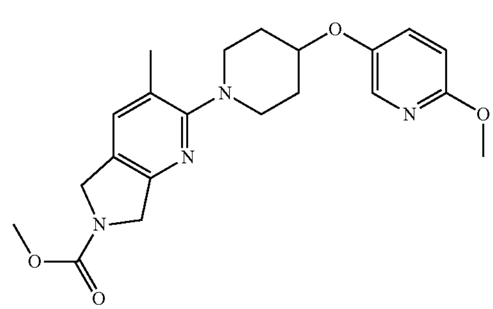 | methyl 2-(4-((6-methoxypyridin-3-yl)oxy)piperidin-1-yl)-3-methyl-5,7-dihydro-6H-pyrrolo[3,4-b]pyridine-6-carboxylate | 399 |

TABLE 12-continued

| Example | Structure | Name | MS (M + 1) |
|---------|-----------|------|------------|
| 62 | 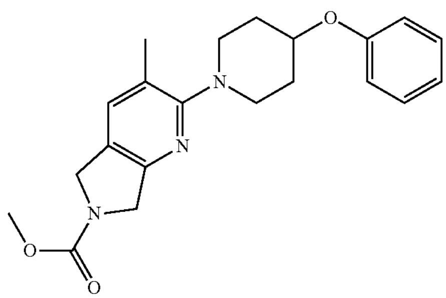 [SMILES: COC(=O)N1Cc2cc(C)c(N3CCC(Oc4ccccc4)CC3)nc2C1] | methyl 3-methyl-2-(4-phenoxypiperidin-1-yl)-5,7-dihydro-6H-pyrrolo[3,4-b]pyridine-6-carboxylate | 352 |

Example 63

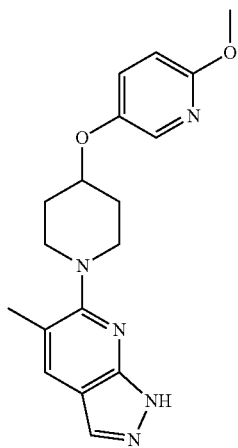

6-(4-(((6-Methoxypyridin-3-yl)oxy)piperidin-1-yl)-5-methyl-1H-pyrazolo[3,4-b]pyridine (Scheme 13)

Step 1: Methyl 2-fluoro-6-(4-(((6-methoxypyridin-3-yl)oxy)piperidin-1-yl)nicotinate To a solution of 2-methoxy-5-(piperidin-4-yloxy)pyridine hydrochloride (707 mg, 2.89 mmol) in DMF (5 mL) was added TEA (0.40 mL, 2.89 mmol) and methyl 2,6-di fluoronicotinate (500 mg, 2.89 mmol). The reaction mixture was stirred at 10° C. for 15 h before diluting with water (10 mL) and extracting with EtOAc (20 mL×3). The combined organic fractions were washed with water (30 mL×3), dried over anhydrous sodium sulfate, filtered and the filtrate was evaporated under reduced pressure. The residue was purified by silica gel chromatography (10:1-5:1 petroleum ether: EtOAc) to give the title compound.

Step 2: Methyl 5-bromo-2-fluoro-6-(4-(((6-methoxypyridin-3-yl)oxy)piperidin-1-yl)nicotinate To a solution of methyl 2-fluoro-6-(4-(((6-methoxypyridin-3-yl)oxy)piperidin-1-yl)nicotinate (700 mg, 1.94 mmol) in chloroform (10 mL) was added NBS (379 mg, 2.13 mmol). The reaction mixture was stirred at 80° C. for 2 h. The mixture was cooled before aqueous Na₂CO₃ (saturated, 20 mL) was added and the mixture was extracted with EtOAc (20 mL×3). The combined organic fractions were washed with water (30 mL×3), dried over anhydrous sodium sulfate, filtered and the filtrate was evaporated under reduced pressure. The residue was purified by silica gel chromatography (10:1-5:1 petroleum ether:EtOAc) to give the title compound.

Step 3: Methyl 2-fluoro-6-(4-(((6-methoxypyridin-3-yl)oxy) piperidin-1-yl)-5-methylnicotinate A solution of methyl 5-bromo-2-fluoro-6-(4-((6-methoxypyridin-3-yl)oxy)piperidin-1-yl)nicotinate (140 mg, 0.318 mmol), methylboronic acid (57.1 mg, 0.954 mmol), 1,1'-bis (di-tert-butylphosphino)ferrocene palladium dichloride (20 mg, 0.031 mmol) and K₃PO₄ (202 mg, 0.954 mmol) in THF (5 mL) and water (1 mL) was stirred at 75° C. for 2 h. The mixture was concentrated in vacuo and purified by chromatography on silica gel (80:20 petroleum ether:THF) to give the title compound. MS: 376 (M+1).

Step 4: (2-Fluoro-6-(4-(((6-methoxypyridin-3-yl)oxy)piperidin-1-yl)-5-methylpyridin-3-yl)methanol To a solution of methyl 2-fluoro-6-(4-(((6-methoxypyridin-3-yl)oxy)piperidin-1-yl)-5-methylnicotinate (100 mg, 0.266 mmol) in THF (15 mL) was added LiBH₄ (11.6 mg, 0.533 mmol) and stirred at 15° C. for 16 h. The reaction was diluted with water (20 mL), extracted with EtOAc (50 mL) and the organic layer was dried over anhydrous sodium sulfate, filtered and the filtrate was concentrated to afford the title compound.

Step 5: 5-Bromo-2-fluoro-6-(4-(((6-methoxypyridin-3-yl)oxy)piperidin-1-yl)nicotinaldehyde A solution of (2-fluoro-6-(4-(((6-methoxypyridin-3-yl)oxy)piperidin-1-yl)-5-methylpyridin-3-yl)methanol (50 mg, 0.144 mmol) in DCM (15 mL) and DMP (67.2 mg, 0.158 mmol) was stirred at 15° C. for 16 h. The mixture was filtered and concentrated under reduced pressure to afford the title compound.

Step 6: 6-(4-((6-Methoxypyridin-3-yl)oxy)piperidin-1-yl)-5-methyl-1H-pyrazolo[3,4-b]pyridine A mixture of 2-fluoro-6-(4-((6-methoxypyridin-3-yl)oxy)piperidin-1-yl)-5-methylnicotinaldehyde (59 mg, 0.171 mmol) and hydrazine (2 mL, 62.4 mmol) in MeOH (20 mL) was stirred at 60° C. for 16 h. The volatiles were removed and EtOH (30 mL) was added and the reaction was stirred at 100° C. for 48 h. The mixture was concentrated in vacuo and purified by reverse phase HPLC (ACN/water with 0.1% TFA modifier) to afford the title compound. MS: 340 (M+1). $^1$H NMR (400 MHz, methanol-d$_4$): δ 8.10 (1H, d, J=2.4 Hz), 7.92 (1H, d, J=3.6 Hz), 7.60 (1H, dd, J=9.2, 2.8 Hz), 6.92 (1H, d, J=9.2 Hz), 4.60-4.64 (1H, m), 3.92 (3H, s), 3.67-3.73 (2H, m), 3.25-3.43 (2H, m), 2.45 (3H, s), 2.16-2.24 (2H, m), 1.97-2.03 (2H, m).

Example 64

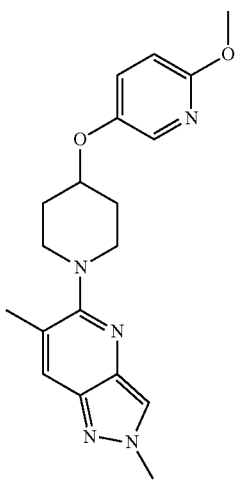

5-(4-((6-Methoxypyridin-3-yl)ox)piperidin-1-yl)-2,6-dimethyl-2H-pyrazolo[4,3-b]pyridine (Scheme 14)

To a solution of 5-chloro-2,6-dimethyl-2H-pyrazolo[4,3-b]pyridine (20 mg, 0.11 mmol), 2-methoxy-5-(piperidin-4-yloxy)pyridine (34 mg, 0.17 mmol), [(2-di-cyclohexyl phosphino-3,6-dimethoxy-2',4',6'-triisopropyl-1,1'-biphenyl)-2-(2'-amino-1,1'-biphenyl)]palladium(II) methanesulfonate methanesulfonate (Brettphos Pd G3 catalyst, 20 mg, 0.02 mmol) in THF (0.55 mL) was added t-BuONa (2 M in THF, 0.11 mL, 0.22 mmol) under an atmosphere of nitrogen. The reaction was heated at 40° C. for 16 h. The reaction was cooled and diluted with water (10 mL) and the mixture was extracted with EtOAc (20 mL×3). The combined organic fractions were washed with water (30 mL×3), dried over anhydrous sodium sulfate, filtered and the filtrate evaporated under reduced pressure. The residue was purified by reverse phase HPLC (ACN/water with 0.1% TFA modifier) yield the title compound. MS: 354 (M+1). $^1$H NMR (400 MHz, methanol-d$_4$): δ 8.27 (1H, s), 8.23 (1H, s), 7.89 (1H, d, J=2.0 Hz), 7.49 (1H, dd, J=8.8, 2.4 Hz), 6.81 (1H, d, J=9.2 Hz), 4.62-4.69 (1H, m), 4.22 (3H, s), 3.88 (3H, s), 3.77-3.81 (2H, m), 3.48-3.54 (2H, m), 2.54 (3H, s), 2.20-2.27 (2H, m), 1.95-2.15 (2H, m).

Example 65

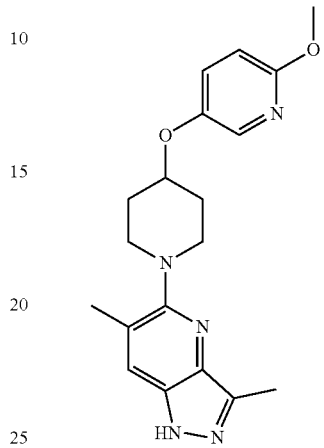

5-(4-((6-Methoxypyridin-3-yl)oxy)piperidin-1-yl)-3,6-dimethyl-1H-pyrazolo [4,3-b]pyridine (Scheme 14)

To a solution of 5-chloro-3,6-dimethyl-1-((2-(trimethylsilyl)ethoxy)methyl)-1H-pyrazolo[4,3-b]pyridine (intermediate R, 94 mg, 0.300 mmol) in THF (5 mL) was added 2-methoxy-5-(piperidin-4-yloxy)pyridine (75.0 mg, 0.360 mmol), LiHMDS (1M in THF, 0.39 mL, 0.39 mmol) and chloro(2-dicyclohexylphosphino-2',6'-diisopropoxy-1,1'-biphenyl)[2-(2'-amino-1,1'-biphenyl)]palladium(II) (22 mg, 0.03 mmol). The reaction was stirred at 70° C. for 15 h under a nitrogen atmosphere and was then cooled and quenched the reaction with water (20 mL). The mixture was extracted with EtOAc (15 mL×3) and the combined the organic layers were washed with brine, dried over anhydrous sodium sulfate, evaporated and the residue was purified by prep-TLC (5/1 ethyl acetate/petroleum ether). The residue was then dissolved in DCM (3 mL) and TFA (0.3 mL, 3.89 mmol) was added to the solution and the resulting mixture was stirred at 15° C. for 15 h. The volatiles were removed under reduced pressure and dissolved in MeOH (3 mL), and ammonium hydroxide (3 mL). The mixture was stirred at 15° C. for 2 h and then was concentrated. The resultant residue was purified by reverse phase HPLC (ACN/water with 0.1% TFA modifier) yield the title compound. MS: 354 (M+1). $^1$H NMR (400 MHz, methanol-d$_4$): δ 8.01 (1H, br s), 7.77 (1H, s), 7.46 (1H, dd, J=9.0, 2.6 Hz), 6.85 (1H, d, J=9.0 Hz), 4.55 (1H, br s), 3.98 (3H, s), 3.59-3.81 (2H, m), 3.42 (2H, d, J=8.4 Hz), 2.57 (3H, s), 2.48 (3H, s), 2.22 (2H, br s), 2.07 (2H, d, J=3.6 Hz).

The following examples in table 14 were prepared according to scheme 14 using the procedure outlined in the syntheses of Examples 64 and 65. Alternative conditions include the use of dioxanes as the solvent or using chloro (2-dicyclohexylphosphino-2',6'-di-iso-propoxy-1,1'-biphenyl)[2-(2-aminoethylphenyl)]palladium (II), methyl-tert-butyl ether adduct as the catalyst or heating to 100° C. as necessary.

TABLE 14

| Example | Structure | Name | MS (M + 1) |
|---|---|---|---|
| 66 | 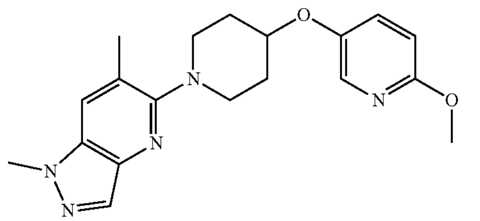 | 5-(4-((6-methoxypyridin-3-yl)oxy)piperidin-1-yl)-1,6-dimethyl-1H-pyrazolo[4,3-b]pyridine | 354 |

---

Example 67

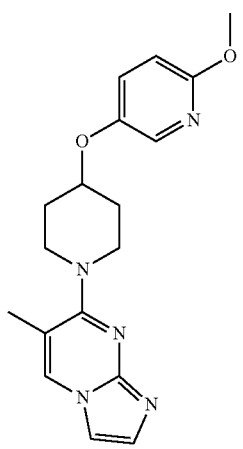

Example 68

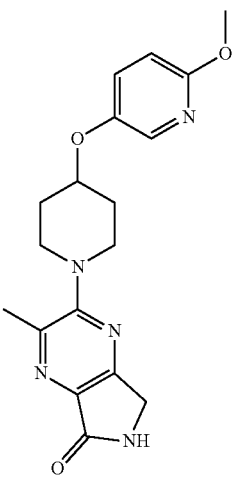

---

7-(4-((6-methoxypyridin-3-yl)oxy)piperidin-1-yl)-6-methylimidazo[1,2-a]pyrimidine (Scheme 15)

To a solution of 5-chloro-7-(4-((6-methoxypyridin-3-yl)oxy)piperidin-1-yl)-6-methylimidazo[1,2-a]pyrimidine (8 mg, 0.021 mmol) in EtOH (4 mL), THF (2 mL) and water (2 mL) was added zinc (9.79 mg, 0.150 mmol) and ammonium chloride (6.87 mg, 0.128 mmol). The reaction mixture was stirred at 15° C. for 7 h. The reaction mixture was filtered and concentrated to give a residue which was purified by reverse phase HPLC (ACN/water with 0.1% TFA modifier) yield the title compound. MS: 340 (M+1). $^1$H NMR (400 MHz, methanol-$d_4$): δ 8.46 (1H, s), 7.85 (1H, s), 7.58 (2H, d, J=17.2 Hz), 7.43 (1H, d, J=8.8 Hz), 6.77 (1H, d, J=9.2 Hz), 4.58-4.63 (1H, m), 3.98-4.06 (2H, m), 3.87 (3H, s), 3.71-3.78 (2H, m), 2.44 (3H, s), 2.11-2.17 (2H, m), 1.84-1.94 (2H, m).

2-(4-((6-Methoxypyridin-3-yl)oxy)piperidin-1-yl)-3-methyl-6,7-dihydro-5H-pyrrolo[3,4-b]pyrazin-5-one (Scheme 16)

Step 1: Methyl 3-cyano-5-(4-((6-methoxypyridin-3-yl)oxy)piperidin-1-yl)-6-methylpyrazine-2-carboxylate A solution of methyl 5-chloro-3-cyano-6-methylpyrazine-2-carboxylate (intermediate O, 40 mg, 0.189 mmol), 2-methoxy-5-(piperidin-4-yloxy)pyridine (47.2 mg, 0.227 mmol) and TEA (0.053 mL, 0.378 mmol) in DMF (4 mL) was stirred at 80° C. for 16 h. The reaction was purified by prep-TLC (2:1 petroleum ether:EtOAc) to give the title compound. MS: 384 (M+1).

Step 2: 2-(4-((6-Methoxypyridin-3-yl)oxy)piperidin-1-yl)-3-methyl-6,7-dihydro-5H-pyrrolo[3,4-b]pyrazin-5-one To a solution of methyl 3-cyano-5-(4-((6-methoxypyridin-3-yl)oxy)piperidin-1-yl)-6-methylpyrazine-2-carboxylate (40 mg, 0.104 mmol) in MeOH (2 mL) and ammonium hydroxide (0.5 mL, 0.104 mmol) was added nickel (12.3 mg, 0.209 mmol). The reaction was stirred under a hydrogen atmosphere (50 psi) at 50° C. for 3 h. The mixture was filtered and the filtrate was concentrated in vacuum. The residue was purified by reverse phase HPLC (ACN/water with 0.1% TFA modifier) to give the title compound. MS: 356 (M+1). $^1$H NMR (400 MHz, methanol-$d_4$): δ 7.91 (1H, d, J=2.8 Hz), 7.65 (1H, dd, J=9.6, 3.1 Hz), 6.97 (1H, d, J=9.2 Hz), 4.58-4.60 (1H, m), 4.34 (2H, s), 3.93 (3H, s), 3.67-3.90 (2H, m), 3.25-3.36 (2H, m), 2.59 (3H, s), 2.12-2.16 (2H, m), 1.87-1.93 (2H, m).

Example 69

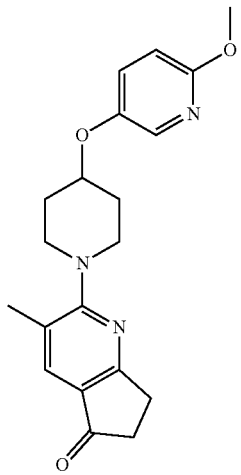

2-(4-((6-Methoxypyridin-3-yl)oxy)piperidin-1-yl)-3-methyl-6,7-dihydro-5H-cyclopenta[b]pyridin-5-one (Scheme 17)

Step 1: 3-Bromo-2-(4-((6-methoxypyridin-3-yl)oxy)piperidin-1-yl)-6,7-dihydro-5H-cyclopenta[b]pyridin-5-one A solution of 2-methoxy-5-(piperidin-4-yloxy)pyridine (99 mg, 0.475 mmol) and Hünig's base (0.13 mL, 0.730 mmol) in DMF (2 mL) was stirred at 20° C. for 1 h. 3-Bromo-2-chloro-6,7-dihydro-5H-cyclopenta[b]pyridin-5-one (intermediate P, 90 mg, 0.365 mmol) was added and the reaction was stirred at 80° C. under a nitrogen atmosphere for 2 h. The mixture was then diluted with water (5 mL) and extracted with DCM (20 mL×2). The combined organic layers were concentrated in vacuo and purified by prep-TLC (3:1 petroleum ether:EtOAc) to afford the title compound. MS: 417 (M+1).

Step 2: 2-(4-((6-Methoxypyridin-3-yl)oxy)piperidin-1-yl)-3-methyl-6,7-dihydro-5H-cyclopenta[b]pyridin-5-one To a solution of 3-bromo-2-(4-((6-methoxypyridin-3-yl)oxy)piperidin-1-yl)-6,7-dihydro-5H-cyclopenta[b]pyridin-5-one (140 mg, 0.335 mmol), $K_3PO_4$ (178 mg, 0.669 mmol) and trimethylboroxin (50.4 mg, 0.402 mmol) in dioxane (4 mL) and water (1 mL) was added 1,1'-bis(di-tert-butylphosphino)ferrocene palladium dichloride (21.8 mg, 0.033 mmol). The reaction was stirred at 80° C. for 2 h under a nitrogen atmosphere. The mixture was then diluted with water (10 mL) and extracted with DCM (20 mL×2). The combined organic layers were concentrated in vacuo and purified by prep-TLC (3:1 petroleum ether:EtOAc) to yield the title compound. MS: 354 (M+1).

$^1$H NMR (400 MHz, methanol-$d_4$): δ 7.88 (1H, d, J=2.8 Hz), 7.78 (1H, s), 7.55 (1H, dd, J=8.8, 2.8 Hz), 6.87 (1H, d, J=8.8 Hz), 4.60-4.62 (1H, m), 3.89 (3H, s), 3.75-3.78 (2H, m), 3.45-3.49 (2H, m), 3.08-3.12 (2H, m), 2.65-2.71 (2H, m), 2.37 (3H, s), 2.11-2.15 (2H, m), 1.95-1.98 (2H, m).

The following examples in table 17 were prepared according to scheme 17 using the procedure outlined in the synthesis of Example 69.

TABLE 17

| Example | Structure | Name | MS (M + 1) |
|---|---|---|---|
| 70 | 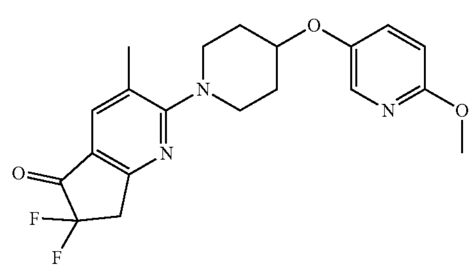 [SMILES: COc1ccc(OC2CCN(c3nc4c(cc3C)C(=O)C(F)(F)C4)CC2)cn1] | 6,6-difluoro-2-(4-((6-methoxypyridin-3-yl)oxy)piperidin-1-yl)-3-methyl-6,7-dihydro-5H-cyclopenta[b]pyridin-5-one | 390 |

Example 71A and 71B

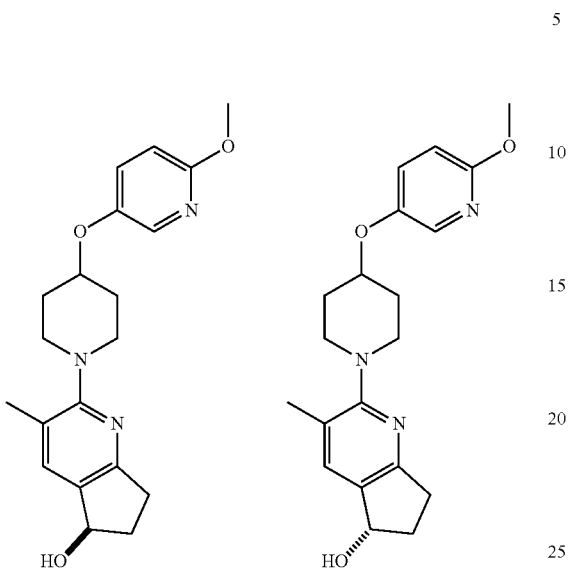

(R)-2-(4-((6-methoxypyridin-3-yl)oxy)piperidin-1-yl)-3-methyl-6,7-dihydro-5H-cyclopenta[b]pyridin-5-ol and (S)-2-(4-((6-methoxypyridin-3-yl)oxy)piperidin-1-yl)-3-methyl-6,7-dihydro-5H-cyclopenta[b]pyridin-5-ol (Scheme 18)

To a solution of 2-(4-((6-methoxypyridin-3-yl)oxy)piperidin-1-yl)-3-methyl-6,7-dihydro-5H-cyclopenta[b]pyridin-5-one (20 mg, 0.057 mmol) in MeOH (2 mL) and THF (0.5 mL) was added sodium borohydride (2.14 mg, 0.057 mmol) at 0° C. The reaction was stirred at 20° C. for 3 h. The mixture was then filtered and purified by reverse phase HPLC (ACN/water with 0.1% TFA modifier) to give the racemic product. The material was then purified by chiral SFC (AD column, 40%/60% MeOH with 0.1% diethyl amine modifier/CO$_2$) to afford Example 71A (faster eluting isomer): MS: 378 (M+1+Na). $^1$H NMR (400 MHz, methanol-d$_4$): δ 7.81 (1H, d, J=2.4 Hz), 7.50 (1H, s), 7.40 (1H, dd, J=8.8, 2.8 Hz), 6.73 (1H, d, J=9.2 Hz), 5.08-5.12 (1H, m), 4.39-4.44 (1H, m), 3.83 (1H, s), 3.31-3.33 (2H, m), 2.95-3.02 (3H, m), 2.65-2.72 (1H, m), 2.42-2.46 (1H, m), 2.25 (3H, s), 2.06-2.09 (2H, m), 1.84-1.90 (3H, m). Example 71B (slower eluting isomer): MS: 378 (M+1+Na). $^1$H NMR (400 MHz, methanol-d$_4$): δ 7.81 (1H, d, J=2.4 Hz), 7.50 (1H, s), 7.40 (1H, dd, J=8.8, 2.8 Hz), 6.74 (1H, d, J=9.2 Hz), 5.08-5.12 (1H, m), 4.40-4.44 (1H, m), 3.83 (1H, s), 3.31-3.33 (2H, m), 2.95-3.02 (3H, m), 2.64-2.72 (1H, m), 2.42-2.46 (1H, m), 2.28 (3H, s), 2.08-2.12 (2H, m), 1.84-1.90 (3H, m).

Example 72

2-(4-((6-Methoxypyridin-3-yl)oxy)piperidin-1-yl)-3-methyl-6,7-dihydro-5H-cyclopenta[b]pyridine (Scheme 18)

A solution of 2-(4-((6-methoxypyridin-3-yl)oxy)piperidin-1-yl)-3-methyl-6,7-dihydro-5H-cyclopenta[b]pyridin-5-one (20 mg, 0.057 mmol), magnesium sulfate (6.81 mg, 0.057 mmol) and ammonium acetate (7.46 µL, 0.113 mmol) in DCM (3 mL) was stirred at 40° C. for 2 h. Sodium cyanoborohydride (3.56 mg, 0.057 mmol) was added and the reaction was stirred at 40° C. for 16 h.

The mixture was filtered and purified by reverse phase HPLC (ACN/water with 0.1% TFA modifier) to furnish the title compound. MS: 340 (M+1). $^1$H NMR (400 MHz, methanol-d$_4$): δ 7.96 (1H, s), 7.86 (1H, d, J=3.2 Hz), 7.46 (1H, dd, J=9.2, 2.8 Hz), 6.78 (1H, d, J=8.8 Hz), 4.57-4.60 (1H, m), 3.86 (3H, s), 3.58-3.62 (2H, m), 3.37-3.49 (2H, m), 3.15 (2H, t, J=15.2 Hz), 2.98 (2H, t, J=15.2 Hz), 2.41 (3H, s), 2.25-2.29 (2H, m), 2.12-2.17 (2H, m), 1.94-2.02 (2H, m).

Example 73

2-(4-((6-Methoxypyridin-3-yl)oxy)piperidin-1-yl)-3,6,6-trimethyl-6,7-dihydro-5H-cyclopenta[b]pyridin-5-one (Scheme 19)

To a solution of 2-(4-((6-methoxypyridin-3-yl)oxy)piperidin-1-yl)-3-methyl-6,7-dihydro-5H-cyclopenta[b]pyridin-5-one (20 mg, 0.057 mmol) in THF (2 mL) was added sodium hydride (60%, 2.72 mg, 0.113 mmol) at 0° C. under a nitrogen atmosphere. The reaction was stirred at 0° C. for 30 min and iodomethane (9.08 g, 64.0 mmol) was added into the mixture at 0° C. After 2 h, the reaction was quenched with water (15 mL), extracted with DCM (10 mL×2), concentrated and purified by reverse phase HPLC (ACN/water with 0.1% TFA modifier) to provide the title compound. MS: 382 (M+1). $^1$H NMR (400 MHz, methanol-$d_4$): δ 7.90 (1H, d, J=2.4 Hz), 7.81 (1H, s), 7.57 (1H, dd, J=9.2, 2.8 Hz), 4.59-4.63 (1H, m), 3.91 (3H, s), 3.74-3.81 (2H, m), 3.46-3.51 (2H, m), 3.00 (2H, s), 2.40 (3H, s), 2.13-2.20 (2H, m), 1.92-1.97 (2H, m), 1.23 (6H, s).

Example 74

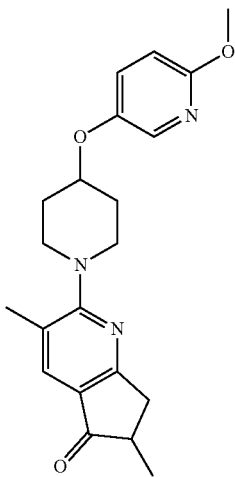

2-(4-((6-Methoxypyridin-3-yl)oxy)piperidin-1-yl)-3,6-dimethyl-6,7-dihydro-5H-cyclopenta[b]pyridin-5-one (Scheme 20)

Step 1: 2-(4-((6-Methoxypyridin-3-yl)oxy)piperidin-1-yl)-3-methyl-6-methylene-6,7-dihydro-5H-cyclopenta[b]pyridin-5-one To a solution of 2-(4-((6-methoxypyridin-3-yl)oxy)piperidin-1-yl)-3-methyl-6,7-dihydro-5H-cyclopenta[b]pyridin-5-one (100 mg, 0.283 mmol) and N-methylaniline 2,2,2-trifluoroacetate (250 mg, 1.132 mmol) in THF (3 mL) was added paraformaldehyde (84 mg, 0.283 mmol). The reaction was stirred at 70° C. for 16 h after which time the mixture was diluted with water (10 mL) and extracted with EtOAc (20 mL×2). The combined organic layers were washed with brine (20 mL×2), dried over anhydrous $Na_2SO_4$, filtered and concentrated in vacuo. The crude residue was purified by prep-TLC (2:1 petroleum ether: EtOAc) to give the title compound. MS: 366 (M+1).

Step 2: 2-(4-((6-Methoxypyridin-3-yl)oxy)piperidin-1-yl)-3,6-dimethyl-6,7-dihydro-5H-cyclopenta[b]pyridin-5-one To a solution of 2-(4-((6-methoxypyridin-3-yl)oxy)piperidin-1-yl)-3-methyl-6-methylene-6,7-dihydro-5H-cyclopenta[b]pyridin-5-one (20 mg, 0.055 mmol) in EtOAc (3 mL) was added Pd/C (10 wt %, 5.82 mg, 5.47 μmol) and the system was stirred at RT under an atmosphere of hydrogen for 20 min. The reaction was filtered and the filtrate was concentrated in vacuo and purified by reverse phase HPLC (ACN/water with 0.1% TFA modifier) to provide the title compound. MS: 368 (M+1). $^1$H NMR (400 MHz, $CDCl_3$): δ 8.03 (1H, s), 7.90 (1H, s), 7.47 (1H, dd, J=8.8, 2.4 Hz), 6.86 (1H, d, J=9.2 Hz), 4.59 (1H, s), 3.99 (3H, s), 3.76-3.87 (2H, m), 3.51-3.63 (3H, m), 2.84 (2H, d, J=16.8 Hz), 2.42 (3H, s), 1.98-2.18 (4H, m), 1.33 (3H, d, J=7.2 Hz).

Example 75

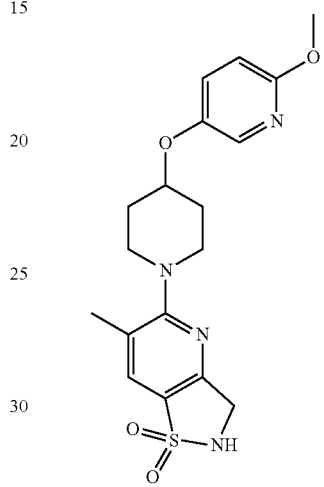

5-(4-((6-Methoxypyridin-3-yl)oxy)piperidin-1-yl)-6-methyl-2,3-dihydroisothiazolo[4,5-b]pyridine 1,1-dioxide (Scheme 21)

Step 1: 2-(tert-Butyl)-5-(4-hydroxypiperidin-1-yl)-2,3-dihydroisothiazolo[4,5-b]pyridine 1,1-dioxide A mixture of 2-(tert-butyl)-5-chloro-2,3-dihydroisothiazolo[4,5-b]pyridine 1,1-dioxide (50 mg, 0.192 mmol) and piperidin-4-ol (0.5 g, 4.94 mmol) was stirred at 120° C. for 10 min. The mixture was dissolved in EtOAc (10 mL), washed with water (20 mL), dried over anhydrous sodium sulfate, filtered and the filtrate was concentrated to give the title compound. MS: 326 (M+1).

Step 2: 6-Bromo-2-(tert-butyl)-5-(4-hydroxypiperidin-1-yl)-2,3-dihydroisothiazolo[4,5-b]pyridine 1,1-dioxide A mixture of 2-(tert-butyl)-5-(4-hydroxypiperidin-1-yl)-2,3-dihydroisothiazolo[4,5-b]pyridine 1,1-dioxide (62.4 mg, 0.192 mmol) and NBS (34.1 mg, 0.192 mmol) in MeCN (3 mL) was stirred at 15° C. for 16 h. The volatiles were removed under reduced pressure and the residue was purified by silica gel chromatography (1:1 petroleum ether: THF) to afford the title compound. MS: 404, 406 (M+1).

Step 3: 6-Bromo-2-(tert-butyl)-5-(4-((6-methoxypyridin-3-yl)oxy)piperidin-1-yl)-2,3-dihydroisothiazolo[4,5-b]pyridine 1,1-dioxide A mixture of 6-bromo-2-(tert-butyl)-5-(4-hydroxypiperidin-1-yl)-2,3-dihydroisothiazolo [4,5-b]pyridine 1,1-dioxide (64 mg, 0.158 mmol), 6-methoxypyridin-3-ol (23.77 mg, 0.190 mmol), DBAD (43.7 mg, 0.190 mmol) and $PPh_3$ (49.8 mg, 0.190 mmol) in toluene (5 mL) was stirred at 80° C. for 16 h. The mixture was concentrated and then purified by silica gel chromatography (70:30 petroleum ether:THF) to give the title compound. MS: 511, 513 (M+1).

Step 4: 2-(tert-Butyl)-5-(4-((6-methoxypyridin-3-yl)oxy)piperidin-1-yl)-6-methyl-2,3-dihydroisothiazolo[4,5-b]pyridine 1,1-dioxide A mixture of 6-bromo-2-(tert-butyl)-5-(4-((6-methoxypyridin-3-yl)oxy)piperidin-11-yl)-2,3-dihydroisothiazolo[4,5-b]pyridine 1,1-dioxide (60 mg, 0.117 mmol), 2,4,6-trimethyl-1,3,5,2,4,6-trioxatriborinane (29.5 mg, 0.235 mmol), PdCl$_2$(dppf) (17.2 mg, 0.023 mmol) and K$_3$PO$_4$ (125 mg, 0.587 mmol) in 1,4-dioxane (3 mL) and water (1 mL) was stirred at 100° C. for 16 h under a nitrogen atmosphere. The mixture was concentrated and purified by silica gel chromatography (70:30 petroleum ether:THF) to give the title compound. MS: 447 (M+1).

Step 5: 5-(4-((6-Methoxypyridin-3-yl)oxy)piperidin-1-yl)-6-methyl-2,3-dihydroisothiazolo[4,5-b]pyridine 1,1-dioxide A solution of 2-(tert-butyl)-5-(4-((6-methoxypyridin-3-yl)oxy)piperidin-1-yl)-6-methyl-2,3-dihydroisothiazolo[4,5-b]pyridine 1,1-dioxide (60 mg, 0.101 mmol) in TFA (2 mL, 26.0 mmol) was stirred at 15° C. for 16 h. The mixture was concentrated and purified by reverse phase HPLC (ACN/water with 0.1% TFA modifier) to provide the title compound. MS: 391 (M+1). $^1$H NMR (400 MHz, methanol-d$_4$): δ 7.86 (1H, d, J=2.4 Hz), 7.81 (1H, s), 7.50 (1H, dd, J=8.8, 2.4 Hz), 6.83 (1H, d, J=9.2 Hz), 4.51-4.55 (1H, m), 4.31 (2H, s), 3.88 (3H, s), 3.58-3.65 (2H, m), 3.22-3.28 (2H, m), 2.38 (3H, s), 2.08-2.15 (2H, m), 1.86-1.94 (2H, m).

The following examples in table 21 were prepared according to scheme 21 using the procedure outlined in the synthesis of Example 75 using commercially available phenols in step 3.

Example 78

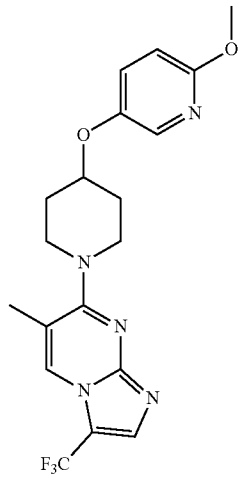

2-(4-((6-Methoxypyridin-3-yl)oxy)piperidin-1-yl)-3-methyl-6-(trifluoromethyl)imidazo[1,5-a]pyrimidine (Scheme 22)

Step 1: 2-Chloro-4-(4-((6-methoxypyridin-3-yl)oxy)piperidin-1-yl)-5-methylpyrimidine To a solution of 2,4-dichloro-5-methylpyrimidine (200 mg, 1.23 mmol) and 2-methoxy-5-(piperidin-4-yloxy)pyridine, HCl (300 mg, 1.23 mmol) in DMF (5 mL) was added DIPEA (0.86 mL, 4.90 mmol) and the reaction was heated to 50° C. for 16 h. The mixture was diluted with water (20 mL), extracted by EtOAc (10 mL×3), and the combined

TABLE 21

| Example | Structure | Name | MS (M + 1) |
|---|---|---|---|
| 76 | 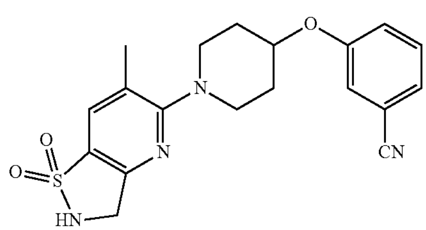 [SMILES: Cc1cc2c(nc1N1CCC(Oc3cccc(C#N)c3)CC1)CNS2(=O)=O] | 3-((1-(6-methyl-1,1-dioxido-2,3-dihydroisothiazolo[4,5-b]pyridin-5-yl)piperidin-4-yl)oxy)benzonitrile | 385 |
| 77 | | 6-methyl-5-(4-phenoxypiperidin-1-yl)-2,3-dihydroisothiazolo[4,5-b]pyridine 1,1-dioxide | 360 | organic phases were washed with water (15 mL×3), dried over anhydrous sodium sulfate, filtered and concentrated. The crude product was purified by silica gel chromatography (0-25% EtOAc/petroleum ether) to furnish the title compound. MS: 335 (M+1).

Step 2: 4-(4-(((6-Methoxypyridin-3-yl)oxy)piperidin-1-yl)-5-methylpyrimidine-2-carbonitrile To a solution of 2-chloro-4-(4-(((6-methoxypyridin-3-yl)oxy)piperidin-1-yl)-5-methylpyrimidine (170 mg, 0.508 mmol), DABCO (67 mg, 0.597 mmol) in DMSO (2.5 mL) and water (0.5 mL) was added potassium cyanide (90 mg, 1.382 mmol). After addition, the mixture was stirred at 80° C. for 16 h. The mixture was quenched by water (15 mL) and extracted with EtOAc (20 mL). The organic phase was dried over anhydrous sodium sulfate, filtered and concentrated. The crude product was purified by silica gel chromatography (0-35% EtOAc/petroleum ether) to give the title compound. MS: 326 (M+1).

Step 3: tert-Butyl ((4-(4-(((6-methoxypyridin-3-yl)oxy)piperidin-1-yl)-5-methylpyrimidin-2-yl)methyl)carbamate To a solution of 4-(4-(((6-methoxypyridin-3-yl)oxy)piperidin-1-yl)-5-methylpyrimidine-2-carbonitrile (110 mg, 0.338 mmol) and Boc₂O (0.096 mL, 0.412 mmol) in EtOAc (10 mL) was added Pd/C (10 wt %, 50 mg, 0.047 mmol). The mixture was stirred for 16 h under a hydrogen atmosphere and was then filtered and concentrated. The crude product was purified by silica gel chromatography (0-35% EtOAc/petroleum ether) to give the title compound. MS: 430 (M+1).

Step 4: (4-(4-(((6-methoxypyridin-3-yl)oxy)piperidin-1-yl)-5-methylpyrimidin-2-yl)methanamine 2TFA To a solution of tert-butyl ((4-(4-(((6-methoxypyridin-3-yl)oxy)piperidin-1-yl)-5-methylpyrimidin-2-yl)methyl)carbamate (65 mg, 0.151 mmol) in DCM (2 mL) was added TFA (0.2 mL, 2.60 mmol). The reaction was stirred at 18° C. for 16 h before the volatiles were removed under reduced pressure to afford the title compound. MS: 330 (M+1).

Step 5: 2-(4-(((6-Methoxypyridin-3-yl)oxy)piperidin-1-yl)-3-methyl-6-(trifluoromethyl)imidazo[1,5-a]pyrimidine To a solution of (4-(4-(((6-methoxypyridin-3-yl)oxy)piperidin-1-yl)-5-methylpyrimidin-2-yl)methanamine, bisTFA salt (80 mg, 0.144 mmol) and TEA (0.080 mL, 0.574 mmol) in THF (1 mL) was added triphosgene (19.2 mg, 0.065 mmol) portionwise at 0° C. The mixture was stirred at 0° C. for 3 min and additional triphosgene (34.1 mg, 0.115 mmol) was added and the reaction was stirred at 0° C. for another 5 min. The mixture was quenched by aqueous NaHCO₃ (saturated, 10 mL), extracted by EtOAc (15 mL), the organic was dried over anhydrous sodium sulfate, filtered and concentrated. The crude product was purified by reverse phase HPLC (ACN/water with 0.1% ammonium hydroxide modifier) to give the title compound. MS: 408 (M+1). ¹H NMR (400 MHz, CDCl₃): δ 8.02 (1H, s), 7.88 (1H, d, J=2.8 Hz), 7.25-7.29 (2H, m), 6.72 (1H, d, J=9.2 Hz), 4.40-4.43 (1H, m), 3.91 (3H, s), 3.56-3.66 (2H, m), 3.19-3.27 (2H, m), 2.32 (3H, s), 2.07-2.15 (2H, m), 1.90-2.02 (2H, m).

Example 79

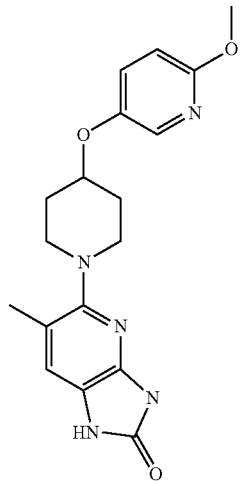

5-(4-(((6-Methoxypyridin-3-yl)oxy)piperidin-1-yl)-6-methyl-1,3-dihydro-2H-imidazo[4,5-b]pyridin-2-one (Scheme 23)

Step 1: 6-(4-(((6-Methoxypyridin-3-yl)oxy)piperidin-1-yl)-3-nitropyridin-2-amine To a solution of 6-chloro-3-nitropyridin-2-amine (100 mg, 0.576 mmol) and 2-methoxy-5-(piperidin-4-yloxy)pyridine, 2HCl (194 mg, 0.691 mmol) in DMF (3 mL) was added DIPEA (223 mg, 1.73 mmol). The reaction was stirred at 80° C. for 2 h before cooling to RT and diluting with water (10 mL). The mixture was extracted with EtOAc (10 mL×3) and the combined organic fractions were washed with water (20 mL×3), dried over anhydrous sodium sulfate, filtered and concentrated. The residue was purified by silica gel chromatography (0-50% EtOAc: petroleum ether) to afford the title compound. MS: 346 (M+1).

Step 2: 5-Bromo-6-(4-(((6-methoxypyridin-3-yl)oxy)piperidin-1-yl)-3-nitropyridin-2-amine To a solution of 6-(4-(((6-methoxypyridin-3-yl)oxy)piperidin-1-yl)-3-nitropyridin-2-amine (175 mg, 0.507 mmol) in chloroform (5 mL) was added NBS (108 mg, 0.608 mmol). The reaction was stirred at 80° C. for 20 min and then the volatiles were removed under reduced pressure. The residue was purified by prep-TLC (1/1 EtOAc/petroleum ether) to furnish the title compound. MS: 424, 426 (M+1).

Step 3: 6-(4-(((6-Methoxypyridin-3-yl)oxy)piperidin-1-yl)-5-methyl-3-nitropyridin-2-amine To a solution of 2,4,6-trimethyl-1,3,5,2,4,6-trioxatriborinane (59.2 mg, 0.471 mmol), 5-bromo-6-(4-(((6-methoxypyridin-3-yl)oxy)piperidin-1-yl)-3-nitropyridin-2-amine (200 mg, 0.471 mmol) and K₃PO₄ (300 mg, 1.41 mmol) in THF (4 mL) and water (4 mL) was added 1,1'-bis(di-tert-butylphosphino)ferrocene palladium dichloride (30.7 mg, 0.047 mmol). The reaction was stirred at 80° C. for 2 h under a nitrogen atmosphere. The mixture was cooled to RT and diluted with water (10 mL), extracted with EtOAc (10 mL×3) and the combined organic phases were washed with water (20 mL×3), dried over anhydrous sodium sulfate, filtered and concentrated. The residue was purified by silica gel chromatography (0-40% EtOAc: petroleum ether) to yield the title compound. MS: 360 (M+1).

Step 4: 6-(4-(((6-Methoxypyridin-3-yl)oxy)piperidin-1-yl)-5-methylpyridine-2,3-diamine To a solution of 6-(4-((6-methoxypyridin-3-yl)oxy)piperidin-1-yl)-5-methyl-3-nitropyridin-2-amine (140 mg, 0.390 mmol) in MeOH (20 mL) was added Pd/C (10 wt %, 41.5 mg, 0.039 mmol). The reaction was stirred at 15° C. for 2 h under a hydrogen atmosphere. The mixture was filtered and the filtrate was concentrated under reduced pressure to give the title compound. MS: 330 (M+1).

Step 5: 5-(4-((6-Methoxypyridin-3-yl)oxy)piperidin-1-yl)-6-methyl-1H-imidazo[4,5-b]pyridin-2(3H)-one To a solution of 6-(4-((6-methoxypyridin-3-yl)oxy)piperidin-1-yl)-5-methylpyridine-2,3-diamine (130 mg, 0.395 mmol) and TEA (0.165 mL, 1.18 mmol) in THF (10 mL) was added triphosgene (35.1 mg, 0.118 mmol). The reaction was stirred at 15° C. for 2 h before the volatiles were evaporated under reduced pressure. The residue was purified by reverse phase HPLC (ACN/water with 0.1% TFA modifier) to give the title compound. MS: 356 (M+1). $^1$H NMR (400 MHz, methanol-d$_4$): δ 7.89 (1H, s), 7.49 (1H, d, J=8.8 Hz), 7.27 (1H, s), 6.82 (1H, d, J=8.8 Hz), 4.58-4.62 (1H, m), 3.88 (3H, s), 3.68-3.72 (2H, m), 3.42-3.48 (2H, m), 2.44 (3H, s), 2.26-2.32 (2H, m), 2.10-2.15 (2H, m).

Example 80

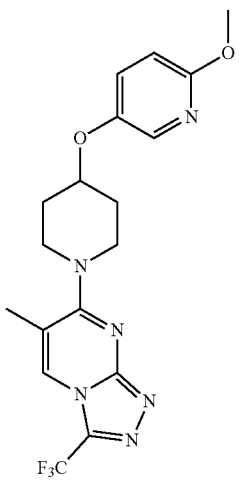

7-(4-((6-Methoxypyridin-3-yl)oxy)piperidin-1-yl)-6-methyl-3-(trifluoromethyl)-[1,2,4]triazolo[4,3-a]pyrimidine (Scheme 24)

Step 1: 2-Chloro-4-(4-((6-methoxypyridin-3-yl)oxy)piperidin-1-yl)-5-methylpyrimidine 2,4-Dichloro-5-methylpyrimidine (200 mg, 1.23 mmol) and 2-methoxy-5-(piperidin-4-yloxy)pyridine (300 mg, 1.07 mmol) were dissolved in DMF (5 mL). DIPEA (0.856 mL, 5.19 mmol) was added at 0° C. and the resulting mixture was heated to 50° C. and stirred for 12 h. The reaction mixture was poured into water (10 mL), extracted with EtOAc (10 mL×3), dried over anhydrous sodium sulfate, filtered and evaporated. The residue was purified by silica gel column (20% EtOAc/petroleum ether) to yield the title compound. $^1$H NMR (400 MHz, CDCl$_3$) δ 7.96 (1H, s), 7.86 (1H, d, J=2.8 Hz), 7.25 (1H, dd, J=8.8, 2.8 Hz), 6.71 (1H, d, J=8.8 Hz), 4.43 (1H, dt, J=6.8, 3.2 Hz), 3.90 (3H, s), 3.75-3.83 (2H, m), 3.49-3.42 (2H, m), 2.21 (3H, s), 2.01-2.10 (2H, m), 1.84-1.96 (2H, m).

Step 2: 2-Hydrazinyl-4-(4-((6-methoxypyridin-3-yl)oxy)piperidin-1-yl)-5-methylpyrimidine 2-Chloro-4-(4-((6-methoxypyridin-3-yl)oxy)piperidin-1-yl)-5-methylpyrimidine (50 mg, 0.149 mmol) was dissolved in EtOH (5 mL), then hydrazine hydrate (1.0 mL, 20 mmol) and magnesium sulfate (1.00 g, 8.33 mmol) were added. The resulting mixture was heated to 90° C. and stirred for 12 h. Water (20 mL) was added to quench the reaction and the aqueous phase was extracted with DCM (20 mL×3). The combined organic layers were dried over anhydrous sodium sulfate, filtered and concentrated to afford the title compound, which was used directly for the next step without purification. MS: 331 (M+1).

Step 3: 7-(4-((6-Methoxypyridin-3-yl)oxy)piperidin-1-yl)-6-methyl-3-(trifluoromethyl)-[1,2,4]triazolo[4,3-a]pyrimidine 2-Hydrazinyl-4-(4-((6-methoxypyridin-3-yl)oxy)piperidin-1-yl)-5-methylpyrimidine (33 mg, 0.10 mmol) and TFAA (2 mL) were heated to 80° C. for 2 h. The reaction was cooled to RT and was quenched with saturated aqueous NaHCO$_3$ slowly (~pH 8), extracted with DCM (5 mL×3), and the combined organics were dried over anhydrous sodium sulfate, filtered and concentrated. The crude product was purified by reverse phase HPLC (ACN/water with 0.1% TFA modifier) to give the title compound. MS: 409 (M+1). $^1$H NMR (400 MHz, CDCl$_3$): δ 7.98 (2H, s), 7.41 (1H, dd, J=8.8, 2.8 Hz), 6.83 (1H, d, J=9.2 Hz), 4.56 (1H, br s), 3.97 (3H, s), 3.83-3.94 (2H, m), 3.67-3.81 (2H, m), 2.43 (3H, s), 2.07-2.20 (2H, m), 1.96-2.04 (2H, m).

Example 81A and 81B

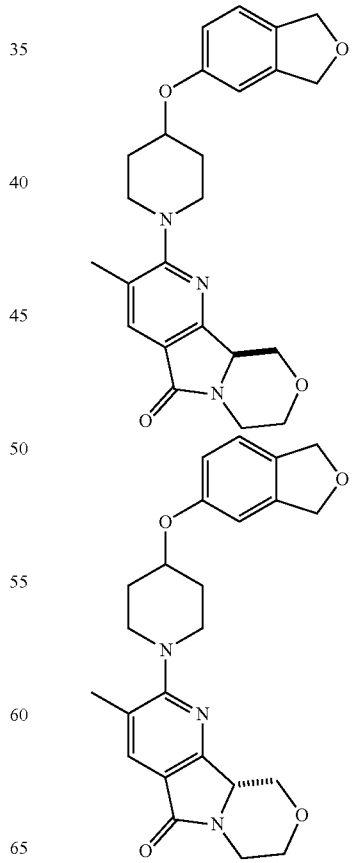

(S)-2-(4-((1,3-Dihydroisobenzofuran-5-yl)oxy)piperidin-1-yl)-3-methyl-7,8,10,10a-tetrahydro-5H-pyrido[2',3':3,4]pyrrolo[2,1-c][1,4]oxazin-5-one and (R)-2-(4-((1,3-dihydroisobenzofuran-5-yl)oxy)piperidin-1-yl)-3-methyl-7,8,10,10a-tetrahydro-5H-pyrido[2',3':3,4]pyrrolo [2,1-c][1,4] oxazin-5-one (Scheme 25)

Step 1: Methyl 2-cyano-6-(4-((1,3-dihydroisobenzofuran-5-yl)oxy)piperidin-1-yl)-5-methylnicotinate To a solution of 4-((1,3-dihydroisobenzofuran-5-yl)oxy)piperidine, HCl (1.6 g, 6.26 mmol) and methyl 6-chloro-2-cyano-5-methylnicotinate (1.38 g, 6.57 mmol) in DMF (20 mL) was added DIPEA (3.28 mL, 18.8 mmol). The reaction mixture was stirred at 80° C. for 15 h before being cooled to RT. Water (10 mL) was added and the mixture was extracted with ethyl acetate (10 mL×3). The combined organic fractions were washed with water (20 mL×3), dried over anhydrous sodium sulfate, filtered and concentrated under reduced pressure. The residue was purified by silica gel chromatography (0-40% THF/petroleum ether) to give the title compound. MS: 394 (M+1).Step 2: 2-(4-((1,3-Dihydroisobenzofuran-5-yl)oxy)piperidin-1-yl)-3-methyl-6,7-dihydro-5H-pyrrolo[3,4-b]pyridin-5-one To a solution of methyl 2-cyano-6-(4-((1,3-dihydroisobenzofuran-5-yl)oxy)piperidin-1-yl)-5-methylnicotinate (1.86 g, 4.73 mmol) in THF (20 mL) was added nickel (0.028 g, 0.473 mmol). The reaction mixture was stirred at 30° C. for 15 h under a hydrogen atmosphere (50 psi). The reaction mixture was filtered and the solvent was evaporated under reduced pressure to give the title compound. MS: 366 (M+1).

Step 3: Methyl 2-(2-(4-((1,3-dihydroisobenzofuran-5-yl)oxy)piperidin-1-yl)-3-methyl-5-oxo-5H-pyrrolo[3,4-b]pyridin-6(7H)-yl)acetate To a solution of 2-(4-((1,3-dihydroisobenzofuran-5-yl)oxy)piperidin-1-yl)-3-methyl-6,7-dihydro-5H-pyrrolo[3,4-b]pyridin-5-one (1.64 g, 4.49 mmol) in DMF (10 mL) was added NaH (0.359 g, 8.98 mmol) and methyl 2-bromoacetate (1.37 g, 8.98 mmol). The reaction mixture was stirred at 20° C. for 1 h. Water (10 mL) was added and the mixture was extracted with ethyl acetate (10 mL×3). The combined organic fractions were washed with water (20 mL×3), dried over anhydrous sodium sulfate, and concentrated was used without further purification. MS: 438 (M+1).

Step 4: 2-(4-((1,3-Dihydroisobenzofuran-5-yl)oxy)piperidin-1-yl)-6-(2-hydroxyethyl)-3-methyl-6,7-dihydro-5H-pyrrolo[3,4-b]pyridin-5-one To a solution of methyl 2-(2-(4-((1,3-dihydroisobenzofuran-5-yl)oxy)piperidin-1-yl)-3-methyl-5-oxo-5H-pyrrolo[3,4-b]pyridin-6(7H)-yl)acetate (1.96 g, 4.48 mmol) in THF (20 mL) was added LiBH$_4$ (0.293 g, 13.44 mmol). The reaction mixture was stirred at 20° C. for 1 h. Water (10 mL) was added and the mixture was extracted with DCM (10 mL×3). The combined organic fractions were washed with water (20 mL×3), dried over anhydrous sodium sulfate, filtered and concentrated to afford the title compound. MS: 410 (M+1).

Step 5: 6-(2-((tert-Butyldiphenylsilyl)oxy)ethyl)-2-(4-((1,3-dihydroisobenzofuran-5-yl)oxy)piperidin-1-yl)-3-methyl-6,7-dihydro-5H-pyrrolo[3,4-b]pyridin-5-one To a solution of 2-(4-((1,3-dihydroisobenzofuran-5-yl)oxy)piperidin-1-yl)-6-(2-hydroxyethyl)-3-methyl-6,7-dihydro-5H-pyrrolo[3,4-b]pyridin-5-one (1.9 g, 4.64 mmol) and TBDPSCl (2.38 mL, 9.28 mmol) in DCM (10 mL) was added 1H-imidazole (0.632 g, 9.28 mmol). The reaction mixture was stirred at 50° C. for 1 h. Water (10 mL) was added and the mixture was extracted with DCM (10 mL×3). The combined organic fractions were washed with water (20 mL×3), dried over anhydrous sodium sulfate, filtered and the solvent was evaporated under reduced pressure. The residue was purified by silica gel chromatography (0-40% EtOAc/petroleum ether) to give the title compound. MS: 648 (M+1).

Step 6: 6-(2-((tert-Butyldiphenylsilyl)oxy)ethyl)-2-(4-((1,3-dihydroisobenzofuran-5-yl)oxy)piperidin-1-yl)-7-(hydroxymethyl)-3-methyl-6,7-dihydro-5H-pyrrolo[3,4-b]pyridin-5-one To a solution of 6-(2-((tert-butyldiphenylsilyl)oxy)ethyl)-2-(4-((1,3-dihydroisobenzofuran-5-yl)oxy)piperidin-1-yl)-3-methyl-6,7-dihydro-5H-pyrrolo[3,4-b]pyridin-5-one (1.5 g, 2.32 mmol) in THF (30 mL) was added LiHMDS (1 M, 13.9 mL, 13.89 mmol) and (1H-benzo[d][1,2,3]triazol-1-yl)methanol (0.518 g, 3.47 mmol). The reaction mixture was stirred at −70° C. for 1 h before warming to RT. Water (30 mL) was added and the mixture was extracted with ethyl acetate (30 mL×3). The combined organic fractions were washed with water (60 mL×3), dried over anhydrous sodium sulfate, filtered and concentrated. The residue was purified by combiflash (0-40% THF/petroleum ether) to give the title compound.

Step 7: 2-(4-((1,3-Dihydroisobenzofuran-5-yl)oxy)piperidin-1-yl)-6-(2-hydroxyethyl)-7-(hydroxymethyl)-3-methyl-6,7-dihydro-5H-pyrrolo[3,4-b]pyridin-5-one To a solution of 6-(2-((tert-butyldiphenylsilyl)oxy)ethyl)-2-(4-((1,3-dihydroisobenzofuran-5-yl)oxy)piperidin-1-yl)-7-(hydroxymethyl)-3-methyl-6,7-dihydro-5H-pyrrolo[3,4-b]pyridin-5-one (500 mg, 0.738 mmol) in THF (10 mL) was added TBAF (2.21 mL, 2.21 mmol). The reaction mixture was stirred at 20° C. for 5 h before being diluted with water (10 mL) and the mixture was extracted with ethyl acetate (10 mL×3). The combined organic fractions were washed with water (20 mL×3), dried over anhydrous sodium sulfate, filtered and concentrated under reduced pressure. The residue was purified by silica gel chromatography (0-80% THF/petroleum ether) to give the title compound. MS: 440 (M+1).

Step 8: (S)-2-(4-((1,3-Dihydroisobenzofuran-5-yl)oxy)piperidin-1-yl)-3-methyl-7,8,10,10a-tetrahydro-5H-pyrido[2',3':3,4]pyrrolo[2,1-c][1,4]oxazin-5-one and (R)-2-(4-((1,3-dihydroisobenzofuran-5-yl)oxy)piperidin-1-yl)-3-methyl-7,8,10,10a-tetrahydro-5H-pyrido[2',3':3,4]pyrrolo[2,1-c][1,4]oxazin-5-one To a solution of 2-(4-((1,3-dihydroisobenzofuran-5-yl)oxy)piperidin-1-yl)-6-(2-hydroxyethyl)-7-(hydroxymethyl)-3-methyl-6,7-dihydro-5H-pyrrolo[3,4-b]pyridin-5-one (280 mg, 0.637 mmol) in THF (6 mL) was added NaH (61.2 mg, 1.53 mmol) and TsCl (182 mg, 0.956 mmol).

The reaction mixture was stirred at −70° C. to 10° C. for 15 h before water (10 mL) was added and the mixture was extracted with ethyl acetate (10 mL×3). The combined organic fractions were washed with water (20 mL×3), dried over anhydrous sodium sulfate, filtered and concentrated. The residue was purified by reverse phase HPLC (ACN/water with 0.1% TFA modifier) to give the racemate. Chiral SFC resolution (OJ column, 40%/60% EtOH with 0.1% diethylamine modifier/CO$_2$) afforded the title compounds. Example 81A (faster eluting isomer): MS: 422 (M+1). $^1$H NMR (400 MHz, methanol-d$_4$): δ (1H, s), 7.17 (1H, d, J=8.4 Hz), 6.89-6.92 (2H, m), 5.03 (2H, s), 5.01 (2H, s), 4.90-4.95 (2H, m), 4.58-4.62 (2H, m), 4.51-4.53 (2H, m), 4.23 (1H, d, J=10.8 Hz), 3.99-4.01 (1H, m), 3.56-3.58 (2H, m), 3.19-3.24 (2H, m), 3.05 (2H, t, J=12.0 Hz), 2.38 (3H, s), 2.10-2.12 (2H, m), 1.90-1.93 (2H, m). Example 81B (slower eluting isomer): MS: 422 (M+1). $^1$H NMR (400 MHz, methanol-d$_4$): δ 7.81 (1H, s), 7.17 (1H, d, J=8.0 Hz), 6.89-6.92 (2H, m), 5.03 (2H, s), 5.01 (2H, s), 4.90-4.95 (2H, m), 4.58-4.62 (2H, m), 4.51-4.53 (2H, m), 4.23 (1H, d, J=10.8 Hz), 3.99-4.01 (1H, m), 3.56-3.58 (2H, m), 3.19-3.24 (2H, m), 3.05 (2H, t, J=12.0 Hz), 2.38 (3H, s), 2.10-2.12 (2H, m), 1.90-1.93 (2H, m).

The following examples in table 25 were prepared according to scheme 25 using the procedure outlined in the synthesis of Examples 81A and 81B with the omission of chiral resolution in step 8.

zofuran-5-yl)oxy)piperidin-1-yl)-3-methyl-8,9,10,10a-tetrahydropyrido[2',3': 3,4]pyrrolo[1,2-a]pyrazin-5(7H)-one (Scheme 26)

Step 1: Methyl 6-(4-((1,3-dihydroisobenzofuran-5-yl)oxy)piperidin-1-yl)-2-iodo-5-methylnicotinate To a solution of 4-((1,3-dihydroisobenzofuran-5-yl)oxy)piperidine, HCl (300 mg, 1.17 mmol) and methyl 6-chloro-2-iodo-5-methylnicotinate (402 mg, 1.29 mmol) in DMF (5 mL) was added DIPEA (0.205 mL, 1.17 mmol). The reaction

TABLE 25

| Example | Structure | Name | MS (M + 1) |
|---------|-----------|------|------------|
| 82 | 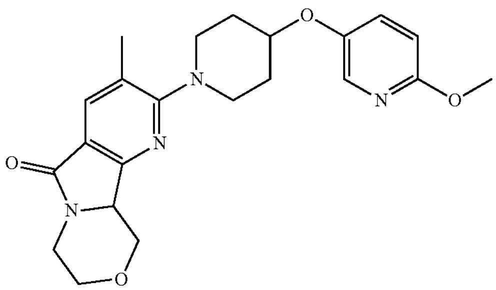 [SMILES: COc1ccc(OC2CCN(c3nc4c(cc3C)C(=O)N3CCOCC43)CC2)cn1] | 2-(4-((6-methoxypyridin-3-yl)oxy)piperidin-1-yl)-3-methyl-7,8,10,10a-tetrahydro-5H-pyrido[2',3':3,4]pyrrolo[2,1-c][1,4]oxazin-5-one | 411 |

Example 83A and 83B

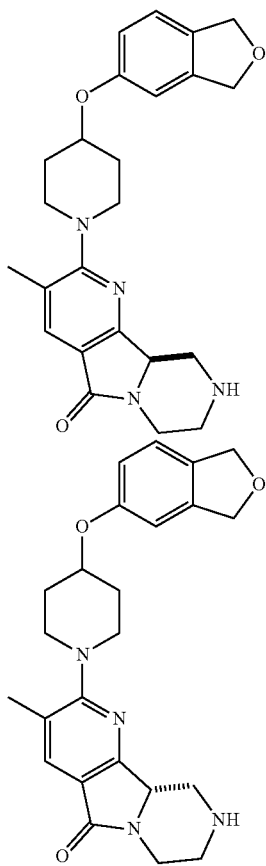

(R)-2-(4-((1,3-dihydroisobenzofuran-5-yl)oxy)piperidin-1-yl)-3-methyl-8,9,10,10a-tetrahydropyrido[2',3':3,4]pyrrolo[1,2-a]pyrazin-5(7H)-one and (S)-2-(4-((1,3-dihydroisobenmixture was stirred at 50° C. for 15 h before cooling to RT and diluting with water (10 mL). The mixture was extracted with EtOAc (10 mL×3) and the combined organic fractions were washed with water (20 mL×3), dried over anhydrous sodium sulfate, filtered and concentrated. The residue was purified by silica gel chromatography (0-40% EtOAc/petroleum ether) to give the title compound. MS: 495 (M+1).

Step 2: Methyl 6-(4-((1,3-dihydroisobenzofuran-5-yl)oxy)piperidin-1-yl)-5-methyl-2-(pyrazin-2-yl)nicotinate To a solution of methyl 6-(4-((1,3-dihydroisobenzofuran-5-yl)oxy)piperidin-1-yl)-2-iodo-5-methylnicotinate (320 mg, 0.324 mmol) and 2-(tributylstannyl)pyrazine (179 mg, 0.486 mmol) in toluene (5 mL) was added Pd(PPh$_3$)$_4$(37.4 mg, 0.032 mmol). The reaction mixture was stirred at 100° C. for 15 h under a nitrogen atmosphere. The reaction was cooled to RT and was diluted with water (10 mL) and extracted with ethyl acetate (10 mL×3). The combined organic fractions were washed with water (20 mL×3), dried over anhydrous sodium sulfate, filtered and concentrated. The residue was purified by silica gel chromatography (0-40% EtOAc/petroleum ether) to afford the title compound. MS: 447 (M+1).

Step 3: (R)-2-(4-((1,3-dihydroisobenzofuran-5-yl)oxy)piperidin-1-yl)-3-methyl-8,9,10,10a-tetrahydropyrido[2',3':3,4]pyrrolo[1,2-a]pyrazin-5(7H)-one and (S)-2-(4-((1,3-dihydroisobenzofuran-5-yl)oxy)piperidin-1-yl)-3-methyl-8,9,10,10a-tetrahydropyrido[2',3':3,4]pyrrolo[1,2-a]pyrazin-5(7H)-one To a solution of methyl 6-(4-((1,3-dihydroisobenzofuran-5-yl)oxy)piperidin-1-yl)-5-methyl-2-(pyrazin-2-yl)nicotinate (40 mg, 0.090 mmol) in EtOH (5 mL) was added Pd/C (10 wt %, 9.53 mg, 8.96 μmol). The reaction mixture was stirred at 30° C. for 5 h under a hydrogen atmosphere (50 psi).

The reaction mixture was filtered and the filtrate was removed under reduced pressure. The residue was purified by prep-TLC (1:2 petroleum ether:THF) to give the racemate. Chiral SFC resolution (OJ column, 40%/60% MeOH with 0.05% diethylamine modifier/CO$_2$) afforded the title compounds. Example 83A (faster eluting isomer): MS: 421 (M+1). $^1$H NMR (400 MHz, CDCl$_3$): δ 7.80 (1H, s), 7.15

(1H, d, J=8.0 Hz), 6.87 (1H, d, J=8.0 Hz), 6.84 (1H, s), 5.08 (2H, s), 5.07 (2H, s), 4.51-4.52 (1H, m), 4.37-4.40 (1H, m), 4.27-4.29 (1H, m), 3.72-3.74 (1H, m), 3.53-3.55 (2H, m), 3.11-3.20 (4H, m), 2.61-2.62 (1H, m), 2.35 (3H, s), 2.31-2.34 (1H, m), 2.26-2.28 (2H, m), 1.97-2.12 (2H, m). Example 83B (slower eluting isomer): MS: 421 (M+1). $^1$H NMR (400 MHz, CDCl$_3$): δ 7.80 (1H, s), 7.15 (1H, d, J=8.4 Hz), 6.87 (1H, d, J=8.4 Hz), 6.84 (1H, s), 5.08 (2H, s), 5.07 (2H, s), 4.51-4.52 (1H, m), 4.37-4.40 (1H, m), 4.27-4.29 (1H, m), 3.72-3.74 (1H, m), 3.54-3.55 (2H, m), 3.10-3.19 (4H, m), 2.61-2.62 (1H, m), 2.35 (3H, s), 2.31-2.34 (1H, m), 2.26-2.28 (2H, m), 1.97-2.12 (2H, m).

ASSAY PROTOCOL

The utility of the compounds as M4 muscarinic receptor allosteric modulators may be demonstrated by methodology known in the art, including by the assay described herein.

CHO-K1 cells stably transfected with human M4 receptor and chimeric G-protein Gαqi5 are thawed from liquid N$_2$ storage, resuspended in growth medium, plated in black, clear bottom 384 well plates, and incubated 16-20 hours at 37° C., 5% CO$_2$.

On the day of assay, growth medium is removed, the cells are washed 2 times with wash buffer, and cells are incubated in dye loading buffer at 37° C., 5% CO$_2$ for ~1 h. Following dye loading the cell plates are placed in a FLIPR Tetra instrument and while monitoring dye fluorescence (excitation 470-495 nM/emission 515-575 nM), 10 uL of test substance at increasing concentrations is added, and fluorescence values are recorded for 4 min. Next, 10 uL of acetylcholine is added (final concentration calculated so as to achieve 20% of the maximum acetycholine response), and the fluorescence reading is continued for 3.5 min. In some cases, a third addition of acetylcholine (final concentration calculated to achieve 70% of the maximal acetylcholine response) is performed.

The following table shows representative data for the compounds of the Examples as modulators of the M4 muscarinic acetylcholine receptor as determined by the assays described herein. Such results are indicative of the intrinsic activity of the compounds for use as allosteric modulators of the M4 muscarinic acetylcholine receptor.

TABLE 26

| Example | M4 PAM IP (nM) |
| --- | --- |
| 1 | 193 |
| 2 | 20 |
| 3 | 79 |
| 4 | 55 |
| 5 | 62 |
| 6 | 168 |
| 7 | 138 |
| 8 | 242 |
| 9 | 112 |
| 10 | 81 |
| 11 | 87 |
| 12 | 718 |
| 13 | 47 |
| 14 | 69 |
| 15 | 55 |
| 16 | 35 |
| 17 | 36 |
| 18 | 338 |
| 19 | 54 |
| 20 | 151 |
| 21 | 22 |
| 22 | 57 |
| 23 | 68 |
| 24 | 39 |
| 25 | 249 |
| 26 | 208 |
| 27 | 71 |
| 28 | 589 |
| 29A | 267 |
| 29B | 54 |
| 30 | 856 |
| 31 | 17 |
| 32 | 14 |
| 33 | 34 |
| 34 | 349 |
| 35 | 76 |
| 36 | 672 |
| 37 | 133 |
| 38 | 397 |
| 39 | 77 |
| 40 | 162 |
| 41 | 153 |
| 42 | 200 |
| 43 | 157 |
| 44 | 489 |
| 45 | 235 |
| 46 | 306 |
| 47 | 113 |
| 48 | 167 |
| 49 | 126 |
| 50 | 481 |
| 51 | 109 |
| 52 | 453 |
| 53 | 502 |
| 54 | 238 |
| 55 | 212 |
| 56 | 221 |
| 57 | 378 |
| 58 | 168 |
| 59 | 125 |
| 60 | 20 |
| 61 | 156 |
| 62 | 114 |
| 63 | 368 |
| 64 | 242 |
| 65 | 1648 |
| 66 | 1378 |
| 67 | 765 |
| 69 | 42 |
| 70 | 63 |
| 71A | 3076 |
| 71B | 1052 |
| 72 | 1511 |
| 73 | 292 |
| 74 | 119 |
| 75 | 165 |
| 76 | 221 |
| 77 | 275 |
| 78 | 287 |
| 79 | 1168 |
| 80 | 3089 |
| 81A | 29 |
| 81B | 163 |
| 82 | 92 |
| 83A | 103 |
| 84B | 25 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:
1. A compound of the formula I:

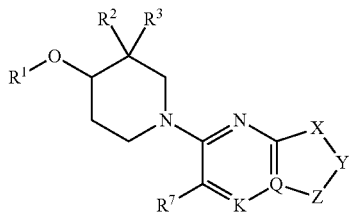

wherein:
K is N or C—$R^8$;
Q is N or C;
X is selected from the group consisting of:
  (1) =N—,
  (2) —(NR$^9$)—,
  (3) —C=O—,
  (4) =(CR$^{10}$)—, and
  (5) —(CHR$^{10}$—;
Y is selected from the group consisting of:
  (1) —O—,
  (2) =N—,
  (3) —(NR$^9$)—,
  (4) —C=O—, and
  (5) —(CR$^{11}$R$^{12}$)—;
Z is selected from the group consisting of:
  (1) —(NR$^9$)—,
  (2) —C=O—,
  (3) =(CR$^{12}$)—,
  (4) —(CHR$^{12}$)—, and
  (5) —(SO$_2$)—;
with the proviso that if X is —(CHR$^{10}$)—, Y is —(NR$^9$)—, and Z is —(C=O)—, then Q is —N—;
$R^1$ is selected from the group consisting of:
  benzodioxolyl, benzoimidazolyl, benzoxazolyl, benzoxazinone, benzooxazolone, benzothiazolyl, chromanyl, cyclopentapyridinyl, dihydrobenzo[1,4]dioxinyl, dihydrobenzofuranyl, dihydrobenzo[1,4]oxazinyl, dihydrofuropyridinyl, dihydroisobenzofuranyl, dihydroisoquinolinone, dihydropyranopyridinyl, dihydroimidazopyridine, dihydropyrido[1,4]oxazinyl, dihydroquinolinone, indazolyl, indanyl, indolyl, isochromanone, isobenzofuranone, isochromanyl, isoindolinyl, isoxazolyl, oxoisoindolinyl, phenyl, pyrazolopyridinyl, pyrazolyl, pyridyl, pyrrolopyridinyl, pyrimidinyl, quinolinone, quinolinyl, tetrahydrofuranyl, tetrahydroisoquinolinyl, tetrahydroquinolinyl, and tetrahydropyranyl, which group is substituted with one or more $R^{1a}$, $R^{1b}$ and $R^{1c}$, wherein $R^{1a}$ $R^{1b}$ and $R^{1c}$ are independently selected from the group consisting of:
  (a) hydrogen,
  (b) hydroxy,
  (c) halogen,
  (d) $C_{1-6}$alkyl, which is unsubstituted or substituted with substituents selected from the group consisting of: hydroxy, cyclopropyl, cyclobutyl, cyclopentyl, fluoro, and —OCH$_3$,
  (e) —O—$C_{1-6}$alkyl, which is unsubstituted or substituted with substituents selected from the group consisting of: hydroxy, cyclopropyl, cyclobutyl, cyclopentyl, fluoro, and —OCH$_3$,
  (f) $C_{3-6}$cycloalkyl, which is unsubstituted or substituted with substituents selected from the group consisting of: hydroxy, cyclopropyl, cyclobutyl, cyclopentyl, fluoro, and —OCH$_3$, and
  (p) —CN;
$R^2$ and $R^3$ are independently selected from the group consisting of:
  (1) hydrogen,
  (2) fluoro,
  (3) hydroxy, and
  (4) —CH$_3$;
$R^7$ and $R^8$ are independently selected from the group consisting of:
  (1) hydrogen,
  (2) $C_{1-6}$alkyl,
  (5) -fluoro, and
  (6) -chloro;
$R^9$ is selected from the group consisting of:
  (1) hydrogen,
  (2) —$C_{1-6}$alkyl, which is unsubstituted or substituted with substituents selected from the group consisting of: hydroxy, methoxy, fluoro, —C(C=O)O—$C_{1-6}$alkyl, —NH$_2$, —NH($C_{1-6}$alkyl), —N($C_{1-6}$alkyl)$_2$, —C(C=O)NH$_2$, —C(C=O)OH, oxetanyl, or pyridyl,
  (3) —$C_{3-6}$cycloalkyl, which is unsubstituted or substituted with fluoro,
  (4) —C=O—$C_{1-6}$alkyl, which is unsubstituted or substituted with substituents selected from the group consisting of: hydroxy, methoxy, ethoxy, fluoro, azetidinyl, oxetanyl, or —$C_{3-6}$cycloalkyl which is unsubstituted or substituted with fluoro, pyrrolyl, imidazolyl, —NH$_2$, —NH($C_{1-6}$alkyl), or —N($C_{1-6}$alkyl)$_2$,
  (4) —(C=O)O—$C_{1-6}$alkyl,
  (5) —(SO$_2$)—$C_{1-6}$alkyl, and
  (6) —(SO$_2$)—$C_{3-6}$cycloalkyl,
  and when Y is —(NR$^9$)—and X is —(CHR$^{10}$)—, X and Y may be joined together with —CH$_2$OCH$_2$CH$_2$—to form a morpholinyl ring, or with —CH$_2$NHCH$_2$CH$_2$—to form a piperazinyl ring;
each of $R^{10}$, $R^{11}$ and $R^{12}$ is independently selected from the group consisting of:
  (1) hydrogen,
  (2) fluoro,
  (3) —OH,
  (3) —CH$_3$,
  (4) —CF$_3$,
  (5) —CH$_2$OH,
  (6) —CH$_2$CH$_2$OH, and
  (7) —C(CH$_3$)$_2$OH;
or a pharmaceutically acceptable salt thereof.

2. The compound of claim 1, or a pharmaceutically acceptable salt thereof, wherein the group:

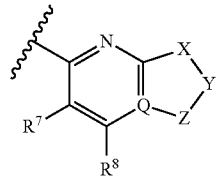

is selected from the group consisting of:

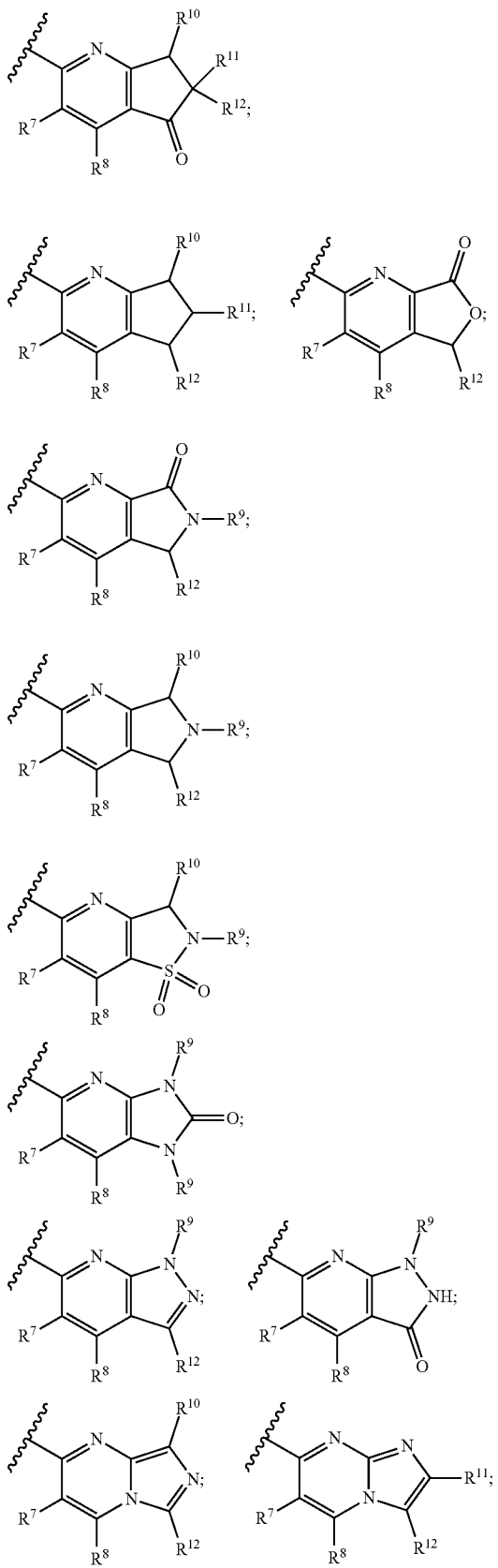

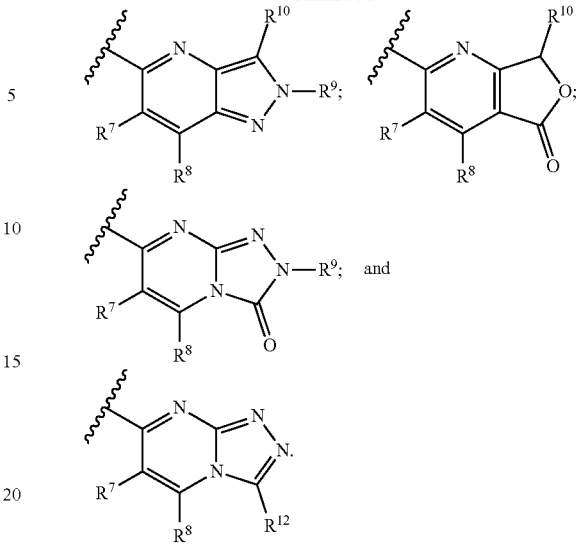

3. The compound of claim 1, or a pharmaceutically acceptable salt thereof, wherein $R^1$ is phenyl or pyridyl, which is substituted with $R^{1a}$, $R^{1b}$ and $R^{1c}$, wherein $R^{1a}$, $R^{1b}$ and $R^{1c}$ are independently selected from the group consisting of
   (a) hydrogen,
   (b) hydroxyl,
   (c) halogen,
   (d) $C_{1-6}$alkyl, which is unsubstituted or substituted with substituents selected from the group consisting of: hydroxy, fluoro, and —$OCH_3$,
   (e) —O—$C_{1-6}$alkyl, which is unsubstituted or substituted with substituents selected from the group consisting of: hydroxy, fluoro, and —$OCH_3$,
   (g) —CN.

4. The compound of claim 1, or a pharmaceutically acceptable salt thereof, wherein $R^1$ is phenyl, which is unsubstituted or substituted with —CN.

5. The compound of claim 1, or a pharmaceutically acceptable salt thereof, wherein $R^1$ is pyridyl, which is unsubstituted or substituted with —$OCH_3$.

6. The compound of claim 1, or a pharmaceutically acceptable salt thereof, wherein $R^2$ is hydrogen and $R^3$ is hydrogen.

7. The compound of claim 1, or a pharmaceutically acceptable salt thereof, wherein $R^7$ is —$CH_3$.

8. The compound of claim 1, or a pharmaceutically acceptable salt thereof, wherein $R^8$ is hydrogen.

9. The compound of claim 1, or a pharmaceutically acceptable salt thereof, wherein $R^9$ is selected from the group consisting of:
   (1) hydrogen, and
   (2) —$C_{1-6}$alkyl, which is unsubstituted or substituted with hydroxy, methoxy, 1-3 fluoro.

10. A compound which is selected from the group consisting of:
   (4-((6-methoxypyridin-3-yl)oxy)piperidin-1-yl)-3-methyl-5H-pyrrolo[3,4-b]pyridin-7(6H)-one;
   7-(4-((1,3-dihydro-2-benzofuran-5-yl)oxy)piperidin-1-yl)-6-methyl-[1,2,4]triazolo[4,3-a]pyrimidin-3(2H)-one;
   7-(4-((6-methoxypyridin-3-yl)oxy)piperidin-1-yl)-6-methyl-[1,2,4]triazolo[4,3-a]pyrimidin-3(2H)-one;

7-((3S,4R)-3-fluoro-4-((1-methyl-1H-indazol-5-yl)oxy)piperidin-1-yl)-6-methyl-[1,2,4]triazolo[4,3-a]pyrimidin-3(2H)-one;
7-(4-((2-cyclopropyl-3-oxoisoindolin-5-yl)oxy)piperidin-1-yl)-6-methyl-[1,2,4]triazolo[4,3-a]pyrimidin-3(2H)-one;
7-((3R,4R)-3-fluoro-4-(1-methyl-1H-indazol-5-yl)oxy)piperidin-1-yl)-6-methyl-[1,2,4]triazolo[4,3-a]pyrimidin-3 (2H)-one;
2,6-dimethyl-7-(4-((1-methyl-1H-indazol-5-yl)oxy)piperidin-1-yl)-[1,2,4]triazolo[4,3-a]pyrimidin-3(2H)-one;
7-((3S,4R)-3-fluoro-4-((1-methyl-1H-indazol-5-yl)oxy)piperidin-1-yl)-2,6-dimethyl-[1,2,4]triazolo[4,3-a]pyrimidin-3 (2H)-one;
7-(4-((6-methoxypyridin-3-yl)oxy)piperidin-1-yl)-2,6-dimethyl-[1,2,4]triazolo[4,3-a]pyrimidin-3 (2H)-one;
7-(4-((1,3-dihydro-2-benzofuran-5-yl)oxy)piperidin-1-yl)-2-(2-hydroxyethyl)-6-methyl-[1,2,4]triazolo[4,3-a]pyrimidin-3 (2H)-one;
2-(2-hydroxyethyl)-7-(4-((6-methoxypyridin-3-yl)oxy)piperidin-1-yl)-6-methyl-[1,2,4]triazolo[4,3-a]pyrimidin-3 (2H)-one;
6-methyl-7-(4-phenoxypiperidine-1-yl)-[1,2,4]triazolo[4,3-a]pyrimidin-3 (2H)-one;
3-((1-(6-methyl-3-oxo-2,3-dihydro-[1,2,4]triazolo[4,3-a]pyrimidin-7-yl)piperidin-4-yl)oxy)benzonitrile;
3 ((1-(2,6-dimethyl-3-oxo-2,3-dihydro-[1,2,4]triazolo[4,3-a]pyrimidin-7-yl)piperidin-4-yl)oxy)benzonitrile;
3-((1-(6-methyl-3-oxo-2,3-dihydro-[1,2,4]triazolo[4,3-a]pyrimidin-7-yl)piperidin-4-yl)oxy)benzonitrile;
2,6-dimethyl-7-(4-phenoxypiperidine-1-yl)-[1,2,4]triazolo[4,3-a]pyrimidin-3 (2H)-one;
2-(4-((6-methoxypyridin-3-yl)oxy)piperidin-1-yl)-3-methylfuro[3,4-b]pyridin-7(5H)-one;
2-(4-((6-methoxypyridin-3-yl)oxy)piperidin-1-yl)-3-methylfuro[3,4-b]pyridin-5 (7H)-one;
3-((1-(5-methyl-3-oxo-2,3-dihydro-1H-pyrazolo[3,4-b]pyridin-6-yl)piperidin-4-yl)oxy)benzonitrile;
6-(4-((6-methoxypyridin-3-yl)oxy)piperidin-1-yl)-5-methyl-1,2-dihydro-3H-pyrazolo[3,4-b]pyridin-3-one;
6-(4-((1H-indazol-6-yl)oxy)piperidin-1-yl)-5-methyl-1,2-dihydro-3H-pyrazolo[3,4-b]pyridin-3-one;
6-(4-((6-methoxypyridin-3-yl)oxy)piperidin-1-yl)-1,5-dimethyl-1,2-dihydro-3H-pyrazolo[3,4-b]pyridin-3-one;
3-((1-(1,5-dimethyl-3-oxo-2,3-dihydro-1H-pyrazolo[3,4-b]pyridin-6-yl)piperidin-4-yl)oxy)benzonitrile;
6-(4-((1H-indazol-6-yl)oxy)piperidin-1-yl)-1,5-dimethyl-1,2-dihydro-3H-pyrazolo[3,4-b]pyridin-3-one;
5-chloro-7-(4-((6-methoxypyridin-3-yl)oxy)piperidin-1-yl)-6-methylimidazo[1,2-a]pyrimidine;
(R)-2-(4-((6-methoxypyridin-3-yl)oxy)piperidin-1-yl)-3,7-dimethylfuro[3,4-b]pyridin-5(7H)-one;
(S)-2-(4-((6-methoxypyridin-3-yl)oxy)piperidin-1-yl)-3,7-dimethylfuro[3,4-b]pyridin-5 (7H)-one;
2-(4-((6-methoxypyridin-3-yl)oxy)piperidin-1-yl)-3,7,7-trimethylfuro[3,4-b]pyridin-5 (7H)-one;
3-methyl-2-(4-phenoxypiperidine-1-yl)furo[3,4-b]pyridin-5(7H)-one;
3-((1-(3-methyl-5-oxo-5,7-dihydrofuro[3,4-b]pyridin-2-yl)piperidin-4-yl)oxy)benzonitrile;
7-(hydroxymethyl)-2-(4-((6-methoxypyridin-3-yl)oxy)piperidin-1-yl)-3-methylfuro[3,4-b]pyridin-5(7H)-one;
2-(4-((6-methoxypyridin-3-yl)oxy)piperidin-1-yl)-3-methyl-6,7-dihydro-5H-pyrrolo[3,4-b]pyridine;
3-methyl-2-(4-phenoxypiperidine-1-yl)-6,7dihydro-5H-pyrrolo[3,4-b]pyridine;
2-(4-((6-methoxypyridin-3-yl)oxy)piperidin-1-yl)-3-methyl-6-(pyridin-4-ylmethyl)-5,6-dihydro-7H-pyrrolo[3,4-b]pyridin-7-one;
2-(2-(4-((6-methoxypyridin-3-yl)oxy)piperidin-1-yl)-3-methyl-5,7-dihydro-6H-pyrrolo[3,4-b]pyridin-6-yl)ethan-1-ol;
6-(4-((6-methoxypyridin-3-yl)oxy)piperidin-1-yl)-1,5-dimethyl-1H-pyrazolo[3,4-b]pyridine;
3-Hydroxy-1-(2-(4-((6-methoxypyridin-3-yl)oxy)piperidin-1-yl)-3-methyl-5,7-dihydro-6H-pyrrolo[3,4-b]pyridin-6-yl)propan-1-one;
1-(2-(4-((6-methoxypyridin-3-yl)oxy)piperidin-1-yl)-3-methyl-5,7-dihydro-6H-pyrrolo[3,4-b]pyridin-6-yl)ethan-1-one;
cyclopropyl(2-(4-((6-methoxypyridin-3-yl)oxy)piperidin-1-yl)-3-methyl-5,7-dihydro-6H-pyrrolo[3,4-b]pyridin-6-yl)methanone;
(2-(4-((6-methoxypyridin-3-yl)oxy)piperidin-1-yl)-3-methyl-5,7-dihydro-6H-pyrrolo[3,4-b]pyridin-6-yl)(3-methyloxetan-3-yl)methanone;
ethyl 2-(4-((6-methoxypyridin-3-yl)oxy)piperidin-1-yl)-3-methyl-5,7-dihydro-6H-pyrrolo[3,4-b]pyridine-6-carboxylate;
(2-(4-((6-methoxypyridin-3-yl)oxy)piperidin-1-yl)-3-methyl-5,7-dihydro-6H-pyrrolo[3,4-b]pyridin-6-yl)(1-methylcyclopentyl)methanone;
1-(2-(4-((6-methoxypyridin-3-yl)oxy)piperidin-1-yl)-3-methyl-5,7-dihydro-6H-pyrrolo[3,4-b]pyridin-6-yl)-2,2-dimethylpropan-1-one;
cyclopentyl(2-(4-((6-methoxypyridin-3-yl)oxy)piperidin-1-yl)-3-methyl-5,7-dihydro-6H-pyrrolo[3,4-b]pyridin-6-yl)methanone;
cyclopropyl(3-methyl-2-(4-phenoxypiperidine-1-yl)-5,7-dihydro-6H-pyrrolo[3,4-b]pyridin-6-yl)methanone;
(2-(4-((6-methoxypyridin-3-yl)oxy)piperidin-1-yl)-3-methyl-5,7-dihydro-6H-pyrrolo[3,4-b]pyridin-6-yl)(oxetan-2-yl)methanone;
(3,3-difluorocyclobutyl)(2-(4-((6-methoxypyridin-3-yl)oxy)piperidin-1-yl)-3-methyl-5,7-dihydro-6H-pyrrolo[3,4-b]pyridin-6-yl)methanone;
(2-(4-((6-methoxypyridin-3-yl)oxy)piperidin-1-yl)-3-methyl-5,7-dihydro-6H-pyrrolo[3,4-b]pyridin-6-yl)(1H-pyrrol-2-yl)methanone;
(S)-2-hydroxy-1-(2-(4-((6-methoxypyridin-3-yl)oxy)piperidin-1-yl)-3-methyl-5,7-dihydro-6H-pyrrolo[3,4-b]pyridin-6-yl)propan-1-one;
(2-(4-((6-methoxypyridin-3-yl)oxy)piperidin-1-yl)-3-methyl-5,7-dihydro-6H-pyrrolo[3,4-b]pyridin-6-yl)(1-methylazetidin-3-yl)methanone;
3-(dimethylamino)-1-(2-(4-((6-methoxypyridin-3-yl)oxy)piperidin-1-yl)-3-methyl-5,7-dihydro-6H-pyrrolo[3,4-b]pyridin-6-yl)propan-1-one;
2-(dimethylamino)-1-(2-(4-((6-methoxypyridin-3-yl)oxy)piperidin-1-yl)-3-methyl-5,7-dihydro-6H-pyrrolo[3,4-b]pyridin-6-yl)ethan-1-one;
(2-(4-((6-methoxypyridin-3-yl)oxy)piperidin-1-yl)-3-methyl-5,7-dihydro-6H-pyrrolo[3,4-b]pyridin-6-yl)(oxetan-3-yl)methanone;
3-methoxy-1-(2-(4-((6-methoxypyridin-3-yl)oxy)piperidin-1-yl)-3-methyl-5,7-dihydro-6H-pyrrolo[3,4-b]pyridin-6-yl)propan-1-one;
(2,2-difluorocyclopropyl)(2-(4-((6-methoxypyridin-3-yl)oxy)piperidin-1-yl)-3-methyl-5,7-dihydro-6H-pyrrolo[3,4-b]pyridin-6-yl)methanone;
6-(cyclopropyl sulfonyl)-2-(4-((6-methoxypyridin-3-yl)oxy)piperidin-1-yl)-3-methyl-6,7-dihydro-5H-pyrrolo[3,4-b]pyridine;

2-(4-((6-methoxypyridin-3-yl)oxy)piperidin-1-yl)-3-methyl-6-(methyl sulfonyl)-6,7-dihydro-5H-pyrrolo[3,4-b]pyridine;

3-methyl-6-(methylsulfonyl)-2-(4-phenoxypiperidine-1-yl)-6,7-dihydro-5H-pyrrolo[3,4-b]pyridine;

methyl 2-(4-((6-methoxypyridin-3-yl)oxy)piperidin-1-yl)-3-methyl-5,7-dihydro-6H-pyrrolo[3,4-b]pyridine-6-carboxylate;

methyl 3-methyl-2-(4-phenoxypiperidine-1-yl)-5,7-dihydro-6H-pyrrolo[3,4-b]pyridine-6-carboxylate;

6-(4-((6-methoxypyridin-3-yl)oxy)piperidin-1-yl)-5-methyl-1H-pyrazolo[3,4-b]pyridine;

5-(4-((6-methoxypyridin-3-yl)oxy)piperidin-1-yl)-2,6-dimethyl-2H-pyrazolo[4,3-b]pyridine;

5-(4((6-methoxypyridin-3-yl)oxy)piperidin-1-yl)-3,6-dimethyl-1H-pyrazolo[4,3-b]pyridine;

5-(4((6-methoxypyridin-3-yl)oxy)piperidin-1-yl)-1,6-dimethyl-1H-pyrazolo[4,3-b]pyridine;

7-(4-((6-methoxypyridin-3-yl)oxy)piperidin-yl)-6-methylimidazo[1,2-a]pyrimidine;

2-(4-((6-methoxypyridin-3-yl)oxy)piperidin-1-yl)-3-methyl-6,7-dihydro-5H-pyrrolo[3,4-b]pyrazin-5-one;

2-(4-((6-methoxypyridin-3-yl)oxy)piperidin-1-yl)-3-methyl-6,7-dihydro-5H-cyclopenta[b]pyridin-5-one;

6,6-difluoro-2-(4-((6-methoxypyridin-3-yl)oxy)piperidin-1-yl)-3-methyl-6,7-dihydro-5H-cyclopenta[b]pyridin-5-one;

(R)-2-(4-((6-methoxypyridin-3-yl)oxy)piperidin-1-yl)-3-methyl-6,7-dihydro-5H-cyclopenta[b]pyridin-5-ol;

(S)-2-(4-((6-methoxypyridin-3-yl)oxy)piperidin-1-yl)-3-methyl-6,7-dihydro-5H-cyclopenta[b]pyridin-5-ol;

2-(4-((6-methoxypyridin-3-yl)oxy)piperidin-1-yl)-3-methyl-6,7-dihydro-5H-cyclopenta[b]pyridine; 2-(4-(6-methoxypyridin-3-yl)oxy)piperidin-1-yl)-3,6,6-trimethyl-6,7-dihydro-5H-cyclopenta[b]pyridin-5-one;

2-(4-((6-methoxypyridin-3-yl)oxy)piperidin-1-yl)-3,6-dimethyl-6,7-dihydro-5H-cyclopenta[b]pyridin-5-one;

5-(4-((6-methoxypyridin-3-yl)oxy)piperidin-1-yl)-6-methyl-2,3-dihydroisothiazolo[4,5-b]pyridine 1,1-dioxide;

3-((1-(6-methyl-1,1-dioxido-2,3-dihydroisothiazolo[4,5-b]pyridin-5-yl)piperidin-4-yl)oxy)benzonitrile;

6-methyl-5-(4-phenoxypiperidine-1-yl)-2,3-dihydroisothiazolo[4,5-b]pyridine 1,1-dioxide 2-(4-((6-methoxypyridin-3-yl)oxy)piperidin-1-yl)-3-methyl-6-(trifluoromethyl)imidazo[1,5-a]pyrimidine;

5-(4-((6-methoxypyridin-3-yl)oxy)piperidin-1-yl)-6-methyl-1,3-dihydro-2H-imidazo[4,5-b]pyridin-2-one;

7-(4-((6-methoxypyridin-3-yl)oxy)piperidin-1-yl)-6-methyl-3-(trifluoromethyl)-[1,2,4]triazolo[4,3-a]pyrimidine;

or a pharmaceutically acceptable salt thereof.

11. A pharmaceutical composition which comprises an inert carrier and a compound of claim 1 or a pharmaceutically acceptable salt thereof.

* * * * *